US010993826B2

(12) United States Patent
Romo et al.

(10) Patent No.: US 10,993,826 B2
(45) Date of Patent: May 4, 2021

(54) ORTHOPEDIC DEVICE

(71) Applicant: Ossur Iceland ehf, Reykjavik (IS)

(72) Inventors: Harry Duane Romo, Foothill Ranch, CA (US); Jonathan Walborn, Foothill Ranch, CA (US)

(73) Assignee: OSSUR ICELAND EHF, Reykjavik (IS)

(*) Notice: Subject to any disclaimer, the term of this patent is extended or adjusted under 35 U.S.C. 154(b) by 365 days.

(21) Appl. No.: 15/581,248

(22) Filed: Apr. 28, 2017

(65) Prior Publication Data

US 2017/0231796 A1    Aug. 17, 2017

Related U.S. Application Data

(63) Continuation of application No. 15/137,075, filed on Apr. 25, 2016, now Pat. No. 9,668,907, which is a
(Continued)

(51) Int. Cl.
*A61F 5/01* (2006.01)
*A61F 5/34* (2006.01)
(Continued)

(52) U.S. Cl.
CPC .......... *A61F 5/0127* (2013.01); *A61F 5/0102* (2013.01); *A61F 5/012* (2013.01);
(Continued)

(58) Field of Classification Search
CPC .... A61F 5/0111; A61F 5/0102; A61F 5/0127; A61F 5/0109; A61F 5/0195; A61F 5/01;
(Continued)

(56) References Cited

U.S. PATENT DOCUMENTS 975,576 A    11/1910  Sexton
1,012,017 A  12/1911  Salt
(Continued)

FOREIGN PATENT DOCUMENTS

CN    101711141 A    5/2010
CN    102026592 A    4/2011
(Continued)

OTHER PUBLICATIONS

Chinese Office Action from CN Application No. 201480052921.0, dated Feb. 4, 2017.
(Continued)

*Primary Examiner* — Ophelia A Hawthorne
(74) *Attorney, Agent, or Firm* — Workman Nydegger

(57) ABSTRACT

An orthopedic system includes a base shell forming an opening over a dorsal aspect thereof and a dorsal shell contoured to generally correspond to the opening of the base shell. The base shell has a proximal member and a distal member connected to the proximal member, each has a semi-rigid shell configuration to protect and support a lower leg, an ankle, or a foot of a user when received in the orthopedic system. A flexible toe portion is attached to a distal terminal end area of the distal member and formed of a different material than the distal member. The flexible toe portion is arranged to terminate above an upper surface of the user's toes and to flex relative to the distal member and the toes so as to reduce the likelihood of pressure points on the toes from the distal member.

19 Claims, 29 Drawing Sheets

Related U.S. Application Data continuation-in-part of application No. 14/496,558, filed on Sep. 25, 2014, now Pat. No. 9,839,550.

(60) Provisional application No. 61/899,432, filed on Nov. 4, 2013, provisional application No. 61/882,188, filed on Sep. 25, 2013.

(51) Int. Cl.
*A61H 3/00* (2006.01)
*A61F 5/058* (2006.01)

(52) U.S. Cl.
CPC .......... *A61F 5/0111* (2013.01); *A61F 5/0195* (2013.01); *A61F 5/0585* (2013.01); *A61F 5/34* (2013.01); *A61H 3/00* (2013.01); *A61F 2005/0188* (2013.01); *A61H 2003/005* (2013.01)

(58) Field of Classification Search
CPC ........ A61F 5/0585; A61F 5/00; A61F 13/062; A61F 13/066; A61F 13/043; A61F 13/064; A61F 5/058; A61F 5/3715; A61F 5/0113; A61F 5/3761; A61F 13/068; A61F 13/102; A61F 2007/0044; A61F 5/022; A61F 5/05841; A61F 5/14; A61F 2005/0188; A61F 13/04; A61F 5/34; A61F 5/028; A61F 5/05816; A61F 5/012; A61F 5/019; A61F 5/0193; A61H 2003/005; A61H 3/00; A61H 9/0078; A43B 7/28; A43B 7/14; A43B 7/20

See application file for complete search history.

(56) References Cited

U.S. PATENT DOCUMENTS

| | | |
|---|---|---|
| 2,200,849 A | 5/1940 | Margolin |
| 2,236,367 A | 3/1941 | Gruber |
| 2,292,297 A | 8/1942 | Sherlock |
| 2,444,640 A | 7/1948 | Epstein |
| 2,868,191 A | 1/1959 | Juhasz |
| 2,885,797 A | 5/1959 | Chrencik |
| 2,888,016 A | 5/1959 | De Lamater |
| 2,909,854 A | 10/1959 | Edelstein |
| 2,913,837 A | 11/1959 | Geuder |
| 2,917,844 A | 12/1959 | Scholl |
| 2,928,193 A | 3/1960 | Kristan |
| 2,979,835 A | 4/1961 | Scholl |
| 2,979,836 A | 4/1961 | Scholl |
| 3,270,358 A | 9/1966 | Milner |
| 3,464,126 A | 9/1969 | Sarkissian |
| 3,548,420 A | 12/1970 | Spence |
| 3,580,248 A | 5/1971 | Larson |
| 3,681,860 A | 8/1972 | Bidegain |
| 3,685,176 A | 8/1972 | Rudy |
| 3,730,169 A | 5/1973 | Fiber |
| 3,735,758 A | 5/1973 | Novotney |
| 3,760,056 A | 9/1973 | Rudy |
| 3,786,805 A | 1/1974 | Tourin |
| 3,792,537 A | 2/1974 | Plank et al. |
| 3,814,088 A | 6/1974 | Raymond |
| 3,834,377 A | 9/1974 | Lebold |
| 3,859,740 A | 1/1975 | Kemp |
| 3,922,800 A | 12/1975 | Miller et al. |
| 3,953,930 A * | 5/1976 | Ramer ................. A43B 5/0472 36/94 |
| 3,955,565 A | 5/1976 | Johnson, Jr. |
| 4,045,888 A | 9/1977 | Oxenberg |
| 4,057,056 A | 11/1977 | Payton |
| 4,095,353 A | 6/1978 | Foldes |
| 4,100,686 A | 7/1978 | Sgarlato et al. |
| 4,142,307 A | 3/1979 | Martin |
| 4,177,583 A | 12/1979 | Chapman |
| 4,184,273 A | 1/1980 | Boyer et al. |
| 4,217,706 A | 8/1980 | Vartanian |
| 4,217,893 A | 8/1980 | Payton |
| 4,232,459 A | 11/1980 | Vaccari |
| 4,237,626 A | 12/1980 | Brown |
| 4,267,649 A | 5/1981 | Smith |
| 4,300,294 A | 11/1981 | Riecken |
| 4,333,248 A | 6/1982 | Samuels |
| 4,370,818 A | 2/1983 | Simoglou |
| 4,408,402 A | 10/1983 | Looney |
| 4,414,965 A | 11/1983 | Mauldin et al. |
| D272,281 S | 1/1984 | Alush |
| 4,446,856 A | 5/1984 | Jordan |
| 4,494,536 A | 1/1985 | Latenser |
| 4,505,269 A | 3/1985 | Davies et al. |
| 4,550,721 A | 11/1985 | Michel |
| 4,565,017 A | 1/1986 | Ottieri |
| 4,571,853 A | 2/1986 | Medrano |
| 4,572,169 A | 2/1986 | Mauldin et al. |
| 4,587,962 A | 5/1986 | Greene et al. |
| 4,598,484 A | 7/1986 | Ma |
| 4,599,811 A | 7/1986 | Rousseau |
| 4,608,768 A | 9/1986 | Cavanagh |
| 4,620,378 A | 11/1986 | Sartor |
| 4,633,598 A | 1/1987 | Moronaga et al. |
| 4,633,599 A | 1/1987 | Morell et al. |
| 4,633,877 A | 1/1987 | Pendergast |
| 4,660,300 A | 4/1987 | Morell et al. |
| 4,669,202 A | 6/1987 | Ottieri |
| 4,674,204 A | 6/1987 | Sullivan et al. |
| 4,674,205 A | 6/1987 | Anger |
| 4,677,767 A | 7/1987 | Darby |
| 4,680,878 A | 7/1987 | Pozzobon et al. |
| 4,689,898 A | 9/1987 | Fahey |
| 4,719,710 A | 1/1988 | Pozzobon |
| 4,727,661 A | 3/1988 | Kuhn |
| 4,741,115 A | 5/1988 | Pozzobon |
| 4,748,726 A | 6/1988 | Schoch |
| 4,760,653 A | 8/1988 | Baggio |
| 4,771,768 A | 9/1988 | Crispin |
| 4,773,170 A | 9/1988 | Moore et al. |
| 4,793,078 A | 12/1988 | Andrews |
| D299,787 S | 2/1989 | Bates |
| 4,805,321 A | 2/1989 | Tonkel |
| 4,805,601 A | 2/1989 | Eischen, Sr. |
| 4,811,504 A | 3/1989 | Bunke |
| 4,839,972 A * | 6/1989 | Pack ................... A43B 5/0472 36/114 |
| 4,869,001 A | 9/1989 | Brown |
| 4,872,273 A | 10/1989 | Smeed |
| 4,879,822 A | 11/1989 | Hayes |
| 4,893,418 A | 1/1990 | Ogden |
| 4,934,355 A | 6/1990 | Porcelli |
| 4,947,838 A | 8/1990 | Giannetti |
| 4,974,583 A | 12/1990 | Freitas |
| 5,065,481 A | 11/1991 | Walkhoff |
| 5,065,531 A | 11/1991 | Prestridge |
| 5,078,128 A | 1/1992 | Grim et al. |
| 5,123,180 A | 6/1992 | Nannig et al. |
| 5,125,400 A | 6/1992 | Johnson, Jr. |
| D329,527 S | 9/1992 | Cohen |
| 5,143,058 A | 9/1992 | Luber et al. |
| D330,109 S | 10/1992 | Hatfield |
| 5,152,038 A | 10/1992 | Schoch |
| 5,154,682 A | 10/1992 | Kellerman |
| 5,154,695 A | 10/1992 | Farris et al. |
| 5,157,813 A | 10/1992 | Carroll |
| 5,176,623 A | 1/1993 | Stetman et al. |
| 5,176,624 A | 1/1993 | Kuehnreich |
| 5,183,036 A | 2/1993 | Spademan |
| 5,197,942 A | 3/1993 | Brady |
| D334,646 S | 4/1993 | Dissinger |
| D337,876 S | 8/1993 | Kilbey |
| 5,233,767 A | 8/1993 | Kramer |
| 5,242,379 A | 9/1993 | Harris et al. |
| 5,257,470 A | 11/1993 | Auger et al. |
| 5,277,695 A | 1/1994 | Johnson, Jr. et al. |
| D344,589 S | 2/1994 | Kilbey |
| 5,288,286 A | 2/1994 | Davis et al. |

(56) References Cited

U.S. PATENT DOCUMENTS

| | | |
|---|---|---|
| 5,325,613 A | 7/1994 | Sussmann |
| 5,329,705 A | 7/1994 | Grim et al. |
| D352,191 S | 11/1994 | Zorian |
| D352,784 S | 11/1994 | Cohen et al. |
| 5,359,791 A | 11/1994 | Prahl et al. |
| 5,368,549 A | 11/1994 | McVicker |
| 5,368,551 A | 11/1994 | Zuckerman |
| 5,370,133 A | 12/1994 | Darby et al. |
| 5,378,223 A | 1/1995 | Grim et al. |
| 5,399,152 A | 3/1995 | Habermeyer et al. |
| 5,407,421 A | 4/1995 | Goldsmith |
| 5,425,701 A | 6/1995 | Oster et al. |
| 5,426,872 A | 6/1995 | Hayes |
| 5,429,377 A | 7/1995 | Duer |
| 5,429,588 A | 7/1995 | Young et al. |
| 5,433,695 A | 7/1995 | Drennan |
| 5,435,009 A | 7/1995 | Schild et al. |
| 5,438,768 A | 8/1995 | Bauerfeind |
| 5,441,015 A | 8/1995 | Farley |
| D363,780 S | 10/1995 | Darby et al. |
| 5,464,385 A | 11/1995 | Grim |
| 5,477,593 A | 12/1995 | Leick |
| D365,919 S | 1/1996 | Chen |
| 5,483,757 A | 1/1996 | Frykberg |
| 5,496,263 A | 3/1996 | Fuller, II et al. |
| 5,548,848 A | 8/1996 | Huybrechts |
| 5,548,910 A * | 8/1996 | Klingseis ............ A43B 5/185 36/135 |
| D373,548 S | 9/1996 | Losi, II |
| 5,558,627 A | 9/1996 | Singer et al. |
| D375,191 S | 11/1996 | Tonkel et al. |
| 5,577,998 A | 11/1996 | Johnson, Jr. et al. |
| D376,429 S | 12/1996 | Antar |
| 5,617,650 A | 4/1997 | Grim |
| D379,258 S | 5/1997 | Cheng |
| 5,641,322 A | 6/1997 | Silver et al. |
| 5,647,104 A | 7/1997 | James |
| 5,656,226 A | 8/1997 | McVicker |
| D383,250 S | 9/1997 | Amico |
| D384,746 S | 10/1997 | Varn |
| D390,345 S | 2/1998 | Aird et al. |
| 5,717,996 A | 2/1998 | Feldmann |
| D391,748 S | 3/1998 | Koh |
| 5,761,834 A | 6/1998 | Grim et al. |
| 5,778,563 A | 7/1998 | Ahlbaumer |
| 5,778,565 A | 7/1998 | Holt et al. |
| 5,797,862 A | 8/1998 | Lamont |
| D398,142 S | 9/1998 | Benoit |
| D398,439 S | 9/1998 | McDonald |
| 5,819,378 A | 10/1998 | Doyle |
| 5,827,210 A * | 10/1998 | Antar ............ A43B 7/00 602/23 |
| 5,827,211 A * | 10/1998 | Sellinger ............ A61F 5/0195 602/27 |
| D401,042 S | 11/1998 | Davis |
| 5,833,639 A | 11/1998 | Nunes et al. |
| 5,836,902 A | 11/1998 | Gray |
| 5,846,063 A | 12/1998 | Lakic |
| 5,853,380 A | 12/1998 | Miller |
| 5,857,987 A | 1/1999 | Habermeyer |
| D404,895 S | 2/1999 | Rosato |
| 5,868,690 A | 2/1999 | Eischen, Sr. |
| 5,913,841 A | 6/1999 | Lamont |
| 5,934,599 A | 8/1999 | Hammerslag |
| 5,951,504 A | 9/1999 | Iglesias et al. |
| 5,961,477 A | 10/1999 | Turtzo |
| 5,993,404 A | 11/1999 | McNiel |
| 6,000,148 A | 12/1999 | Cretinon |
| D418,967 S | 1/2000 | Stengel |
| 6,021,780 A | 2/2000 | Darby |
| 6,027,468 A | 2/2000 | Pick |
| 6,044,578 A | 4/2000 | Kelz |
| 6,098,315 A | 8/2000 | Hoffmann, III |
| 6,131,195 A | 10/2000 | Foreman |
| 6,202,953 B1 | 3/2001 | Hammerslag |
| 6,205,685 B1 | 3/2001 | Kellerman |
| D440,754 S | 4/2001 | Bathum |
| 6,228,044 B1 | 5/2001 | Jensen et al. |
| 6,267,742 B1 | 7/2001 | Krivosha et al. |
| RE37,338 E | 8/2001 | McVicker |
| 6,289,558 B1 | 9/2001 | Hammerslag |
| 6,334,854 B1 | 1/2002 | Davis |
| 6,338,768 B1 | 1/2002 | Chi |
| 6,361,514 B1 | 3/2002 | Brown et al. |
| 6,377,178 B1 | 4/2002 | Detoro et al. |
| 6,409,691 B1 | 6/2002 | Dakin et al. |
| D461,936 S | 8/2002 | Fiorini et al. |
| 6,432,073 B2 | 8/2002 | Pior et al. |
| D467,708 S | 12/2002 | Portzline |
| D473,654 S | 4/2003 | Iglesias et al. |
| D473,704 S | 4/2003 | Wilson |
| 6,572,571 B2 | 6/2003 | Lowe |
| D476,799 S | 7/2003 | Fuerst |
| 6,589,194 B1 | 7/2003 | Calderon et al. |
| 6,682,497 B2 | 1/2004 | Jensen et al. |
| 6,755,798 B2 | 6/2004 | McCarthy et al. |
| 6,792,699 B2 | 9/2004 | Long |
| D500,855 S | 1/2005 | Pick et al. |
| 6,866,043 B1 | 3/2005 | Davis |
| D504,005 S | 4/2005 | Schoenborn et al. |
| D505,727 S | 5/2005 | Krahner et al. |
| 6,945,944 B2 | 9/2005 | Kuiper et al. |
| 6,976,972 B2 | 12/2005 | Bradshaw |
| 6,991,613 B2 | 1/2006 | Sensabaugh |
| D517,306 S | 3/2006 | Hoeft |
| 7,010,823 B2 | 3/2006 | Baek |
| 7,018,351 B1 | 3/2006 | Iglesias et al. |
| D523,217 S | 6/2006 | Matis et al. |
| D528,214 S | 9/2006 | Binet |
| 7,198,610 B2 | 4/2007 | Ingimundarson et al. |
| 7,281,341 B2 | 10/2007 | Reagan et al. |
| 7,288,076 B2 | 10/2007 | Grim et al. |
| D554,835 S | 11/2007 | Peydro |
| D555,291 S | 11/2007 | Danzo |
| D555,343 S | 11/2007 | Bettencourt |
| 7,303,538 B2 | 12/2007 | Grim et al. |
| 7,311,686 B1 | 12/2007 | Iglesias et al. |
| 7,354,411 B2 | 4/2008 | Perry et al. |
| RE40,363 E | 6/2008 | Grim et al. |
| 7,384,584 B2 * | 6/2008 | Jerome ............ A61F 5/0111 264/222 |
| D575,039 S | 8/2008 | Amado et al. |
| D576,781 S | 9/2008 | Chang et al. |
| 7,418,755 B2 | 9/2008 | Bledsoe et al. |
| D583,544 S | 12/2008 | Fuerst |
| D583,956 S | 12/2008 | Chang et al. |
| 7,493,706 B2 | 2/2009 | Cho et al. |
| 7,524,295 B1 | 4/2009 | Peters et al. |
| D592,755 S | 5/2009 | Chang et al. |
| D592,756 S | 5/2009 | Chang et al. |
| D594,368 S | 6/2009 | Butler |
| D596,301 S | 7/2009 | Campos et al. |
| D596,386 S | 7/2009 | Brambilla |
| 7,591,050 B2 | 9/2009 | Hammerslag |
| D603,155 S | 11/2009 | Della Valle et al. |
| D614,775 S | 4/2010 | Snively |
| D615,285 S | 5/2010 | Martin |
| D616,556 S | 5/2010 | Hu |
| 7,717,869 B2 | 5/2010 | Eischen, Sr. |
| 7,727,174 B2 | 6/2010 | Chang et al. |
| D622,494 S | 8/2010 | Warren |
| 7,838,717 B2 | 11/2010 | Haggstrom et al. |
| D634,438 S | 3/2011 | Hu |
| D634,852 S | 3/2011 | Hu |
| D636,157 S | 4/2011 | Nascimento |
| D636,159 S | 4/2011 | Petrie |
| 7,964,766 B2 | 6/2011 | Blott et al. |
| D642,363 S | 8/2011 | Rajmohan et al. |
| D642,775 S | 8/2011 | Raysse |
| 8,002,724 B2 | 8/2011 | Hu et al. |
| 8,012,112 B2 | 9/2011 | Barberio |
| 8,021,347 B2 | 9/2011 | Vitaris et al. |
| D648,113 S | 11/2011 | Chang |
| RE43,063 E | 1/2012 | Kim |

(56) References Cited

U.S. PATENT DOCUMENTS

| | | | |
|---|---|---|---|
| D651,381 S | 1/2012 | Simms | |
| 8,158,844 B2 | 4/2012 | McNeil | |
| D661,887 S | 6/2012 | Petrie | |
| 8,308,705 B2 | 11/2012 | Lin et al. | |
| 8,313,449 B2 | 11/2012 | Hardman et al. | |
| D675,421 S | 2/2013 | Petrie | |
| D677,866 S | 3/2013 | Vestuti et al. | |
| D680,728 S | 4/2013 | Stryjak | |
| D682,517 S | 5/2013 | Taylor | |
| D683,214 S | 5/2013 | McAdam | |
| D684,760 S | 6/2013 | Williams, Jr. | |
| 8,506,510 B2 | 8/2013 | Hu et al. | |
| D689,677 S | 9/2013 | Bathum et al. | |
| 8,549,774 B2 * | 10/2013 | Meschter | A43B 5/12 36/102 |
| 8,574,181 B2 | 11/2013 | Bird et al. | |
| D696,499 S | 12/2013 | Lehtinen | |
| D696,785 S | 12/2013 | Weaver, II et al. | |
| D698,074 S | 1/2014 | Hargreaves | |
| D698,338 S | 1/2014 | Ingham et al. | |
| D700,404 S | 2/2014 | Niefer | |
| D701,032 S | 3/2014 | Leleu | |
| D701,033 S | 3/2014 | Leleu | |
| D703,335 S | 4/2014 | Bird et al. | |
| D709,277 S | 7/2014 | Takenaka | |
| D712,639 S | 9/2014 | Spring | |
| D714,042 S | 9/2014 | Petrie | |
| 9,003,677 B2 | 4/2015 | Goodsmith et al. | |
| D729,393 S | 5/2015 | Dunn et al. | |
| D740,896 S | 10/2015 | Halper, Jr. | |
| D742,017 S | 10/2015 | Dunn et al. | |
| D744,111 S | 11/2015 | Dunn et al. | |
| 9,220,621 B2 | 12/2015 | Hu et al. | |
| 9,220,622 B2 | 12/2015 | Ingimundarson et al. | |
| 9,248,042 B2 | 2/2016 | Lopez et al. | |
| 9,333,106 B2 | 5/2016 | Hu et al. | |
| 9,468,553 B2 | 10/2016 | Hu et al. | |
| D772,418 S | 11/2016 | Dunn et al. | |
| 9,492,301 B2 | 11/2016 | Hu et al. | |
| D776,288 S | 1/2017 | Dunn et al. | |
| D776,289 S | 1/2017 | Dunn et al. | |
| 9,744,065 B2 | 8/2017 | Walborn et al. | |
| 9,839,548 B2 | 12/2017 | Ingvarsson et al. | |
| 9,839,549 B2 | 12/2017 | Walborn et al. | |
| 2002/0095105 A1 | 7/2002 | Jensen | |
| 2002/0095750 A1 | 7/2002 | Hammerslag | |
| 2002/0128574 A1 | 9/2002 | Darby | |
| 2003/0093882 A1 | 5/2003 | Gorza et al. | |
| 2003/0171703 A1 | 9/2003 | Grim et al. | |
| 2003/0204938 A1 | 11/2003 | Hammerslag | |
| 2004/0010212 A1 | 1/2004 | Kuiper et al. | |
| 2004/0019307 A1 | 1/2004 | Grim et al. | |
| 2004/0167453 A1 | 8/2004 | Peters | |
| 2005/0131324 A1 | 6/2005 | Bledsoe | |
| 2005/0145256 A1 | 7/2005 | Howard et al. | |
| 2005/0165338 A1 | 7/2005 | Iglesias et al. | |
| 2005/0171461 A1 * | 8/2005 | Pick | A61F 5/0111 602/27 |
| 2005/0172517 A1 | 8/2005 | Bledsoe et al. | |
| 2005/0274046 A1 | 12/2005 | Schwartz | |
| 2006/0084899 A1 | 4/2006 | Verkade et al. | |
| 2006/0135899 A1 | 6/2006 | Jerome et al. | |
| 2006/0135902 A1 | 6/2006 | Ingimundarson et al. | |
| 2006/0156517 A1 | 7/2006 | Hammerslag et al. | |
| 2006/0189907 A1 | 8/2006 | Pick et al. | |
| 2006/0217649 A1 | 9/2006 | Rabe | |
| 2006/0229541 A1 | 10/2006 | Hassler et al. | |
| 2007/0055188 A1 | 3/2007 | Avni et al. | |
| 2007/0167884 A1 | 7/2007 | Mangrum et al. | |
| 2007/0169378 A1 | 7/2007 | Sodeberg et al. | |
| 2007/0185425 A1 | 8/2007 | Einarsson et al. | |
| 2007/0191749 A1 | 8/2007 | Barberio | |
| 2007/0282230 A1 | 12/2007 | Valderrabano et al. | |
| 2007/0293798 A1 | 12/2007 | Hu et al. | |
| 2008/0060167 A1 | 3/2008 | Hammerslag et al. | |
| 2008/0060168 A1 | 3/2008 | Hammerslag et al. | |
| 2008/0066272 A1 | 3/2008 | Hammerslag et al. | |
| 2008/0066345 A1 | 3/2008 | Hammerslag et al. | |
| 2008/0066346 A1 | 3/2008 | Hammerslag et al. | |
| 2008/0083135 A1 | 4/2008 | Hammerslag et al. | |
| 2008/0294082 A1 | 11/2008 | Chang et al. | |
| 2008/0294083 A1 | 11/2008 | Chang et al. | |
| 2009/0012482 A1 | 1/2009 | Pinto et al. | |
| 2009/0099495 A1 | 4/2009 | Campos et al. | |
| 2009/0227927 A1 | 9/2009 | Frazer | |
| 2009/0270820 A1 | 10/2009 | Johnson et al. | |
| 2009/0287127 A1 | 11/2009 | Hu et al. | |
| 2009/0287128 A1 | 11/2009 | Ingimundarson et al. | |
| 2010/0011624 A1 * | 1/2010 | Polegato Moretti | B29D 35/128 36/3 A |
| 2010/0069808 A1 | 3/2010 | Mitchell | |
| 2010/0100020 A1 | 4/2010 | Fout et al. | |
| 2010/0234782 A1 | 9/2010 | Hu et al. | |
| 2010/0324461 A1 | 12/2010 | Darby, II et al. | |
| 2011/0009791 A1 | 1/2011 | Hopmann | |
| 2011/0015555 A1 | 1/2011 | Anderson et al. | |
| 2011/0196275 A1 | 8/2011 | Chang et al. | |
| 2012/0010534 A1 | 1/2012 | Kubiak et al. | |
| 2012/0035560 A1 | 2/2012 | Eddy et al. | |
| 2012/0078148 A1 | 3/2012 | Hu et al. | |
| 2012/0220960 A1 | 8/2012 | Ruland | |
| 2012/0238924 A1 | 9/2012 | Avni | |
| 2013/0066247 A1 | 3/2013 | Bird et al. | |
| 2013/0310721 A1 | 11/2013 | Hu et al. | |
| 2014/0128789 A1 | 5/2014 | Chen | |
| 2014/0171837 A1 | 6/2014 | Harcourt | |
| 2014/0276310 A1 | 9/2014 | Grim et al. | |
| 2014/0350446 A1 | 11/2014 | Gunnsteinsson | |
| 2015/0075030 A1 | 3/2015 | Walborn et al. | |
| 2015/0164179 A1 | 6/2015 | Walborn et al. | |
| 2016/0213823 A1 | 7/2016 | Walborn et al. | |

FOREIGN PATENT DOCUMENTS

| | | |
|---|---|---|
| DE | 23 416 58 A1 | 3/1974 |
| DE | 32 287 53 A1 | 2/1984 |
| EP | 0 095 396 A1 | 11/1983 |
| EP | 0 201 051 A1 | 11/1986 |
| EP | 0770368 A1 | 5/1997 |
| EP | 2468323 A1 | 6/2012 |
| FR | 2 399 811 A1 | 3/1979 |
| FR | 2634988 A1 | 2/1990 |
| FR | 2 681 516 A1 | 3/1993 |
| GB | 2 124 473 A | 2/1984 |
| GB | 2 178 940 A | 2/1987 |
| JP | 2005211626 A | 8/2005 |
| WO | 93/13685 A1 | 7/1993 |
| WO | 93/24081 A1 | 12/1993 |
| WO | 94/18863 A1 | 9/1994 |
| WO | 97/36507 A1 | 10/1997 |
| WO | 2004/021817 A1 | 3/2004 |
| WO | 2006035469 A2 | 4/2006 |
| WO | 2006045079 A1 | 4/2006 |
| WO | 2007078845 A2 | 7/2007 |
| WO | 2010104824 A1 | 9/2010 |
| WO | 2013/084213 A1 | 6/2013 |
| WO | 2015006766 A1 | 1/2015 |

OTHER PUBLICATIONS

International Search Report from PCT Application No. PCT/US2009/003018, dated Jul. 24, 2009.

Product Information Sheet: Nextep Contour Walker, Procare, DJ Orthopedics, Jan. 1, 2008,1 page. Retrieved from the internet, www.djortho.com.

Product Information Sheet: Nextep Contour w/ Air Walker, Procare, DJ Orthopedics, Jan. 1, 2008, 1 page. Retrieved from internet, www.djortho.com.

Product Information Sheet: XP Achilles Walker (EU only), Aircast, Jan. 1, 2008, 4 pages. Retrieved from the internet, http://www.aircast.com/index.asp/fuseaction/products.detail/cat/2/id/104.

(56) References Cited

OTHER PUBLICATIONS

Product Information Sheet: XP Diabetic Walker System, Aircast, Jan. 1, 2008, 4 pages. Retrieved from the internet, http://www.aircast.com/index.asp/fuseaction/products.detail/cat/2/id/15.
Product Information Sheet: SP Walker (short pneumatic), Aircast, Jan. 1, 2008, 4 pages. Retrieved from the internet, http://www.aircast.com/index.asp/fuseaction/products.detail/cat/2/id/14.
Product Information Sheet: FP Walker (foam pneumatic), Aircast, Jan. 1, 2008, 4 pages. Retrieved from the internet, http://www.aircast.com/index.asp/fuseaction/products.detail/cat/2/id/75.
Product Information Sheet: XP Walker (extra pneumatic), Aircast, Jan. 1, 2008, 4 pages. Retrieved from the internet, http://www.aircast.com/index.asp/fuseaction/products.detail/cat/2/id/76.
International Search Report and Written Opinion from International Application No. PCT/US2014/057421, dated Dec. 8, 2014.
International Search Report and Written Opinion from International Application No. PCT/US2014/069686, dated Mar. 13, 2015.
International Search Report and Written Opinion for corresponding International Application No. PCT/US2014/056201, dated Dec. 5, 2014.
International Search Report from PCT Application No. PCT/US2016/014816, dated Apr. 28, 2016.
European Search Report from European Application No. EP 15 20 0198.8, dated May 20, 2016.

* cited by examiner

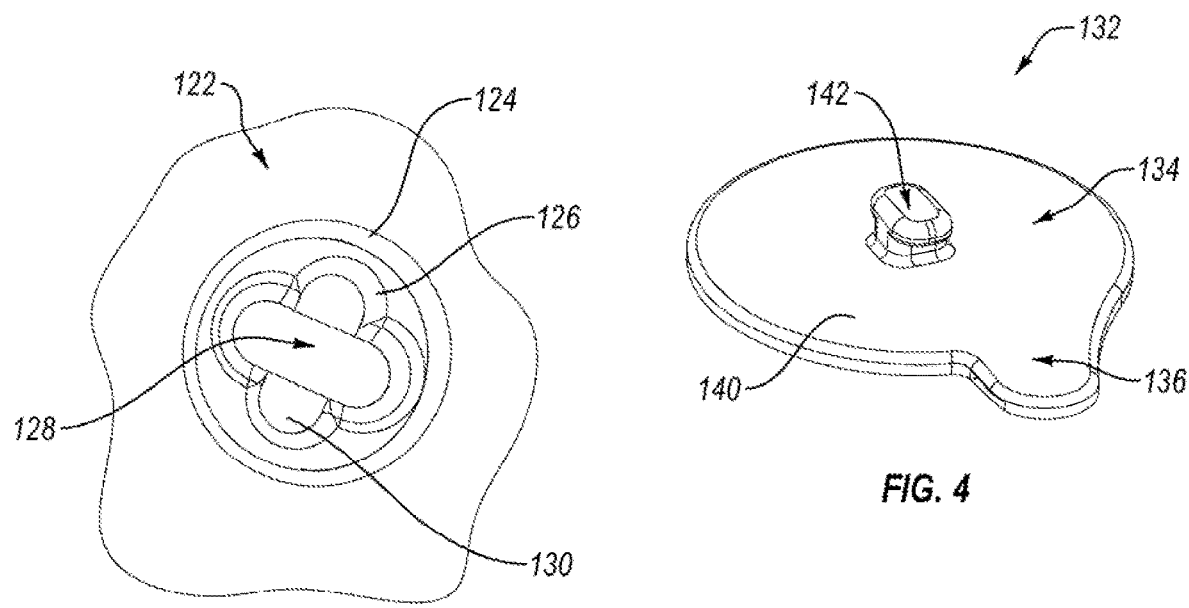
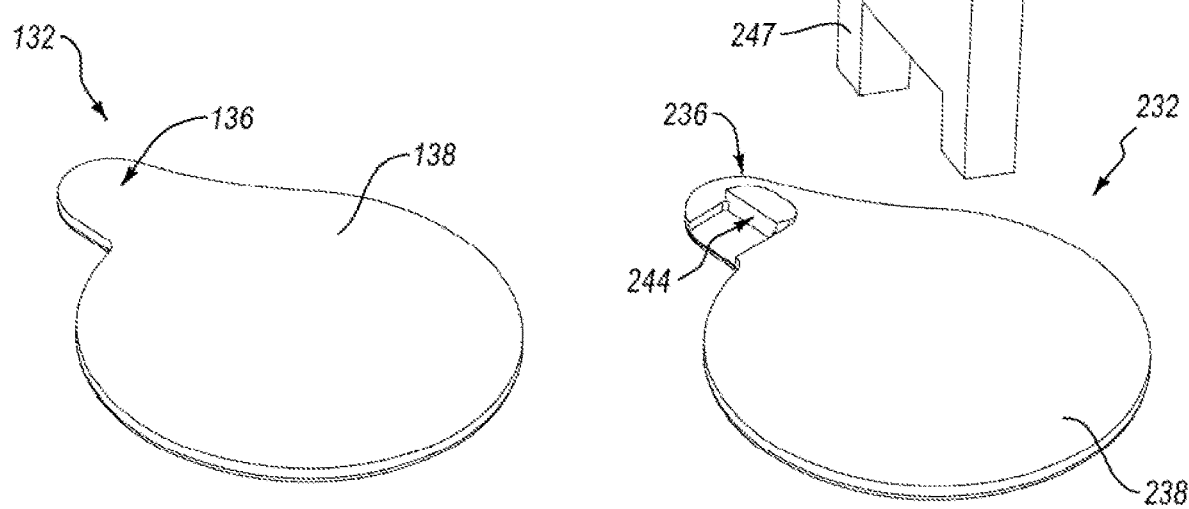

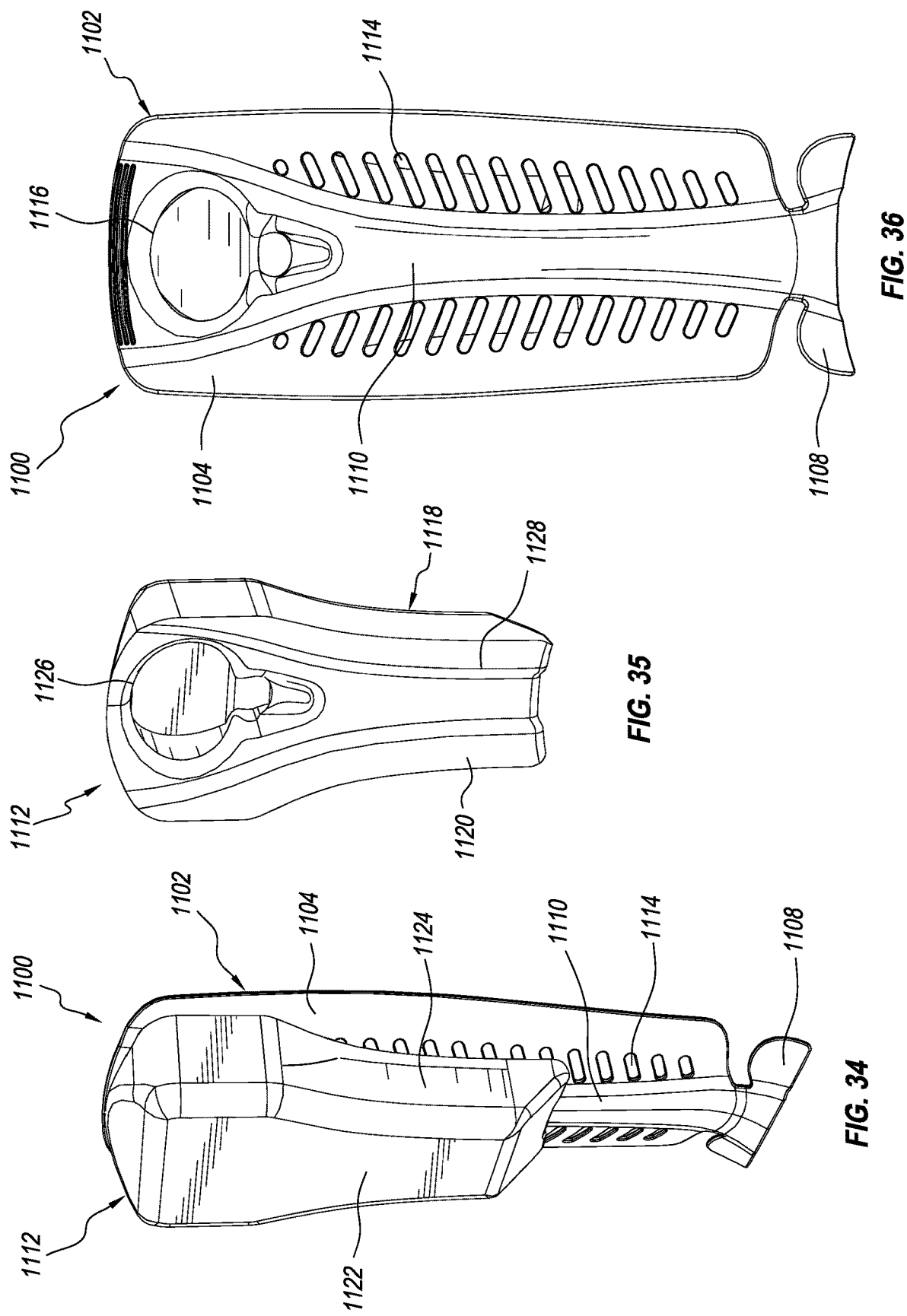

ORTHOPEDIC DEVICE

TECHNICAL FIELD

The disclosure relates to an orthopedic device for protecting and/or immobilizing one or more affected areas on a user's lower leg, ankle, and/or foot.

BACKGROUND

It is common that people, especially frail elderly people and diabetics, experience a variety of lower leg, ankle, and foot injuries. Physicians traditionally have treated, and still currently treat, injuries such as pressure ulcers affecting the foot by fitting the injured patient with the well-known, molded plaster or resin cast. The placement of this type of cast is time consuming, heavy, and costly. Further, this type of cast must not come into contact with water, which makes patient bathing difficult and time consuming. Additionally, if the cast needs to be removed for any reason, for example, inspection, a whole new cast must be prepared and applied.

Alternatively, walking boots or walkers have been used for protecting and immobilizing injured or affected areas of the lower leg, ankle, and/or foot, such that at least partial mobility may be maintained while the affected areas are in the process of healing. Further, in contrast to the molded plaster or resin cast, a walker can be easily removed in order to bathe or for inspection of the injured limb by a physician or practitioner.

Existing wrap-around or circumferential walkers however can be bulky and uncomfortable for users. Particularly, hard edges and/or surfaces of existing walkers can cause pressure points on the user's toes, feet, ankle, and/or lower leg that can cause users pain and discomfort, and may also cause injury to a user, such as pressure ulcers. Pressure ulcers can become infected, contain scar tissue, and may result in secondary problems up to and including amputation.

Alternatively, existing walkers may include inflatable supports for improving the comfort of the walker, but these inflatable supports can be more harmful than helpful. Particularly, existing walkers require the user to regulate or control the pressure level in the inflatable supports. This is problematic because patients, especially those with diabetes, often experience reduced sensation in their extremities, which can result in them inadvertently overinflating the inflatable supports. Over-inflation of the inflatable supports can cause pressure on the skin which can reduce both capillary blood flow to the skin and arterial flow to the affected limb. It can also lead to the formation of pressure ulcers on the foot of the patient and longer healing times for existing ulcers. Further, existing walkers with inflatable supports often require patients to monitor pressure levels in the inflatable supports with a pressure gauge. However, many patients do not see well enough to read the pressure gauges and such pressure gauges are also known to malfunction.

Additionally, features associated with the inflatable supports in existing walkers are known to create pressure points within the walker and/or to be unreliable. For instance, tubing associated with the inflatable supports is typically routed along the inside surface of the walker, creating pressure points on the inside of the walker, which can be uncomfortable and can cause additional pressure ulcers. Moreover, such tubing can become kinked and/or pinched between the walker and the patient's lower leg, ankle, and/or foot, rendering the inflatable supports effectively inoperable. Pump features associated with the inflatable supports are also commonly arranged on the walker such that they are prone to being bumped, misaligned, and/or damaged during use, increasing the likelihood that the inflatable supports will be inadvertently inflated, deflated, and/or rendered inoperable.

SUMMARY

The orthopedic device described herein may be, in exemplary embodiments, a lightweight walker. It is also contemplated that other orthopedic devices may utilize similar configurations as described below.

The orthopedic device described herein typically takes the form of a semi-rigid or substantially rigid shell walker, which provides protection and immobilization to an affected area on the lower leg, ankle, and/or foot by surrounding the lower leg, ankle, and/or foot with an appropriate structure. It will be recognized that the features described herein may have applicability to other walker configurations or other types of orthopedic devices.

In the exemplary embodiments, various configurations of flexible edge arrangements, inflation system arrangements, and shell arrangements are utilized to limit pressure points and/or excessive pressure on a user's lower leg, ankle, and/or foot in order to provide a more comfortable fit and more effective treatment of affected areas on the user's lower leg, ankle, and/or foot.

For example, an orthopedic device may include a base shell having ankle and foot receiving portions and forming an opening over a dorsal aspect of the base shell. A dorsal shell can be contoured to generally correspond to the opening in the base shell. The dorsal shell can include a proximal member connected to a distal member via a flexible or resilient connecting portion arranged to accommodate a portion of the user's lower leg or ankle.

A first flexible edge portion can be attached to a distal terminal end of the distal member. During use, the distal member of the dorsal shell can become pitched or angled relative to the user's toes due to a variety of different circumstances, including, but not limited to, user anatomy, use of heel lifts and/or wedges, or as the user walks. The first flexible edge portion can be arranged to flex or bend relative to the distal member when the distal member pitches or angles relative to the toes. This has the effect of reducing the transfer of force from the distal member to the toes and/or distributing the force from the distal member over a greater surface area, which, in turn, reduces the likelihood of a potentially harmful pressure point on the user's toes from the distal member.

The first flexible edge portion can also help accommodate bandaging of the user's toes or the forefoot because the first flexible edge portion can be flexed upward or removed from the distal member. The first flexible edge portion can also include a toe relief portion radially extending away from the user's toes, substantially reducing the likelihood of the distal member diving down into the toes, which could cause discomfort or even injury.

The proximal member of the dorsal shell may also include a second flexible edge portion attached to a proximal terminal end of the proximal member. The second flexible edge portion on the proximal member can be arranged to bend or flex when the user's leg exerts a force on the second flexible edge portion. This has the effect of reducing the likelihood of creating a pressure point on the user's lower leg from the dorsal shell and can provide pressure relief to the user's tibia, improving the comfort and effectiveness of the orthopedic device.

At least one observation hole may be formed in the base shell posterior of the user's malleoli to allow for tactile confirmation of the position of the user's foot within the orthopedic device, which can reduce the likelihood of one or more pressure points within the orthopedic device from the user's heel being too far back within the base shell.

By way of another example, an orthopedic device may include a base shell and a dorsal shell contoured to generally correspond to an opening in the base shell. At least one tightening member can be connectable to the base shell and extendable over the dorsal shell to secure the base shell and dorsal shell together about a user's lower leg and foot. At least one inflatable bladder may be provided in the base shell and a pump assembly may be arranged to inflate the at least one inflatable bladder.

The pump assembly can be situated on the at least one tightening member such that the position of the pump assembly is substantially fixed relative to the base shell as the user walks in the orthopedic device. This advantageously limits unwanted movement of the pump assembly, reducing the likelihood of the pump assembly inadvertently inflating or deflating the at least one inflatable bladder as in the prior art. The pump assembly may also be situated on an anterior aspect of the at least one tightening member, increasing the usability of the pump assembly.

The base shell can include at least one tube hole formed therein that allows at least one inflation tube to pass from the pump assembly to an exterior surface of the base shell such that the at least one inflation tube can run along the exterior surface of the base shell rather than the interior of the base shell as in the prior art. This has the effect of reducing the likelihood of a pressure point from the at least one inflation tube as the user walks in the orthopedic device and the likelihood of the at least one inflation tube being pinched or kinked inside of the orthopedic device.

A pressure relief valve assembly can be fluidly connected to the at least one inflatable bladder and arranged to automatically release air from the at least one inflatable bladder to atmosphere when pressure within the at least one inflatable bladder exceeds a cracking pressure of the pressure relief valve assembly. This allows the pressure relief valve to automatically regulate or limit the pressure level within the at least one inflatable bladder rather than requiring the user to regulate the pressure level, as in the prior art, eliminating or substantially decreasing the likelihood that a user will over-inflate the at least one inflatable bladder. This is advantageous because users of walkers and other orthopedic devices, especially diabetic patients, often experience reduced sensation in their extremities, which can result in them inadvertently over-inflating the at least one inflatable bladder. Such over-inflation can cause pressure on the skin, which can reduce both capillary blood flow to the skin and arterial flow to the anatomical member. It can also lead to the formation of pressure ulcers on the foot of the patient and longer healing times for existing ulcers.

Further, because the pressure relief valve automatically regulates pressure within the at least one inflatable bladder, users can inflate the at least one inflatable bladder without the need of reading a pressure gauge as in the prior art, making the orthopedic device easier and safer to use. The pressure relief valve assembly also overcomes issues with changes in ambient pressure creating excessive pressure within the at least one inflatable bladder, such as a change in altitude, as the pressure relief valve assembly automatically reduces excess pressure in the at least one inflatable bladder.

BRIEF DESCRIPTION OF THE DRAWINGS

These and other features, aspects, and advantages of the present disclosure will become better understood regarding the following description, appended claims, and accompanying drawings.

FIG. 3 is a detail view of an eyelet shown in FIG. 2 according to an embodiment.

FIG. 4 is a front isometric view of a hook tab component according to an embodiment.

FIG. 5 is a back isometric view of the hook tab component shown in FIG. 4.

FIG. 6 is a back isometric view of the hook tab component and a tightening tool according to another embodiment.

FIG. 34 is a front isometric view of an orthopedic system according to another embodiment.

FIG. 35 is a back isometric view of the protective part in FIG. 34 removed from the dorsal shell for ease of reference.

FIG. 36 is a back isometric view of the dorsal shell in FIG. 34.

DETAILED DESCRIPTION OF VARIOUS EMBODIMENTS

Figure 1:
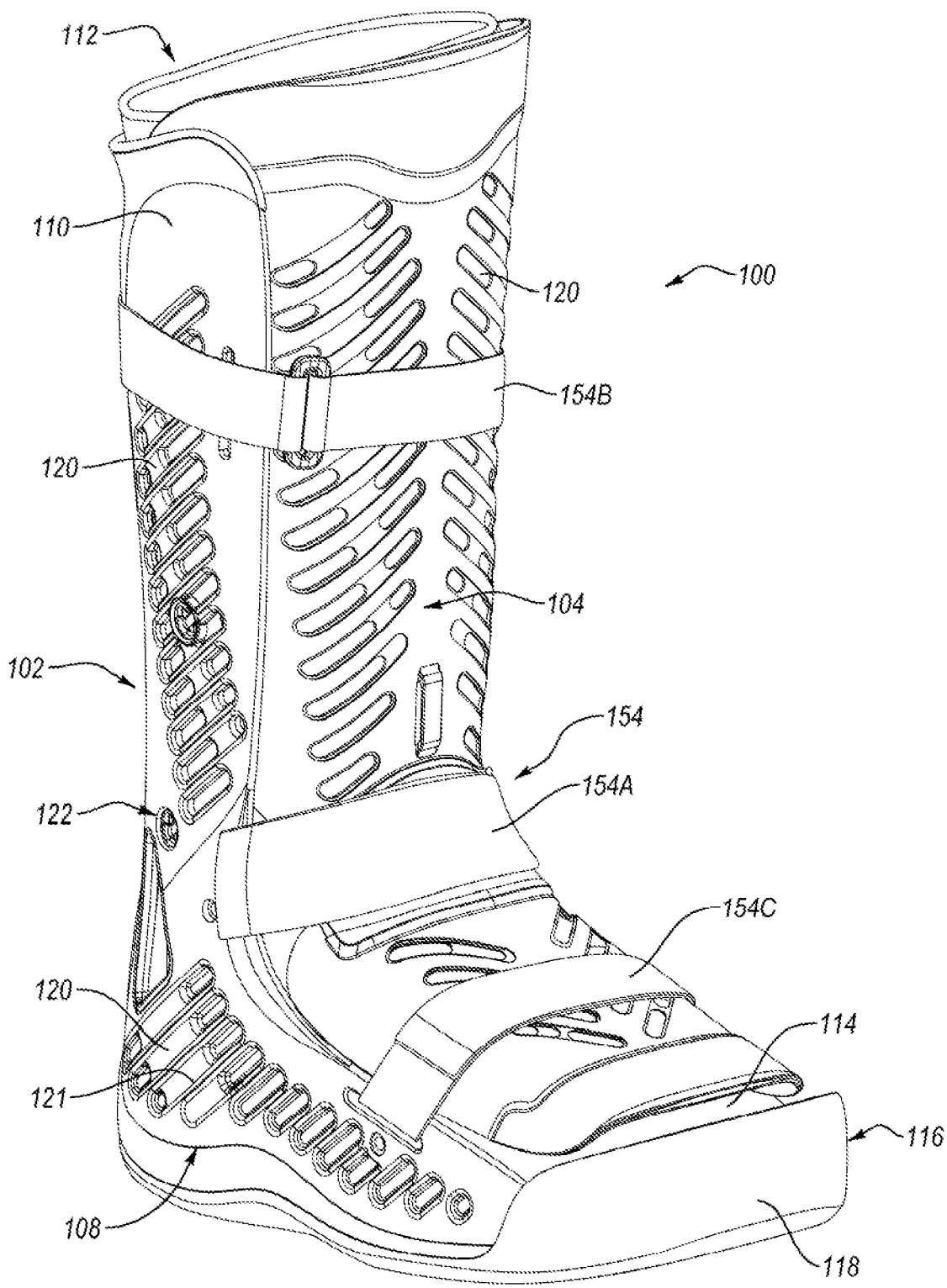
FIG. 1 is a front side isometric view of an orthopedic device comprising a walker according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and described below. It should be understood, however, there is no intention to limit the disclosure to the embodiments disclosed, but on the contrary, that the intention covers all modifications, alternative constructions, combinations, and equivalents falling with the spirit and scope of the disclosure.

For further ease of understanding the embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing; however such support members or shells may have some degree of flexibility or resiliency.

An exemplary embodiment of a walker 100 is shown in FIGS. 1-9. As can be seen from the figures this embodiment includes complementary base 102 and dorsal 104 shells that are selectively engageable with each other in order to provide easy access to the interior of the device for ease of donning and doffing the device, in particular for donning and doffing the device unto an injured limb. The base shell 102 has ankle and foot receiving portions 101, 103 (best shown in FIG. 7) and forms an opening 105 (best shown in FIG. 7) over a dorsal aspect thereof. The dorsal shell 104 is contoured to generally correspond to the opening 105 of the base shell 102.

The walker 100 can include a semi-rigid or substantially rigid shell configuration that is formed to support and support the lower leg, foot, and ankle of the user or patient. The shell configuration can extend from the foot and ankle up along the shin and tibia of the lower leg to a desired point below the knee joint. Exemplary suitable materials for forming the shells can include metals, such as aluminum, carbon, composites, glass fiber/epoxy composites, or suitable plastic materials, such as thermoplastic or thermosetting polymers, fiber reinforced plastic, molded chopped fibers, or any other suitable material. Other exemplary materials include, but are not limited to, nylons, glass filled nylon, polypropylenes, vinyls, polyvinyl chlorides, high density polyethylene, epoxies, urethanes, and polyesters. While the walker is described having a rigid shell configuration, it will be appreciated that the walker 100 may be any type of walker or other suitable orthopedic device.

In use, a user can move the walker 100 from a closed configuration to an open configuration by moving the dorsal shell 104 away from the base shell 102, allowing insertion of the lower leg, ankle, and foot into the walker 100. Once the user has inserted their lower leg into the walker 100, the dorsal shell 104 can be returned to the closed configuration to enclose the lower leg within the walker 100. The user can then utilize one or more tightening mechanisms described below to apply pressure and support and to maintain the walker 100 in the closed configuration.

The walker 100 can be oversized to accommodate a number of different accessory components and/or sized feet. A width of the walker 100 can be defined between the lateral and medial sides of the walker 100. The width of the walker 100 can be between about 1.02 and about 1.5, between about 1.05 and about 1.3 (e.g., about 1.08), or between about 1.1 and about 1.2 times greater than the width of a conventional walker. For instance, if a conventional walker has a width of about 140 mm, the walker 100 can have a width between about 145 mm and about 160 mm (e.g., about 152 mm). This has the effect of providing a larger foot bed within the walker 100 for insertion of accessory components, such as, but not limited to, heel wedges, inflatable bladders, padding, or other suitable components. This also allows the walker 100 to accommodate larger feet and/or to be a multi-purpose walker. For instance, the oversized foot bed can provide sufficient space to add and/or remove components from the walker 100, allowing the walker 100 to be customized for a specific purpose. More particularly, by adding and/or removing components from the foot bed of the walker 100, the walker 100 can be converted from one type of walker to another type of walker (e.g., from a diabetic walker to an Achilles walker, or a fracture walker, or vice versa).

The shell configuration includes a base shell 102 and a dorsal shell 104. At least one of the base shell 102 or the dorsal shell 104 can have generally smooth rounded edges, helping to increase the comfort and safety of the walker 100. The base shell 102 has a posterior portion 106 (best shown in FIG. 2) and a plantar portion 108 that is arranged to extend along the plantar surface of the foot. Lateral and medial (first and second) wing portions 110 extend from the posterior portion 106 and the plantar portion 108. The wing portions 110 can be arranged to at least partially enclose and support a user's leg. A soft good liner 112 can be situated inside the base shell 102. An insole 114 can be provided on the proximal surface of the liner 112 and/or the base shell 102. An outsole 116 is formed on the base shell 102, either integrally, or separately. The outsole 116 can define a toe protector portion 118 and can have any suitable configuration, such as a rubber sole having a roll over shape.

In order to reduce the weight of the walker 100 and/or to provide ventilation, material can be removed from areas of the shell portions to provide apertures 120. The apertures 120 can be formed in any of the shells 102, 104. The apertures 120 can have different sizes and/or shapes. The apertures 120 can extend at an angle. For instance, some of all of the apertures 120 can have a generally oblong shape and can extend at an angle. The apertures 120 in the ankle region of the base shell 102 can be longer than the apertures 120 in a toe region of the base shell 102.

Some or all of the apertures 120 can be arranged in one or more gradients. Arranging the apertures 120 in gradients can improve the biomechanical properties of the shells with respect to an anatomical limb positioned in the walker 100 by influencing the flexibility or stiffness of the shells with the apertures. For instance, the apertures 120 in the foot receiving portion 103 of the base shell 102 can be arranged in a gradient with larger apertures 120 in the ankle region and smaller apertures in the toe region. The apertures 120 in an upper region of the base shell 102 can be arranged with larger apertures 120 toward the middle of the lower leg and smaller apertures 120 toward the ankle and the knee.

In other embodiments, the apertures 120 in the upper region of the base shell 102 can have different sizes and shapes and can be extending at an angle. Some or all of the apertures 120 can also be arranged in a plurality of rows. Some or all of the apertures 120 in the foot receiving portion 103 of the base shell 120 can comprise a series of slots extending at an angle and a singular larger, irregularly shaped non-through hole in the toe region.

The apertures 120 can comprise through holes and/or non-through holes. Some or all of the apertures 120 in the foot receiving portion 103 of the base shell 102 can be non-through holes. This can prevent ingress of external objects through the apertures 120 that may potentially injure the foot, which, in turn, enhances user safety. This also has the effect of protecting the user's foot from sharp edges that can injure the foot. The non-through holes in the foot receiving portion 103 are especially important for users of the walker 100 who suffer from neuropathy having nerve damage in the foot. Non-through holes in either shell can also reinforce or strength the walker 100 in the region of the apertures 120.

Some or all of the apertures 120 can comprise through holes. Some or all of the through holes can be positioned, shaped, sized, and/or patterned to enhance heat and/or fluid transfer from the interior of the walker 100 to the exterior of the walker 100. This can allow the walker 100 to vent heat and/or perspiration from the interior of the walker 100, which, in turn, increases user comfort. The through-holes can also provide some level of resiliency to the shells. This can allow the walker 100 to better accommodate swelling of a limb or different sizes of lower legs, ankles, and/or feet.

Some or all of the apertures 120 can include a through-hole portion and a non-through hole portion. For instance, some or all of the apertures 120 can include a periphery and upstanding sidewall portions extending about the periphery. A non-through hole portion can include a bottom surface formed by a portion of the shell and a through-hole portion can be open ended, extending completely through the shell.

Some or all of the apertures 120 can include radiused or rounded-off edges, reducing the likelihood of a user inadvertently scrapping or injuring a non-affected limb on the edges of the apertures 120 as the non-affected limb moves back and forth across the apertures.

The walker 100 can have structures designed to selectively strengthen the base shell 102 and the dorsal shell 104 in a specific direction. The base shell 102 can include reinforcing ridges 121 that extend at an angle along both lateral and medial sides thereof.

Figure 2:
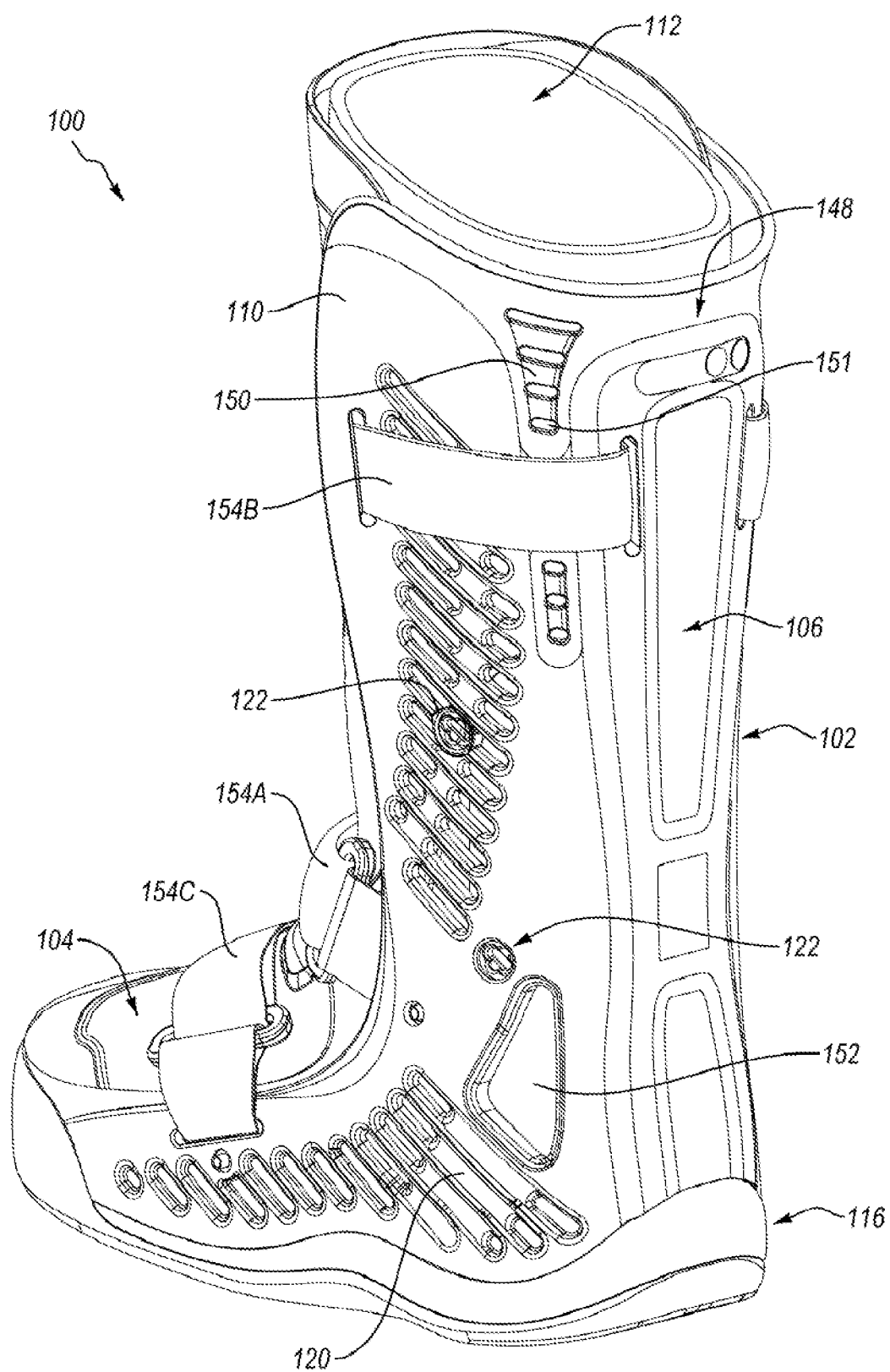
FIG. 2 is a back side isometric view of the walker shown in FIG. 1.

As can be seen in FIGS. 1 and 2, eyelets 122 can be formed in the wing portions 110 of the base shell 102 for providing one or more anchoring points for different components and/or accessories. FIG. 3 is a detailed view of an eyelet 122 according to an embodiment.

The eyelet 122 can include an annular rim portion 124, a sloping inner sidewall portion 126, a through-hole portion 128, and a seat 130 formed in the inner sidewall portion 126 for receiving and securing a portion of an attachment system (e.g., a hook portion) therein. The eyelets 122 can be at least partially debossed below an exterior surface of the base shell 102 such that each eyelet 122 is at substantially the same depth below the exterior surface.

Some or all of the eyelets 122 can provide an anchoring a point for a hook tab component, such as the hook tab component 132 shown in FIGS. 4 and 5. As seen, the hook tab component 132 can comprise a larger generally elliptical main body 134, a smaller portion 136, a generally planar bottom side 138, and an upper side 140. The hook tab component 132 can be formed from any suitable material such a plastic, rubber, or metal material.

The bottom side 138 of the hook tab component 132 can arranged to provide an attachment surface for a portion of a hook-and-loop type system (e.g., Velcro®), the liner 112, a pad, an inflatable bladder described below, or any other suitable component. The attachment surface can be used to place an adhesive dot or two sided tape on the hook tab component 132. For instance, a pad could be adhered to the bottom side 138 of the hook tab component 132 via the adhesive dot or two sided tape and then secured in a fixed position on the walker 100 as desired.

A hook member 142 can be formed on the upper side 140 for interfacing with an eyelet 122. The hook member 142 can exhibit any suitable configuration. The hook member 142 can include a generally rectangular base portion attached to the upper side 140 and a generally oblong head portion attached to the rectangular base portion.

The hook member 142 can anchor the hook tab component 132 to the base shell 102. The hook tab component 132 can be situated inside the walker (shown in FIG. 7) and the head portion of the hook member 142 can be generally aligned with the through-hole portion 128 in the eyelet 122. The head portion of the hook member 142 can then be inserted through the through-hole portion 128 and rotated until the head portion of the hook member 142 rests in the seat 130 of the eyelet 122, which secures the hook tab component 132 within the eyelet 122. While secured in the eyelet 122, the upper side 140 of the hook tab component 132 can be facing and/or secured against the interior surface of the base shell 102. This allows the location of components inside of the walker 100 to be customized by installing hook tab components 132 attached or attachable to the components in different eyelets 122 formed in the base shell 102.

Optionally, the hook tab component 132 can include installation features to aid in the installation of the hook tab component in the eyelet 122. FIG. 6 illustrates a hook tab component 232 according to another embodiment including a recessed portion 244 formed in the bottom side 238 of the smaller portion 236.

A user can insert a tightening tool 246 or key within the recessed portion 244 to rotate the hook tab component 232 within the eyelet 122 relative to the base shell 102. A first portion of the tightening tool 246 can be positioned on the bottom side 238 at or near a center of the hook tab component 232. A protrusion 247 on the tightening tool 246 can be positioned in the recessed portion 244. The tightening tool 246 can then be rotated about the first portion on the center of the hook tab component 232, which, in turn, causes the protrusion to engage a shoulder formed by the recessed portion 244, rotating the hook tab component 232. This can facilitate installation of the hook tab component 232 in the eyelet 122. Requiring the use of the tightening tool 246 can help deter a patient or user from removing or moving the hook tab components 232, and thereby components attached thereto, from the walker 100 without the consent of a clinician or medical professional. The tightening tool 246 can also be provided to the clinician or medical professional but not the user or patient, helping to prevent tampering.

Referring again to FIG. 2, a flexible or resilient edge portion 148 and expansion joints 150 can be formed on the posterior portion 106 of the base shell 102 along the edges of and between the posterior of the wing portions 110. The expansion joints 150 can be arranged in discrete groupings and formed having a larger dimension at the proximal end and tapering down to a smaller dimension at the distal end. The expansion joints 150 can include any number of expansion holes 151 passing therethrough. The expansion holes 151 can be arranged in any suitable manner and can have any desired shape or size.

Some or all of the expansion joints 150 and/or the flexible edge portion 148 can be formed via overmolding a different material onto end portions of the base shell 102. For instance, the flexible edge portion 148 can be formed via a flexible plastic or elastomer, such as, for example, thermoplastic elastomer (TPE), rubber, or ethylene vinyl acetate (EVA) foam. In other embodiments, any other suitable material may be utilized, including silicone or natural or synthetic fibers. Overmolds and overmolding techniques are described in more detail in U.S. Pat. No. 5,951,504, granted Sep. 14, 1999, U.S. Pat. No. 7,018,351, granted Mar. 28, 2006, U.S. Pat. No. 7,288,076, granted Oct. 30, 2007, U.S. Pat. No. 7,311,686, granted Dec. 25, 2007, and U.S. Pat. No. 8,002,724, granted Aug. 23, 2011, all of which are incorporated herein, in their entirety, by this reference.

One or more observation holes 152 are formed in the wing portions 110 of the base shell 102 in the ankle receiving portion 101, allowing for easy observation of the position of the user's foot within the walker 100 and/or observation of the operation of one or more inflatable bladders within the walker 100. The observation holes 152 can exhibit any suitable configuration. The observation holes 152 can comprise generally rounded triangular through-holes positioned posterior to the malleoli in the base shell 102. The position, size and shape of the observation holes 152 can be arranged for tactile confirmation of the position of the foot within the walker 100. Using the observation holes 152 a clinician, medical professional, or user can confirm that the heel of the user is properly positioned within the walker 100, which, in turn, reduces the likelihood of pressure points within the walker 100 from the heel being too far back.

Wounds in the ankle region of the user's foot can be observed via the observation holes 152 without the need of removing the walker 100 from the foot, increasing the convenience of the walker 100. The observation holes 152 can also allow for tactile and/or visual confirmation that inflatable bladders positionable inside the base shell 102 are properly inflating or inflated, decreasing the likelihood of improper inflation.

While the observation holes 152 are described as generally triangular, it will be appreciated that the observation holes 152 can be generally circular, generally oval, generally diamond, or any other suitable shape. Further, while two observation holes are shown, in other embodiments, the walker 100 can include one, three, four, or any other suitable number of observation holes. The observation holes 152 can also be formed in any portion of the walker 100.

Figure 7:
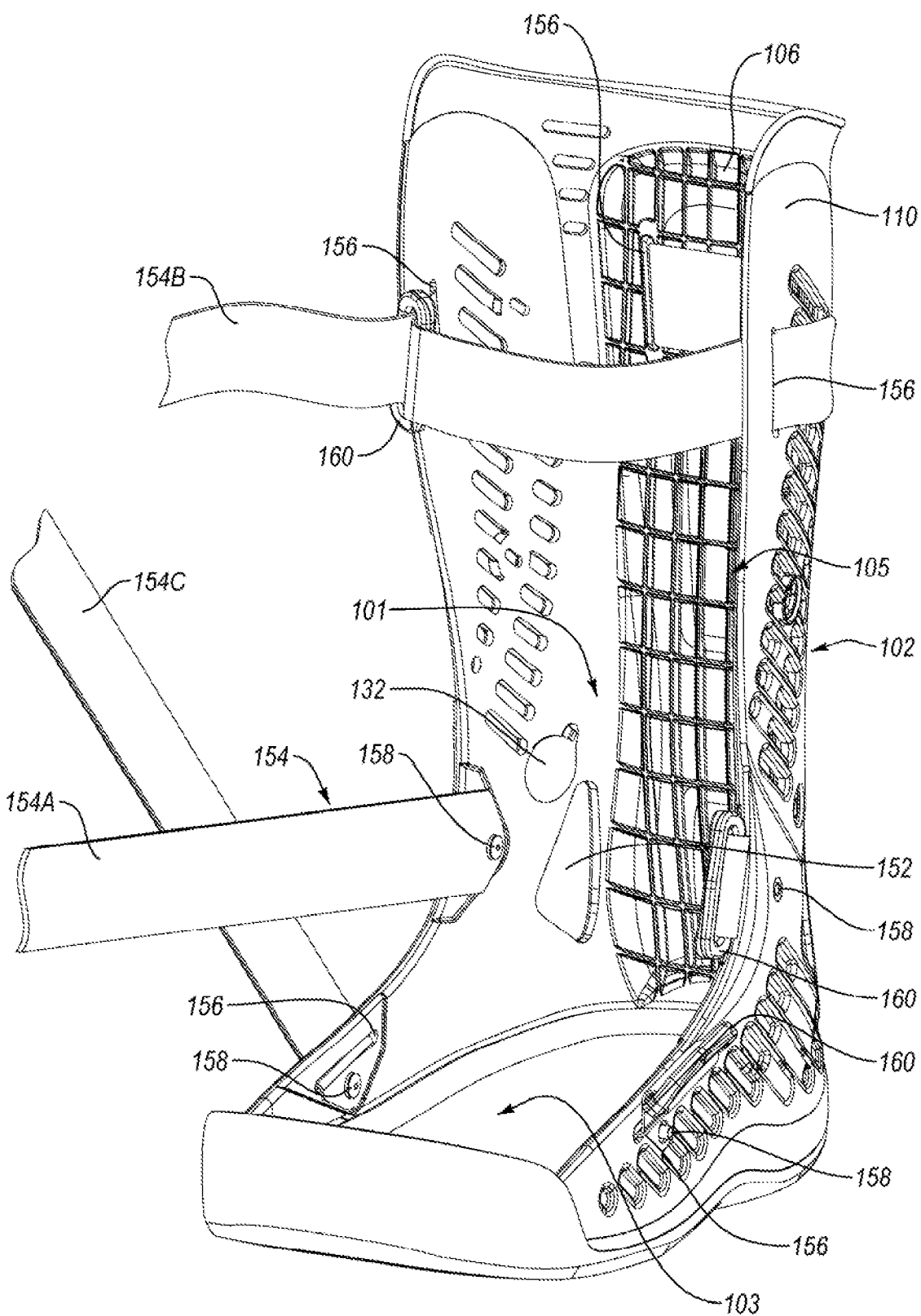
FIG. 7 is a front side isometric view of the base shell shown in FIG. 1.

As best seen in FIGS. 1, 2 and 7, a plurality of tightening mechanisms 154 can be arranged to bring the base shell 102 and the dorsal shell 104 closer together for tightening the walker 100 around the lower leg, ankle, and the foot. The plurality of tightening mechanisms 154 can include an ankle strap 154A, an upper strap 154B, and a foot strap 154C.

The ankle strap 154A can be arranged to cross over the ankle and to substantially fix the position of the ankle relative to the walker 100. The upper strap 154B can be arranged to cross over the lower leg below the knee. The upper strap 154B in concert with the ankle strap 154A can substantially fix the position of the lower leg relative to the base shell 102 by forming at least two anchoring points, one over the ankle and the other below the knee. The foot strap 154C can be arranged to cross over the dorsal aspect of the foot. The foot strap 154C in concert with the ankle strap 154A can substantially fix the position of the foot relative to the base shell 102 by forming at least two anchoring points, one over the ankle and one over the distal aspect of the foot. The arrangement of the straps 154 help to keep the foot and/or ankle from moving around in the foot bed of the walker 100 reduces the likelihood of sores forming on the plantar surface of the foot, ankle, and/or lower leg from unwanted movement of the same within the walker 100.

The straps 154 can comprise any suitable material. The straps 154 can include woven materials, cotton, foam, rubber, nylon, polyesters, neoprene, vinyl, webbing, or any other suitable material. The straps 154 can include any suitable type of fastening system. The straps 154 can include corresponding hook-and-loop fasteners so that at least an end portion of the straps 154 can connect a strap 154 to itself. A loop or D-ring can be attached to one end portion of the strap 154, allowing the strap 154 to be looped through the loop or D-ring and attaching to itself via any suitable fastener.

A plurality of strap slots 156 can be formed in the wing portions 110 and the posterior portion 106 of the base shell 102 for receiving and positioning the straps. Strap connecting portions 158 can be provided on the wing portions 110 for anchoring the straps 154 on the base shell 102. The strap connecting portions 158 can comprise reduced thickness portions, holes for rivet connections, or other suitable structure. If holes or rivet connections are used, connections points for the straps 154 can be pivotable. For instance, an end portion of some or all of the straps 154 can include one or more grommets arranged to receive one or more rivets, forming a riveted connection between the strap and the base shell 102, allowing the strap to rotate at least some degree relative to the base shell 102.

A loop or D-ring 160 can be attached to one end of the upper strap 154B. The upper strap 154B can be threaded through the strap slots 156 on the wing portions 110 of the base shell 102 and the strap slots 156 on the posterior portion 106 of the base shell 102. The upper strap 154B can then be looped through the loop or D-ring 160 and attached to itself, securing the upper strap 154B over the dorsal shell 104.

Loops or D-rings 160 are attached via loops of fabric that are attached to the strap connecting portions 158 on one of the wing portions 110 in the foot receiving portion 103 via loops of fabric. Each of the ankle strap 154A and the foot strap 154C can be connected at one end to the strap connecting portions 158 on the opposite wing portion 110. To fasten the ankle strap 154A and the foot strap 154C over the dorsal shell 104, the straps 154A, 154C can be extended across the dorsal shell 104 and free ends thereof can be looped through the loops or b-rings 160 on the opposite wing portion 110. Each of the ankle strap 154A and the foot strap 154C can then be connected to itself via any suitable fastener, such as hook-and-loop fasteners. Alternatively, the loops or D-rings in the foot and/or ankle region can be omitted. For instance, the ankle strap 154A and the foot strap 154C can be attached to the wing portions 110 via strap slots formed in the wing portions 110.

Strap slots 156 can be formed medial and lateral of the foot receiving portion 103 in the base shell 102. The foot strap 154C and the connection of the loop or D-ring 160 in this region pass from the strap connecting portions 158 on the interior of the base shell 102 through these strap slots 156 to the exterior of the base shell 102, situating the foot strap 154C on the outside of the base shell 102. The foot strap 154C can thus be accessible on the exterior of the base shell 102 rather than the interior of the base shell 102, as in the prior art. This allows a user to more easily locate and/or thread the foot strap 154C through the loop or D-ring 160 and reduces the likelihood of the foot strap 154C failing inside of the walker 100, making the walker 100 easier to don and doff. Further because the foot strap 154C is on the outside of the base shell 102, the likelihood of pressure points forming along the dorsal surface of the user's foot from the foot strap 154C is significantly reduced, making the walker 100 safer and more comfortable to wear.

The number and configuration of the straps 154 is to be regarded as exemplary only, as any suitable number and/or configuration of tightening mechanisms is possible. For instance, the walker 100 can include two, four, or any other suitable number of straps. In place of straps, other suitable tightening mechanisms, such as buckles or quick connecting strap mechanisms can be utilized.

Figure 8A:
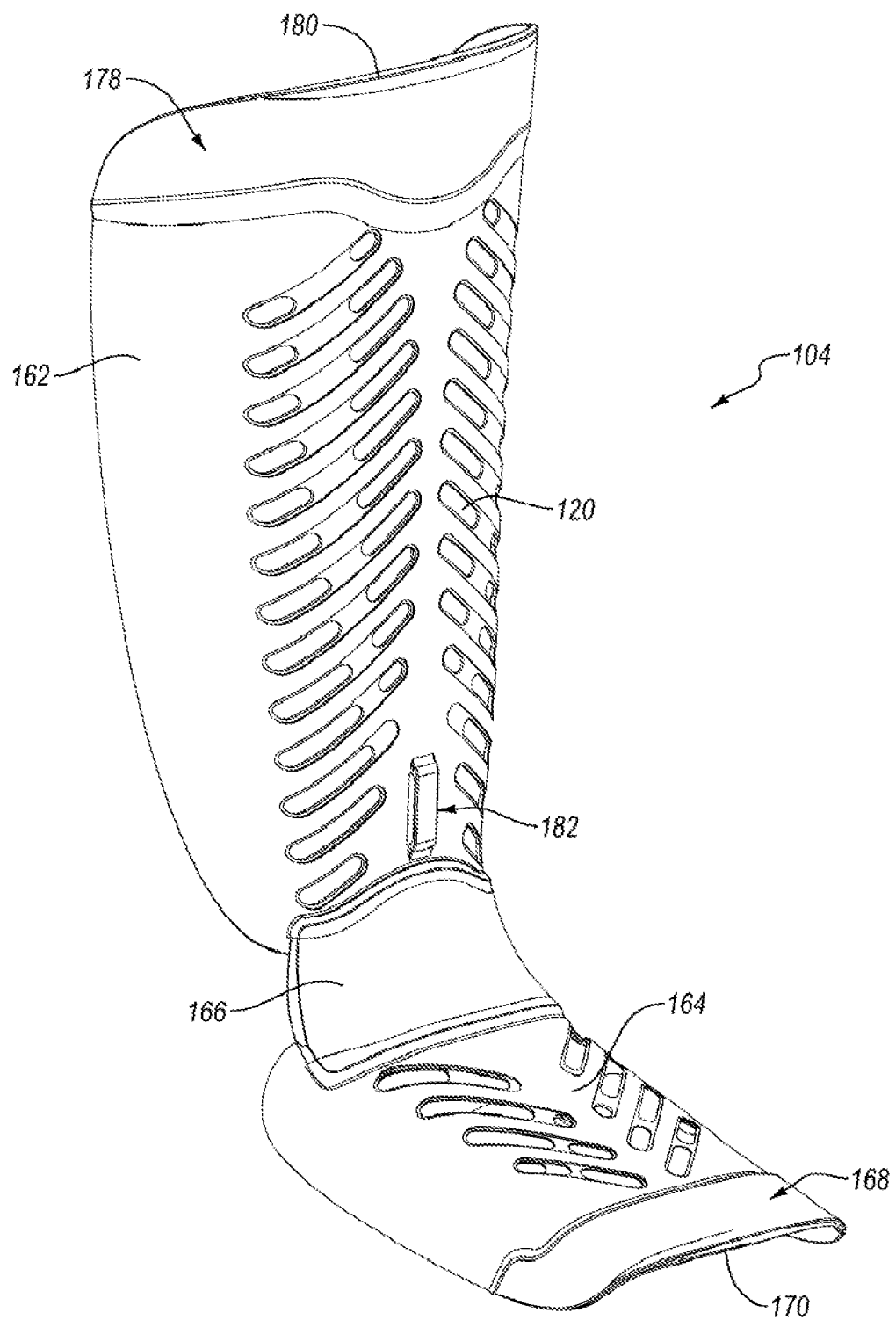
FIG. 8A is a front side isometric view of the dorsal shell shown in FIG. 1.
Figure 8B:
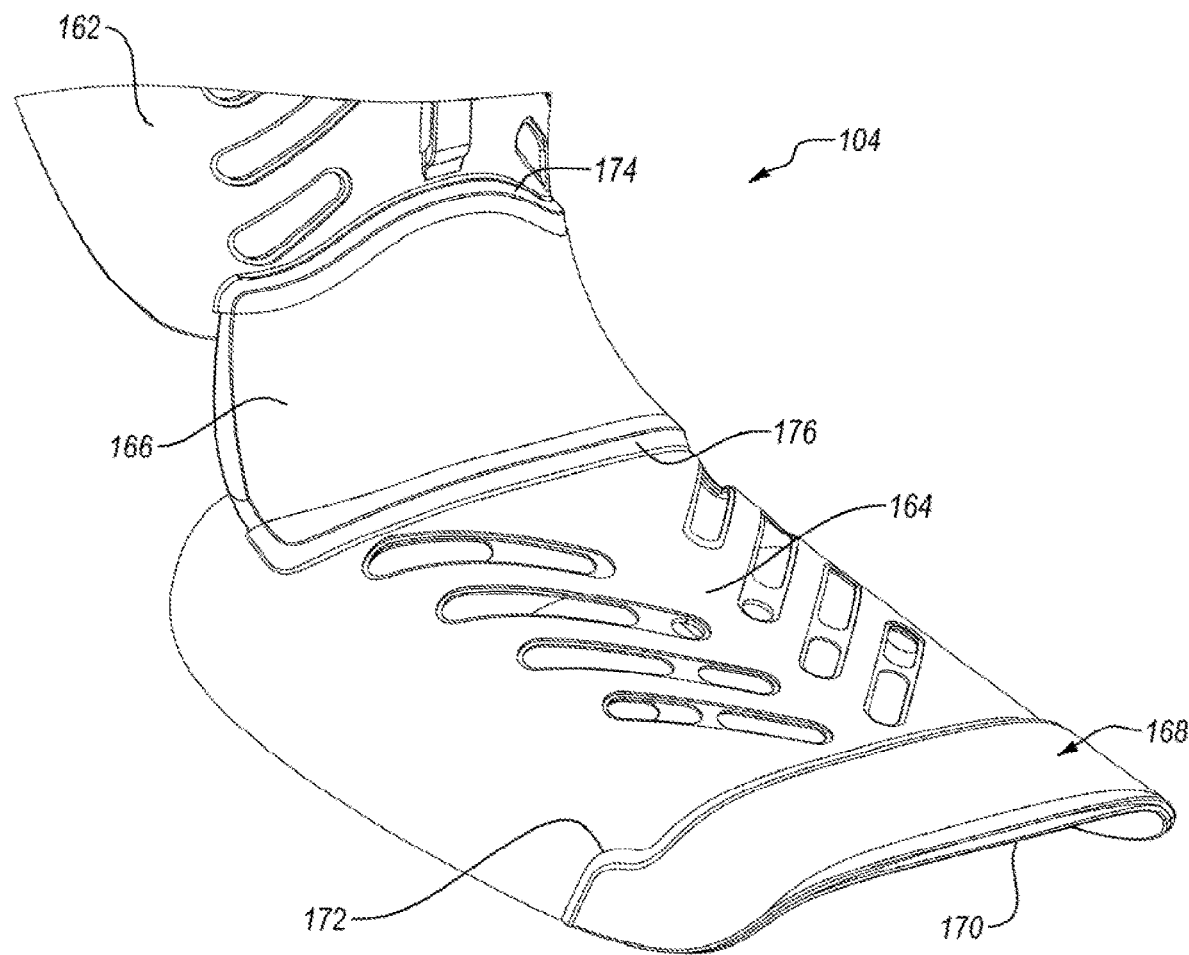
FIG. 8B is a partial front side isometric view of the dorsal shell shown in FIG. 8A.
Figure 9:
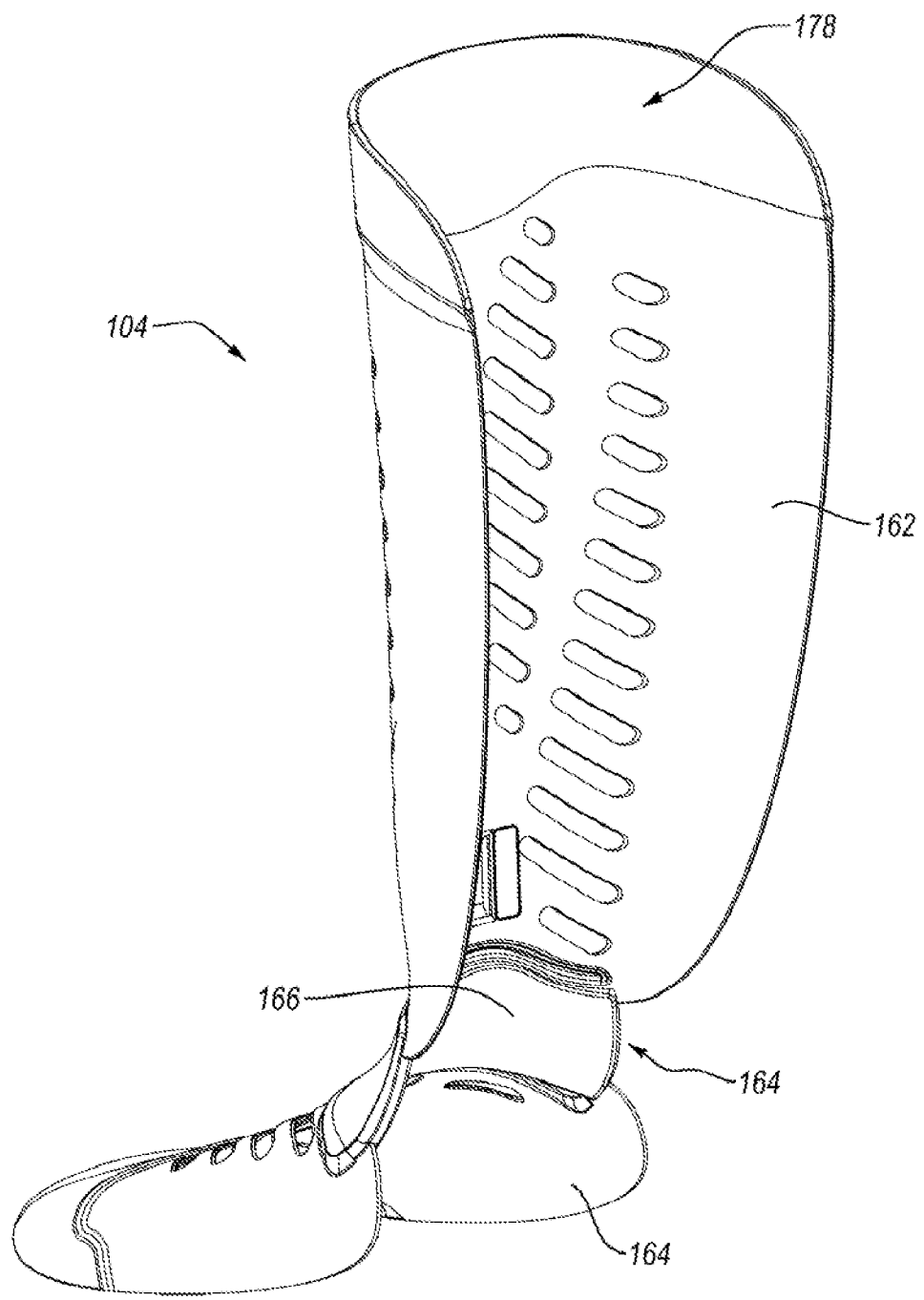
FIG. 9 is a back side isometric view of the dorsal shell shown in FIG. 1.

Referring to FIGS. 8A-9, the dorsal shell 104 can be formed either in a single piece or in multiple portions. The dorsal shell 104 can include a proximal member 162 and a distal member 164 connected to the proximal member 162 via a flexible or resilient connecting portion 166. A plurality of apertures 120 are formed in the distal member 164 of the dorsal shell 104. The apertures 120 can be slanted and can include a generally oblong periphery. The apertures 120 can be arranged in a first column on one side of a longitudinal axis of the distal member 164 and a second column on the opposite side of the longitudinal axis. Some or all of the apertures 120 can have rounded or curved edges, protecting an unaffected limb from being scratched or cut by the edges of the apertures 120.

Some or all of the apertures 120 in the distal member 164 can be non-through holes, preventing ingress of external objects (e.g., debris, gravel, sand) through the apertures 120 that could injure the foot of the user. The non-through holes can further help protect the foot from sharp edges and/or objects. It will be appreciated that some or all of the apertures 120 in the distal member 164 can be through-holes or omitted.

A flexible edge or flexible toe portion 168 can be attached to a distal terminal end of the distal member 164 for reducing the likelihood of pressure points from the dorsal shell 104 in the toe region of the user's foot. The flexible toe portion 168 extends between the medial and lateral sides of the distal member 164. The flexible toe portion 168 can include a periphery, an upper surface area, a distal sidewall portion, and a proximal sidewall portion extending from the upper surface area. The flexible toe portion 168 can be formed of any suitable material. The flexible toe portion 168 can be formed of a flexible plastic or elastomer, such as for example, rubber or EVA foam. Other suitable materials may include silicone or natural or synthetic fibers.

During use, the dorsal shell 104 can become pitched or angled relative to the user's toes, forcing the distal member 164 and the flexible toe portion 168 onto the toes. The distal member 164 can become pitched or angled relative to the toes due to a variety of different circumstances. For instance, the distal member 164 can become pitched or angled relative to the toes by user anatomy (e.g., high instep) or with the use of heel lifts and/or wedges. By way of another example, the distal member 164 can become pitched or angled relative to the toes as the user walks.

As the distal member 164 pitches or angles relative to the user's toes, the flexible toe portion 168 can bend or flex relative to the distal member 164. This has the effect of reducing the transfer of force from the distal member 164 to the toes and/or distributing the force from the distal member 164 over a greater surface area, which, in turn, reduces the likelihood of pressure points forming on the toes from the distal member 164. The flexible toe portion 168 can also help accommodate bandaging of the toes or the forefoot because the flexible edge portion can be flexed upwards, cut, and/or removed from the distal member 164. The arrangement of the flexible toe portion 168 also provides a barrier over the toes, protecting the toes from external objects and/or sharp edges.

Optionally, a toe relief portion 170 of the flexible toe portion 168 can angle, curve upward, and/or radially extend away from the user's toes, spacing the toe relief portion 170 a distance away from the toes and/or creating an axis other than the toe relief portion 170 about which the flexible toe portion 168 can flex. This has the effect of reducing the likelihood of pressure points on the user's toes from the flexible toe portion 168. In addition, if the flexible toe portion 168 is forced downward onto the toe protector portion 118 (shown in FIG. 1) of the outsole 116, the upward angle of the toe relief portion 170 can allow the flexible toe portion 168 to move up and away from the user's toes rather than diving down into the toes, which could cause discomfort or even injury. The toe relief portion 170 can bend back away from the toes and toward an upper surface of the distal member 164. The upward angle of the edge portion 168 also can help create additional space to accommodate the user's toes.

The flexible toe portion 168 can be attached to the distal member 164 of the dorsal shell 104 in any suitable manner. The flexible toe portion 168 can be overmolded on a distal edge of the distal member 164 with alternating and/or intermeshing portions of the flexible toe portion 168 and distal member 164 mechanically fastening the flexible toe portion 168 and the distal member 164.

As best seen in FIG. 8B, a ridge portion 172 can be formed on an upper surface of the distal member 164 for increasing the attachment strength between the flexible toe portion 168 and the distal member 164. The ridge portion 172 can extend at least in part between the lateral and medial sides of the distal member 164 adjacent the flexible toe portion 168. The ridge portion 172 can be elongated, having a proximal sidewall portion, a distal sidewall portion, and an upper surface area extending between the proximal and distal sidewall portions. The ridge portion 172 can increase the attachment surface area between distal member 164 and the flexible toe portion 168.

The flexible toe portion 168 can be attached to both the distal sidewall portion and the upper surface area of the ridge portion 172, increasing the connection surface area between the distal member 164 and the flexible toe portion 168, which, in turn, increases the connection strength between the flexible toe portion 168 and the distal member 164.

The distal sidewall portion of the ridge portion 172 can physically block the foot strap 154C (shown in FIG. 1) from sliding onto the flexible toe portion 168, increasing the protection of the user's toes. The ridge portion 172 preventing or limiting movement of the foot strap 154C can also reduce the likelihood of the dorsal shell 104 being prematurely worn down by a migrating foot strap 154C. The ridge portion 172 further can reinforce the flexible toe portion 168. For instance, if the flexible toe portion 168 is forced into the toe protector portion 118 (shown in FIG. 1) of the outsole 116, the distal sidewall portion of the ridge portion 172 can support the proximal sidewall portion of the flexible toe portion 168 against shear or other forces that could potentially cause the flexible toe portion 168 to tear away from the distal member 164 of the dorsal shell 104. In other embodiments, the flexible toe portion 168 can be omitted.

Similar to the flexible edge portion, the connecting portion 166 between the distal member 164 and the proximal member 162 can be arranged to flex or bend. The connecting portion 166 can flex or bend between the proximal member 162 and the distal member 164 as the proximal member 162 and/or the distal member 164 move toward and/or away from one another. The proximal member 162 and the distal member 164 can be forced toward one another as the user walks or due to user anatomy or with the user of heel lifts and/or wedges in the foot bed of the walker 100, or under other conditions.

By flexing between the proximal member 162 and the distal member 164, the connecting portion 166 can help reduce or eliminate the formation of pressure points along the dorsal surface of a user's lower leg, ankle, or foot from the dorsal shell 104. Further, due to the flexible nature or resiliency of the connection portion 166, when the dorsal shell 104 is closed around the user's lower leg, ankle or foot, different sized anatomies can be accommodated using the same sized walker 100. In addition, the connecting portion 166 can help the dorsal shell 104 automatically expand or contract due to swelling or reduction of swelling in the lower leg, ankle, and foot of a user.

The connecting portion 166 can include a periphery, an upper generally continuous surface area and a pair of laterally upstanding, sidewall portions extending along two opposed sides of the upper surface area. The connecting portion 166 can further include a distal sidewall portion extending along an edge of the upper surface area and a proximal sidewall portion extending along an edge of the upper surface area. The proximal sidewall portion can extend along an imaginary curved line that defines a peak near a center of the connecting portion 166.

As best seen in FIG. 9, the connecting portion 166 further includes a lower generally continuous surface area opposed the upper surface area. At least a portion of the lower surface area can have a concave curvature to help the connecting portion 166 fit over the ridge of the foot and/or the ankle. The concave curvature of the connecting portion 166 can allow the connecting portion 166 to be more comfortably arranged along the dorsal surface of the ankle and/or the foot of a user. A thickness defined between the upper and lower surface areas of the connecting portion 166 can be arranged to provide cushioning and/or protection to the ankle and/or foot.

The connecting portion 166 can be attached between the proximal member 162 and the distal member 164 in any suitable manner. The connecting portion 166 may be formed via overmolding as discussed above. The connecting portion 166 can overlap a portion of the upper surface areas of the proximal member 162 and the distal member 164, increasing the connection surface area between the connecting portion 166, the proximal member 162, and the distal member 164.

Referring again to FIG. 8B, a ridge 174 is formed on the upper surface area of the proximal member 162 near a distal edge of the proximal member 162. A ridge 176 is formed on the upper surface of the distal member 164 near a proximal edge of the distal member 164. The connecting portion 166 extends between the ridge 174 and the ridge 176.

The ridge portion 174 can include an upper surface area, a distal sidewall surface attached to the connecting portion 166 and a general shape that corresponds to the proximal sidewall portion of the connecting portion 166. The ridge portion 176 can include an upper surface area, a distal sidewall portion, and proximal sidewall portion attached to the connecting portion 166. As shown, the proximal sidewall portion of the ridge portion 176 can be curved such that the width of the ridge portion 176 between the proximal and distal sidewall portions varies.

The ridge portions 174, 176 can help maintain the position of the ankle strap 154A on the dorsal shell 104. When the strap 154A is tightened over the connecting portion 166 across the ankle of the user (best shown in FIG. 1), the strap 154A can compress the connecting portion 166 to a degree such that the lower surface area of the strap 154A descends below the upper surface areas of the ridge portions 174, 176. This can allow the distal sidewall portion of the ridge 174 and the proximal sidewall portion of the ridge 176 to limit proximal and distal movement of the strap 154A.

The ridge portions 174, 176 can help prevent the strap 154A from digging into the ankle of the user. The connecting portion 166 can be arranged such that compressive pressure or forces exerted on the connecting portion 166 by the strap 154A are substantially transferred from the connecting portion 166 to the ridge portions 174, 176, and the upper surfaces of the distal member 164 and the proximal portion 166 rather than the ankle and/or the foot.

While the connecting portion 166 is described forming a hinge mechanism between the proximal member 162 and the distal member 164, alternative hinge mechanisms can be used, such as pivot pins and sleeves, piano or butterfly hinges, or other suitable hinge mechanisms can be used in place of the connecting portion 166. For instance, one or more malleable bars or bars (not shown) can connect the proximal member 162 and the distal member 164. The bars can be arranged as a metal stay such that a clinician or medical professional can selectively bend the bars to change or set the aspect ratio of the proximal and distal members 162, 164 relative to one another. This can help accommodate treatment of Achilles tendon injuries, for example, where heel wedges are selectively positioned within the foot bed of the walker 100 by a medical professional to adjust the angle of the user's foot within the foot bed. Optionally, the bars can be enclosed within a protective member such as an overmold portion to provide a comfort fit.

Referring now to the proximal member 162 best shown in FIG. 8A, a plurality of apertures 120 can be formed in the proximal member 162. The apertures 120 can exhibit any suitable configuration. The apertures 120 can have a periphery having opposed parallel longitudinal sidewall portion and curved or rounded end wall portions. The apertures 120 can be arranged in two columns extending at least a portion of the distance between the proximal edge of the proximal member 162 and the distal edge of the proximal member 162. The columns can be located on opposite sides of the longitudinal axis of the dorsal shell 104.

Some or all of the apertures 120 can be slanted with a through-hole portion and a non-through hole portion. For example, one or more of the apertures 120 can include two through-holes separated by a non-through hole. Similar to the apertures in the base shell 102, the apertures 120 can help venting by allowing air to flow into and out of the through-hole portion. The apertures 120 can help reduce the weight of the walker 100 by reducing the amount of material in the dorsal shell 104. The apertures 120 also may help strengthen the dorsal shell 104 by reinforcing the proximal member 162 with the material remaining in the non-through hole portion of the aperture 120.

A flexible or resilient edge portion 178 can be formed on the proximal terminal end of the proximal member 162. The flexible edge portion 178 can exhibit any suitable configuration and can be formed via any suitable technique as discussed above. The flexible edge portion 178 can include a periphery, a generally convex upper surface area, a distal sidewall portion attached to the proximal member 162, a proximal sidewall portion, and a generally concave lower surface area. The distal sidewall portion of the flexible edge portion 178 can extend along a generally wavy line defining a valley in the tibial crest area of the user.

The flexible edge portion 178 can bend or flex when the leg of the user pushes on the flexible edge portion 178. The flexible edge portion 178 can bend or flex when the proximal member 162 becomes angled or pitched toward the user's lower leg. This can allow the flexible edge portion 178 to act as an expansion mechanism to accommodate different sized lower legs of different users, providing a comfortable fit for different users having different sized anatomies. The bending or flexing of the flexible edge portion 178 can also reduce and/or eliminate the likelihood of pressure points on the tibia, increasing the comfort of the walker 100 and providing tibia relief.

Optionally, a tibia relief portion 180 of the flexible edge portion 178 can angle, curve, or radially extend away from the other portions of the upper surface area of the flexible edge portion 178 or the user's leg, spacing the tibia relief portion 180 of the flexible edge portion 178 a distance away from the user's leg. This can provide additional space for the tibial crest, allowing the flexible edge portion 178 to better accommodate the tibial crest as the user walks. This can also help reduce the likelihood of pressure points or edge pressures on the leg or tibia from the dorsal shell 104. For instance, because the tibia relief portion 180 extends away from the lower leg, as the user's lower leg pushes against the flexible edge portion 178, the user's leg can bend or flex the flexible edge portion 178 further away from proximal member 162, reducing pressure points or edge pressures on the leg from the dorsal shell 108. The tibia relief portion 180 can be arranged to bend away from the leg and toward an outer surface of the proximal member 162. In other embodiments, the flexible edge portion 178 can be omitted.

A compliance strap guide 182 can be formed on the dorsal shell for accommodating a compliance strap. A compliance strap is a strap that can be used to deter a user or patient from prematurely or frequently removing a walker, which can disrupt the healing process of the foot.

Figure 10:
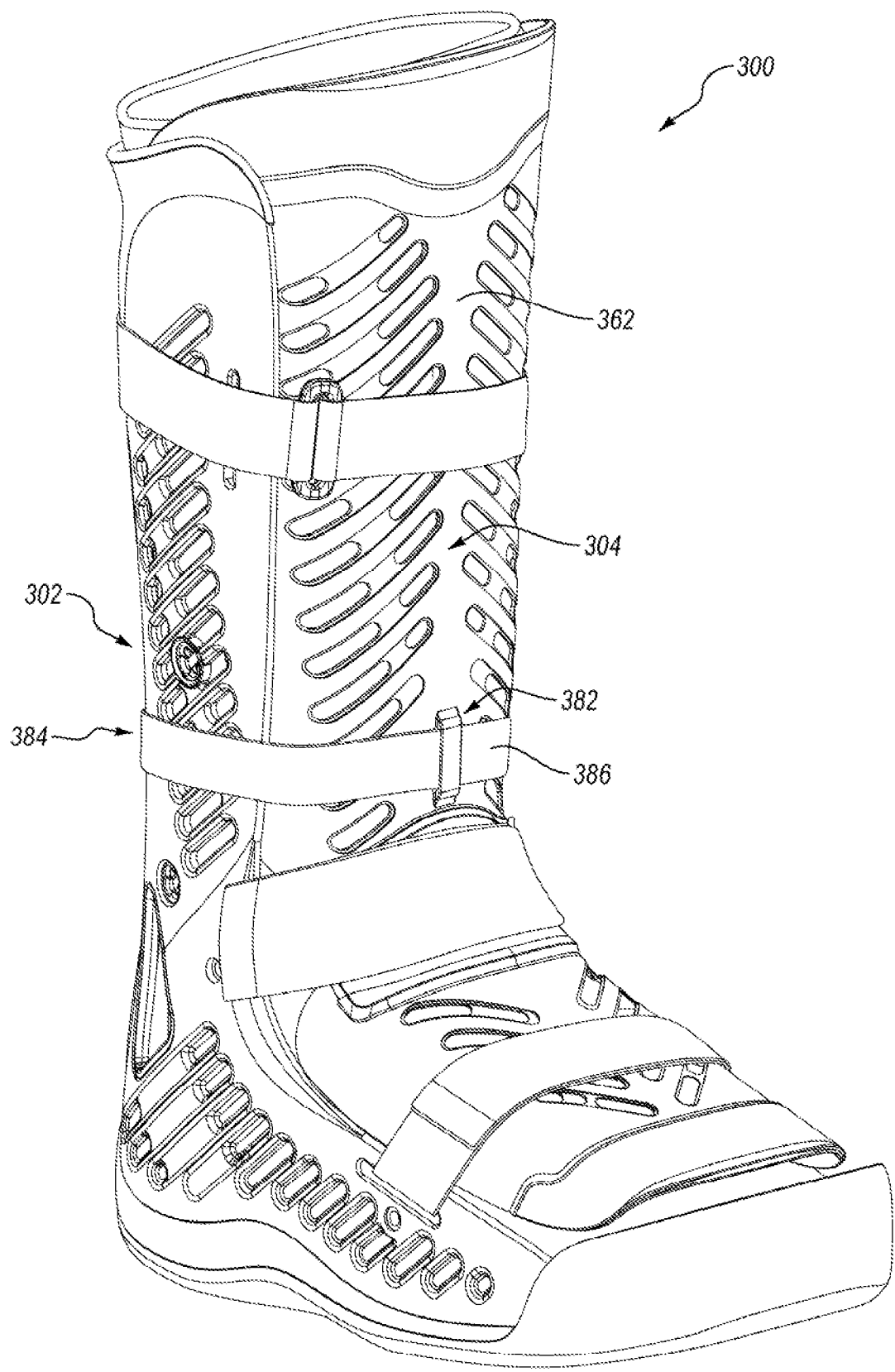
FIG. 10 is a front isometric view of a walker according to another embodiment.

Another exemplary embodiment of a walker 300 is shown in FIG. 10. This embodiment includes a base shell 302, a dorsal shell 304, and a compliance strap guide 382 can be positioned on an anterior aspect of a proximal member 362 of the dorsal shell 304. A compliance strap assembly 384 can comprise a compliance strap 386 arranged through the compliance strap guide 382 and irreversibly attached to itself via an adhesive. When the compliance strap 386 is used with the walker 300, the dorsal shell 304 cannot be moved away from the base shell 302, preventing removal of the walker 300 from the user's foot.

Locating the guide 382 on the anterior aspect can help increase the usability of the guide 382. For instance, when the walker 300 is placed on a user by a medical professional, the medical professional is typically situated in front of the walker 300. The position of the compliance strap guide 382 on the anterior aspect of the proximal member 362 allows the medical professional to more easily install a compliance strap on the walker through the guide 382. This also allows the compliance strap guide 382 to be positioned such that it will not rub against and/or damage an unaffected limb of the user during use of the walker 300.

The compliance strap 386 can comprise a strap including high-density polyethylene fibers (e.g., a Tyvek® strap) arranged through the compliance strap guide 382 and irreversibly attached to itself via an adhesive such that the compliance strap cannot be removed from the walker 300 by sliding the compliance strap up and over the walker 300. The compliance strap 386 can only be removed by cutting or damaging the strap 386, preventing removal of the walker without a clinician or medical professional knowing. It will be appreciated that the compliance strap guide 382 and the compliance strap 386 are exemplary only, and other suitable configurations are possible. For instance, the base shell 302 can include a recess or other feature suitable to receive a compliance strap.

Figure 11:
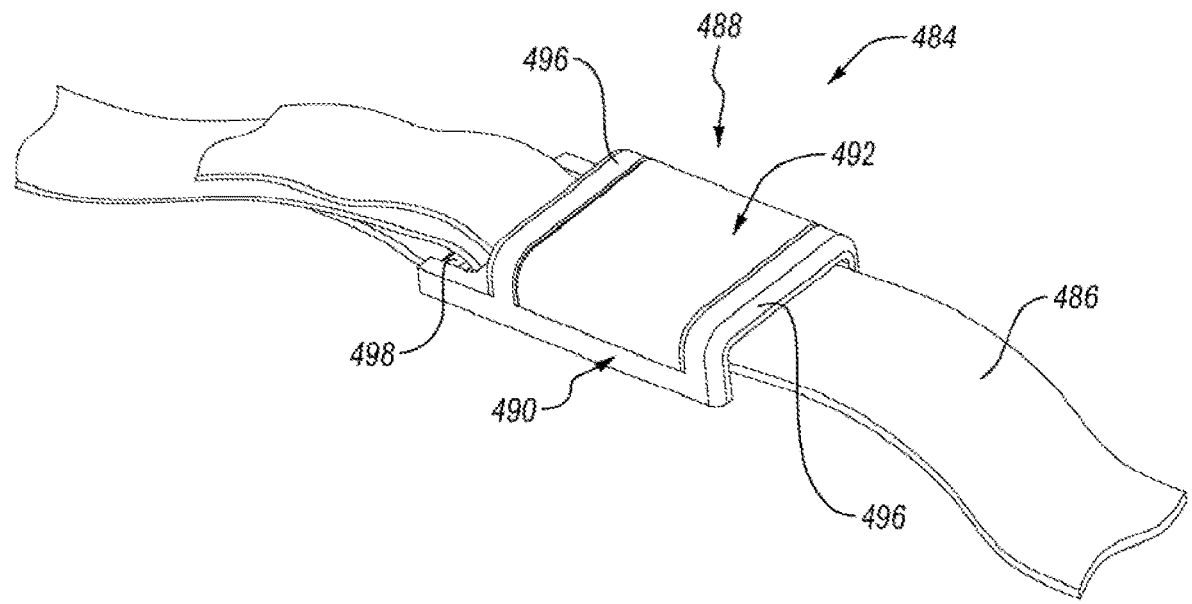
FIG. 11 is a front isometric view of a compliance clasp assembly in a closed position according to another embodiment.
Figure 12:
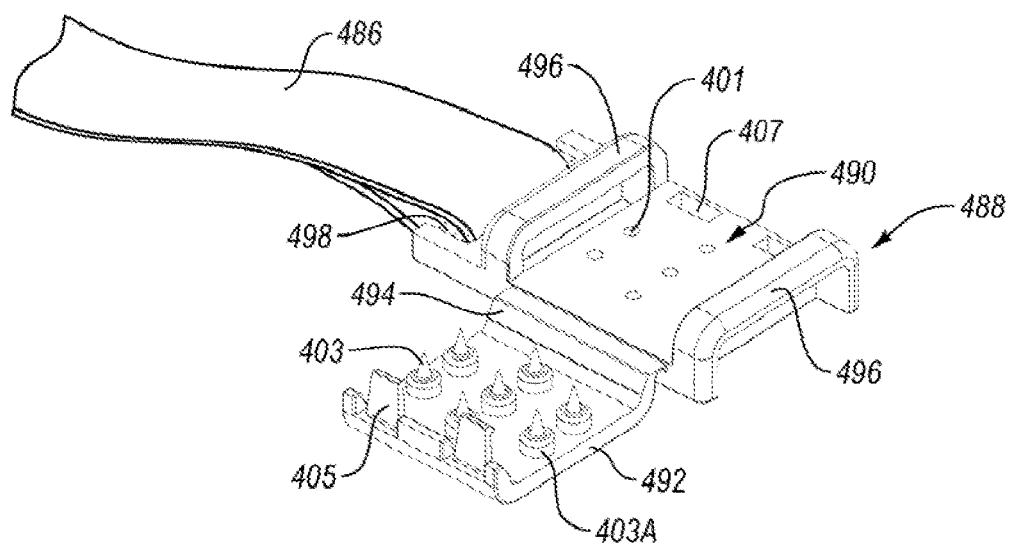
FIG. 12 is a partial front isometric view of a compliance clasp in an open position according to an embodiment.
Figure 13:
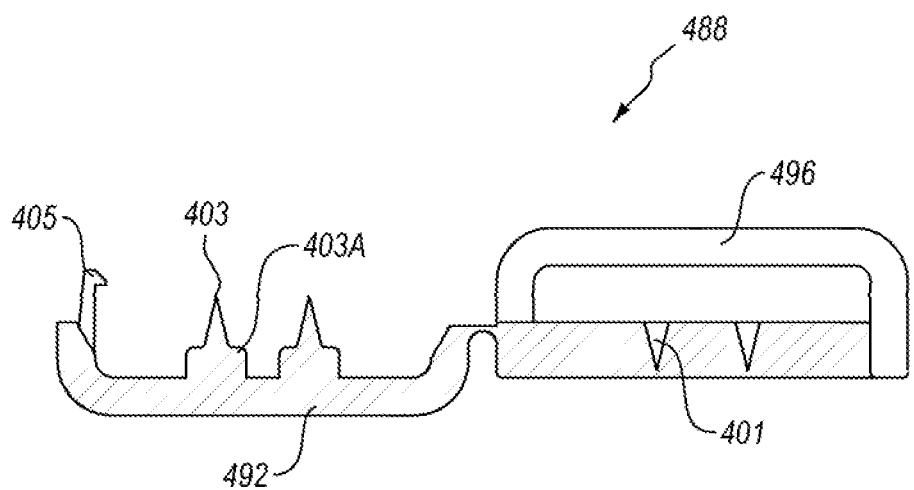
FIG. 13 is a sectional view of the compliance clasp shown in FIG. 12 taken along section line 12-12.

Another exemplary embodiment of a compliance strap assembly 484 is shown in FIG. 11-13. The compliance strap assembly 484 can include a compliance strap 486 and a compliance clasp 488. The compliance strap 486 can be formed of any suitable material such as, but not limited to, nylon and/or high-density polyethylene fibers.

The compliance clasp 488 can include a base member 490 and a door member 492 pivotally attached to one another. A living hinge 494 can be formed between the base member 490 and the door member 492. The living hinge 494 can be arranged to allow a clinician or medical professional to close the compliance clasp 488 with one hand applying tension to the compliance strap 486 and the other hand bringing the door member 492 and the base member 490 together. Alternatively, the base member 490 can be formed as a separate piece from the door member 492 and pivotally attached thereto in any suitable manner.

The base member 490 and the door member 492 can exhibit any suitable configuration. For instance, each of the base member 490 and the door member 492 can exhibit a generally rounded rectangular shape having a periphery, an upper surface area, and a lower surface area. In other embodiments, the base member 490 and the door member 492 can exhibit a generally triangular shape, a generally diamond shape, a generally oval shape, combinations thereof, or any other suitable shape.

A pair of strap guides 496 can be formed on the upper surface of the base member 490 for receiving an end portion of the compliance strap 486. The strap guides 496 can be arranged to maintain alignment of the compliance strap 486 with the compliance clasp 488, reducing the likelihood that the compliance strap 486 will interfere with the door member 492 in a closed position described below.

A receiving loop 498 can also be formed on the base member 490 for providing an attachment point for one end of the compliance strap 486. This advantageously allows the one end to be attached to the receiving loop 498 and the other end of the compliance strap 486 to be looped through a compliance strap guide (e.g., guide 382), around the walker (e.g., walker 300), through the strap guides 496, and attached to itself.

Referring to FIGS. 12 and 13, a plurality of recesses 401 can be formed in the upper surface of the base member 490. A plurality of spike-like protrusions 403 can be formed on the lower surface area of the door member 492 that correspond to the plurality of recesses 401. The spike-like protrusions 403 can include a wider base portion 403A, providing additional strength to the spike-like protrusions 403.

The compliance clasp 488 can be moveable between an open position (shown in FIG. 12) in which the door member 492 is rotated away from the base member 490, and a closed position in which the lower surface area of the door member 492 is rotated onto the upper surface area of the base member 490. When the compliance clasp 488 is in the closed position, the spike-like protrusions 403 penetrate the recesses 401 to lock or grasp the portion of the compliance strap 486 extending between the base member 490 and the door member 492 within the compliance clasp 488.

The spike-like protrusions 403 and the recesses 401 can be arranged in any suitable manner. The spike-like protrusions 403 and the recesses 401 can be generally upright. The spike-like protrusions 403 and the recesses 401 can extend at one or more angles. For instance, the spike-like protrusions 403 and the recesses 401 can extend at one or more angles configured to allow for limited one-way movement of the compliance strap 486 with the compliance clasp 488 in the closed position. This can allow a clinician or medical professional to tighten the compliance strap 486 with the compliance clasp 488 in the closed or position.

The spike-like protrusions 403 can be arranged to at least partially pierce the compliance strap 486. Applying tension to the compliance strap 486 when the compliance clasp 488 is in the closed position can tear the strap 486 or break one or more of the spike-like protrusions 403. Thus, if a non-compliant patient removes the compliance clasp 488 from the strap 486 to remove the walker 300, the clinician or medical professional will know upon examination of the compliance assembly 484.

One or more detents 405 may be formed on and extend from the lower surface of the door member 492. One or more locking grooves 407 corresponding to the detents 405 can be formed in the upper surface of the base member 490. The locking detents 405 can engage the locking grooves 407 when the compliance clasp 488 is in the closed position, creating an irreversible closure.

This allows the compliance clasp 488 to be irreversibly locked in the locking position, preventing a user from removing the compliance clasp 488 from the strap 486 without breaking or damaging the strap 486 and/or the compliance clasp 488. As seen, the detents 405 and the locking grooves 407 can be concealed within the compliance clasp 488 when the compliance clasp 488 is in the closed position, preventing the user from over-riding or tampering with the locking mechanism of the compliance clasp 488.

The compliance clasp 488 can be formed from any suitable material. The compliance clasp 488 can include metals, such as aluminum, carbon, composite materials, such as carbon fiber/epoxy composites, glass fiber/epoxy composites, or suitable plastic materials, such as thermoplastic or thermosetting polymers, fiber reinforced plastic, molded chopped fibers, or any other suitable material. Different portions of the compliance clasp 488 can be formed from different materials. For instance, one portion of the compliance clasp 488 can be formed form polypropylene (e.g., the living hinge) and another portion can be formed by a metal insert (e.g., the spike-like protrusions).

While the door member 492 is described including the spike-like protrusions 403 and the base member 490 is described including the recesses 401, it will be appreciated that the door member 492 may include the recesses and the base member 490 may include the spike-like protrusions. Moreover, it will be appreciated that the door member and/or the base member may include any suitable numbers of spike-like protrusions and/or recesses. Further, the compliance clasp 488 can include any suitable feature to lock or grasp the compliance strap 486 between the base and door members.

Figure 14:
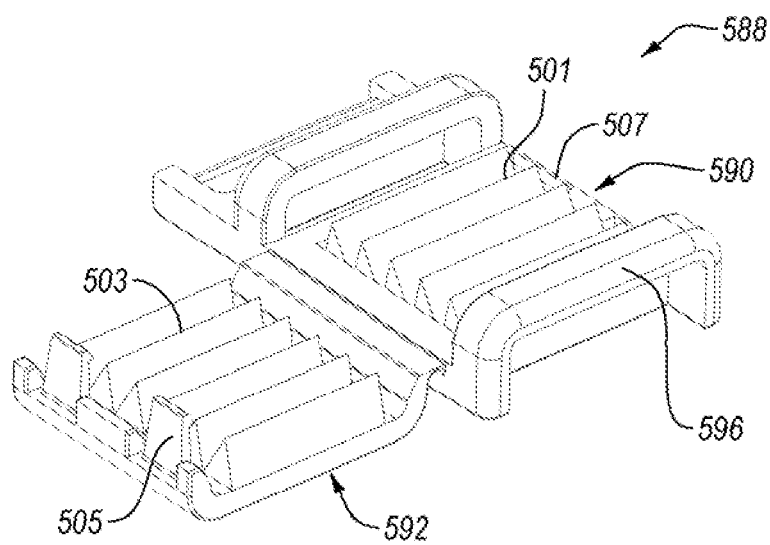
FIG. 14 is a front isometric view of a compliance clasp in an open position according to another embodiment.

Another exemplary embodiment of a compliance clasp 588 is illustrated in FIG. 14. The compliance clasp 588 can be similar to the compliance clasp 488, except that base member 590 includes a first plurality of teeth 501 formed in the upper surface of the base member 590 and the door member 592 includes a second plurality of teeth 503 of complementary shape in the lower surface of the door member 592 for interlocking with the first plurality of teeth 501 of the base member 590.

When the compliance clasp 588 is in the receiving position, the compliance strap can easily slide through the strap guides 596 on the base member 590 to adjust the location and/or tension in the strap. When the compliance clasp 588 is moved into the closed position, the teeth 501 of the base member 590 engage the teeth 503 of the door member 592 to lock or grasp the compliance strap within the compliance clasp 588. Similar to the compliance clasp 488, the compliance clasp 588 can include detents 505 and locking grooves 507 arranged to irreversibly lock the compliance clasp 588 in the closed position.

Another exemplary embodiment of a walker 600 is shown in FIGS. 15-28. The walker 600 can be similar to the walker 100 except that the walker 600 includes an inflation system 601 arranged to reduce pressure points within the walker 600, accommodate different sized anatomies, and/or to accommodate swelling.

Figure 15:
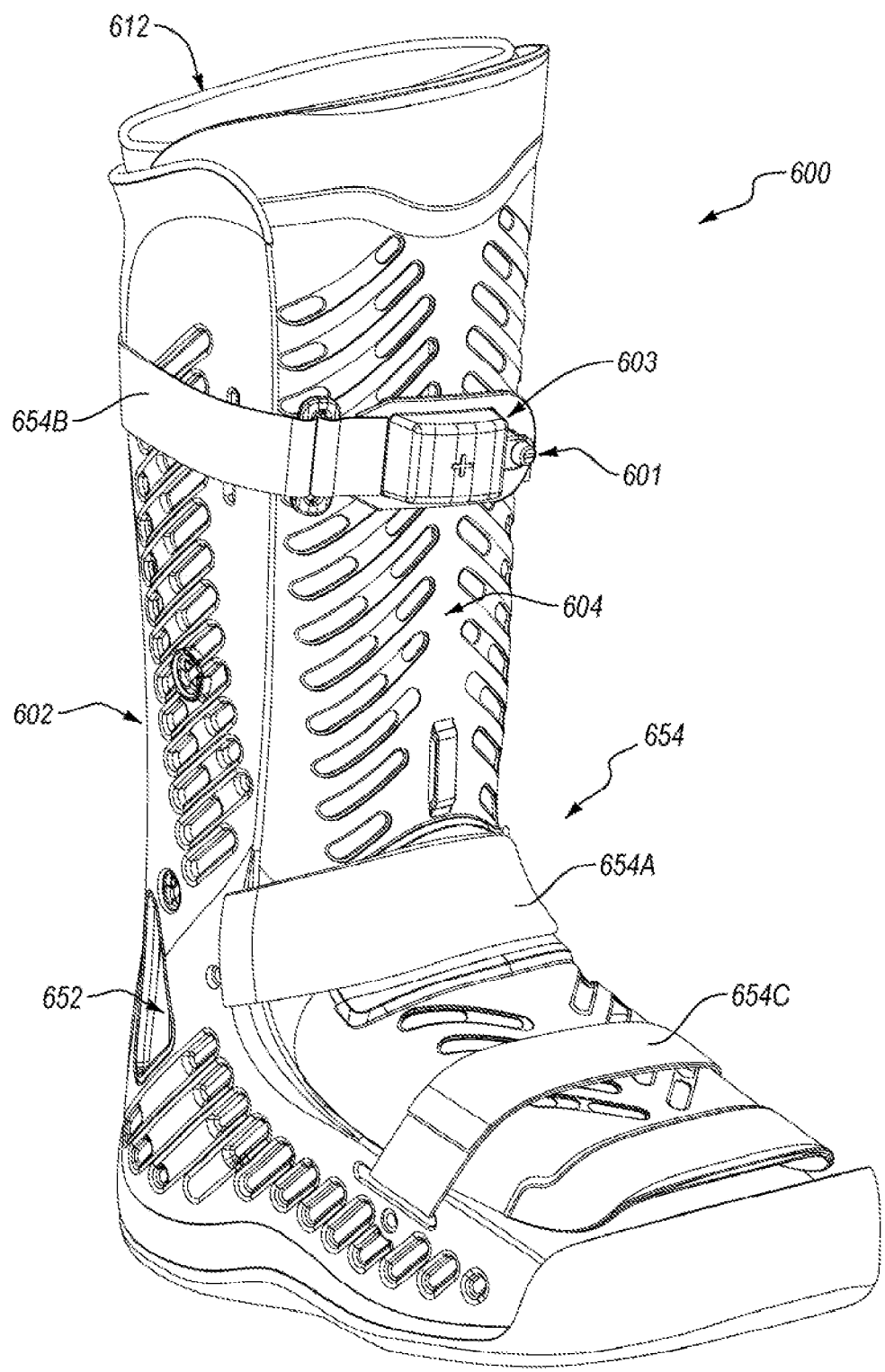
FIG. 15 is a front isometric view of a walker according to another embodiment.
Figure 16:
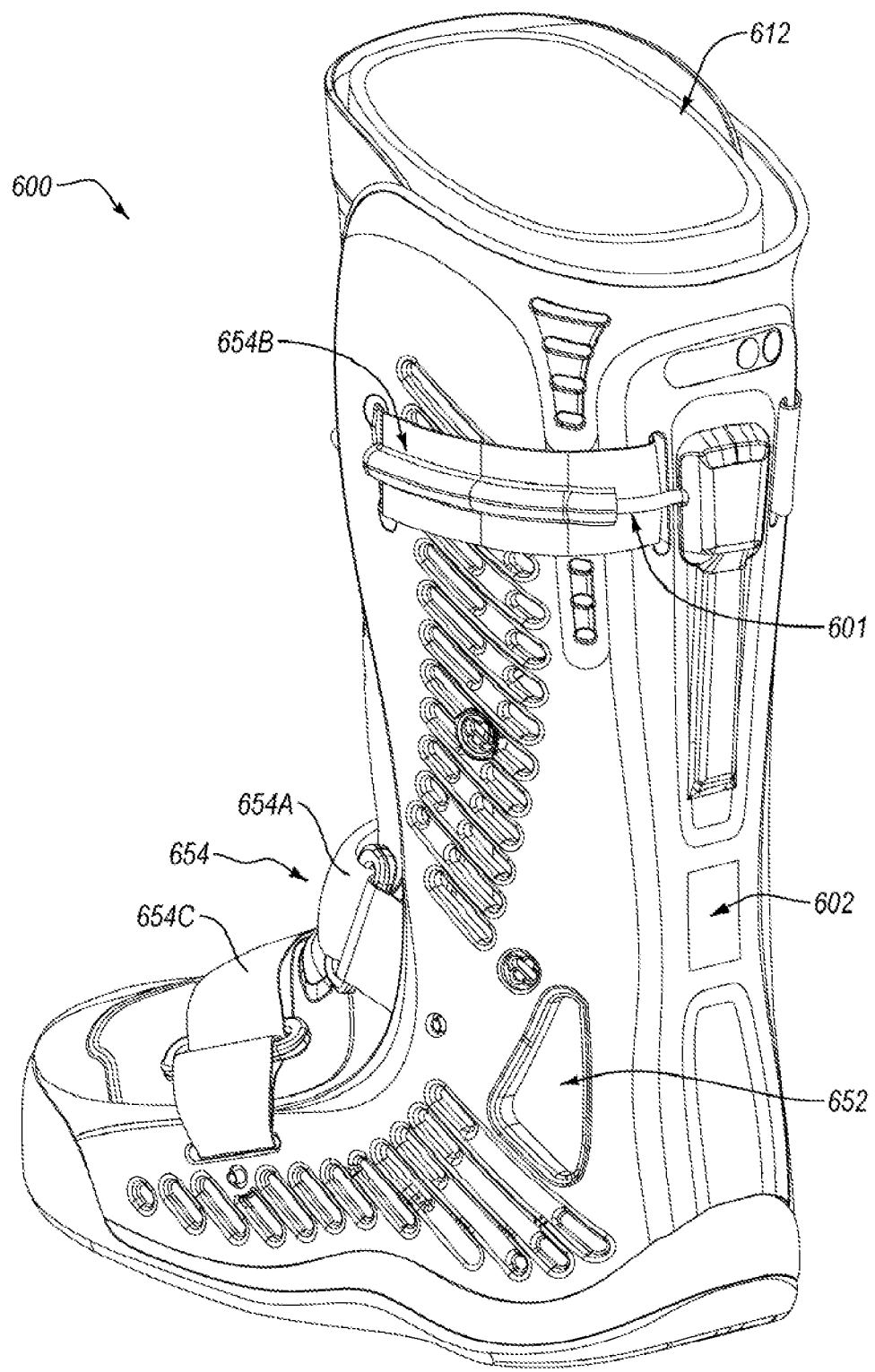
FIG. 16 is a back isometric view of the walker shown in FIG. 15.

As can be seen from FIGS. 15 and 16, the walker 600 includes complementary base shell 602 and dorsal shell 604 and a plurality of straps 654 arranged to bring the base shell 602 and the dorsal shell 604 closer together. The plurality of straps 654 can include an ankle strap 654A, an upper strap 654B, and a foot strap 654C. A soft good liner 612 can be provided inside the base shell 602 and the inflation system 601 can be integrated on the interior and/or the exterior of the walker 600.

Figure 17:
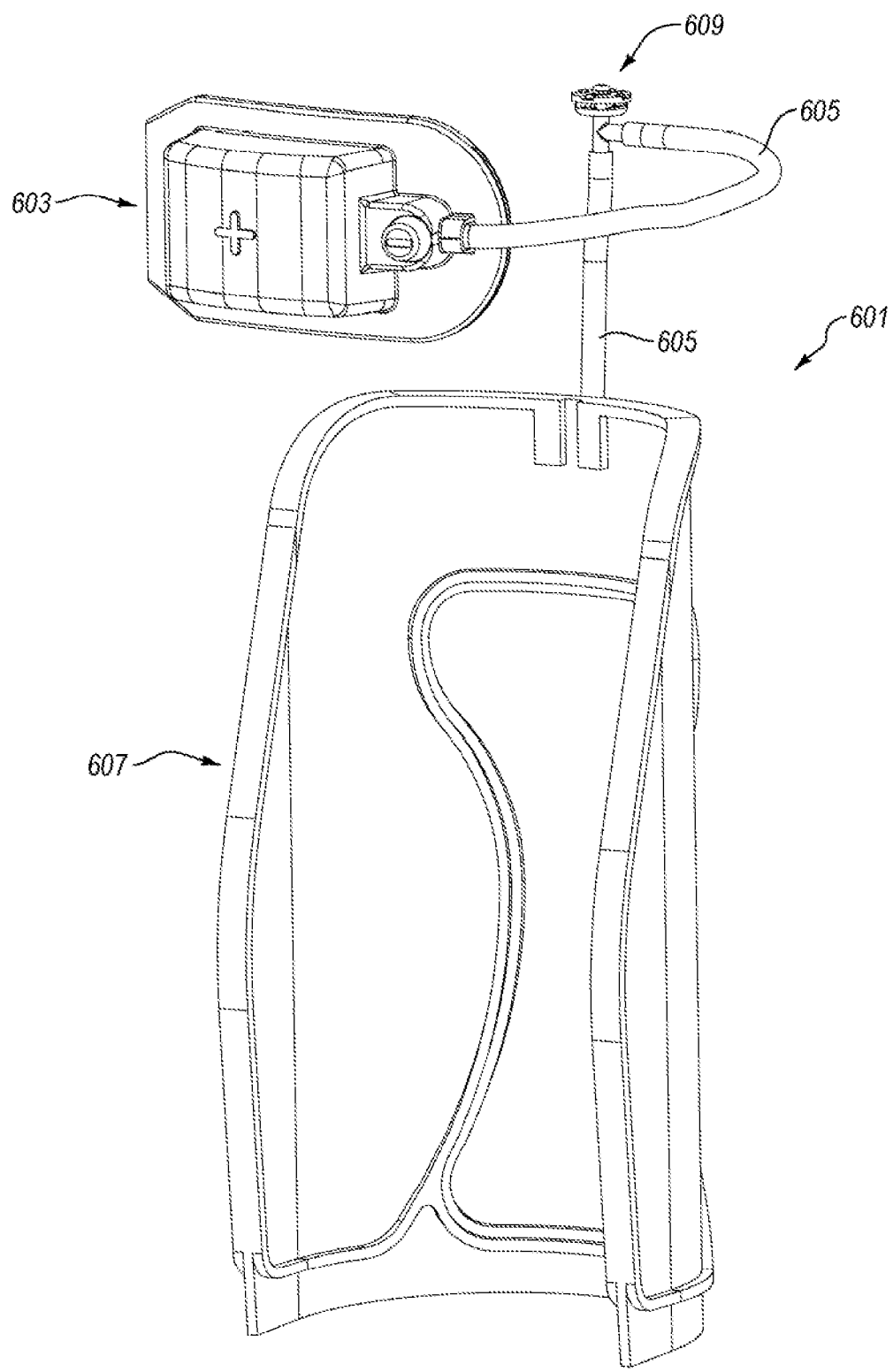
FIG. 17 is a schematic view of an air inflation system for use with the walker shown in FIG. 15 according to an embodiment.

For simplicity, FIG. 17 shows the inflation system 601 removed from the walker 600 according to an embodiment. The inflation system 601 can include a pump assembly 603, one or more inflation tubes 605, and an inflatable bladder 607. The inflatable bladder 607 can be arranged in an ankle receiving portion of the walker 600 (best shown in FIG. 27) and inflated and/or deflated via the one or more inflation tubes 605, which are in fluid communication with the pump assembly 603. Optionally, the inflation system 601 can include a pressure relief valve assembly 609 that can automatically expel excess air from the inflation system 601, reducing the likelihood of over-inflation that can harm the user.

Figure 20:
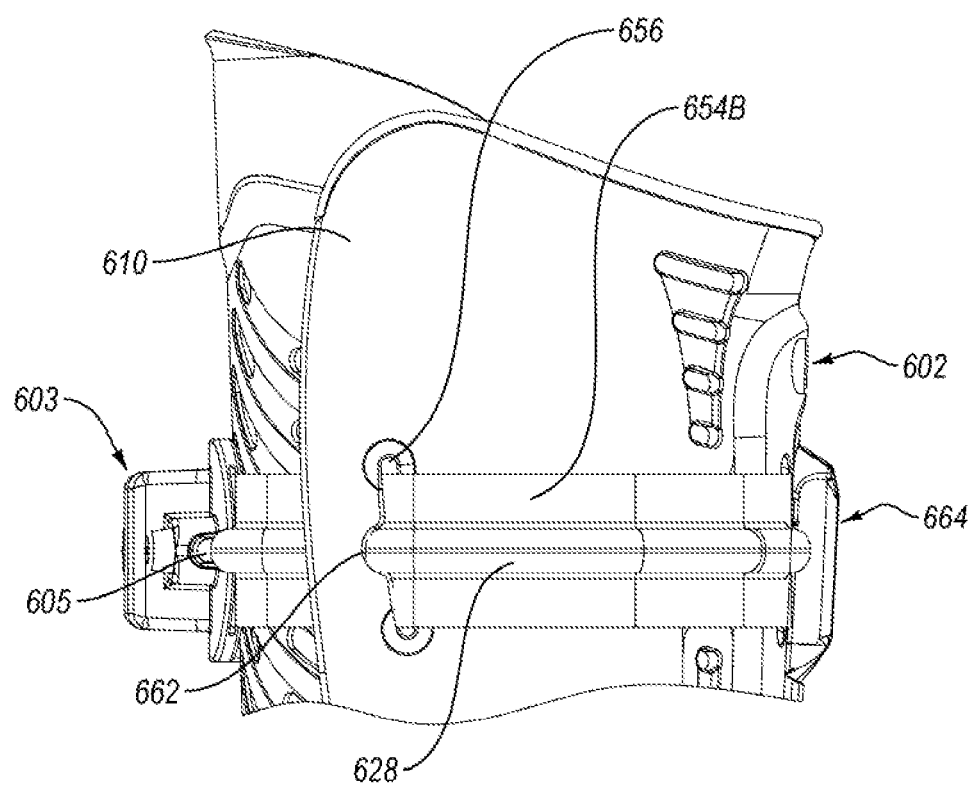
FIG. 20 is a partial side view of the walker shown in FIG. 15.

As best shown in FIGS. 15 and 20, the pump assembly 603 can be connected to the inflation tube 605 and can be attached to and/or carried by the upper strap 654B. Arranging the pump assembly 603 on the upper strap 654B can allow the pump assembly 603 to be in a relatively fixed position with respect to the base shell 602. As the location of the dorsal shell 604 moves up and down as a user moves or to accommodate variations in user anatomy, the position of the pump assembly 603 relative to the base shell 602 can remain substantially fixed on the upper strap 654B. This has the effect of preventing kinking of the inflation tubes 605 and/or unwanted movement of the pump assembly 603 that could inadvertently inflate or deflate the inflatable bladder 607. Arranging the pump assembly 603 on the upper strap 654B on the anterior of the walker 600 can also make the pump assembly 603 more usable and accessible to a user.

Optionally, the pump assembly 603 can be permanently attached to the strap 654B so that the pump assembly 603 is not easily misplaced. The upper strap 654B may be generally flexible, allowing the pump assembly 603 to generally conform to the shape of the dorsal shell 604 below the strap 654B, regardless of the anterior and/or posterior position of the dorsal shell 604 relative to the strap 654B.

It will be appreciated that the location of the pump assembly 603 on the anterior region of the upper strap 654B is exemplary only, as other suitable locations of the pump assembly 603 are possible. For example, the pump assembly 603 can be located on the ankle strap 654A. The pump assembly 603 can be arranged on the lateral region of the upper strap 654B or the exterior of the base shell 602 in the lower leg region of the walker 600.

Figure 18:
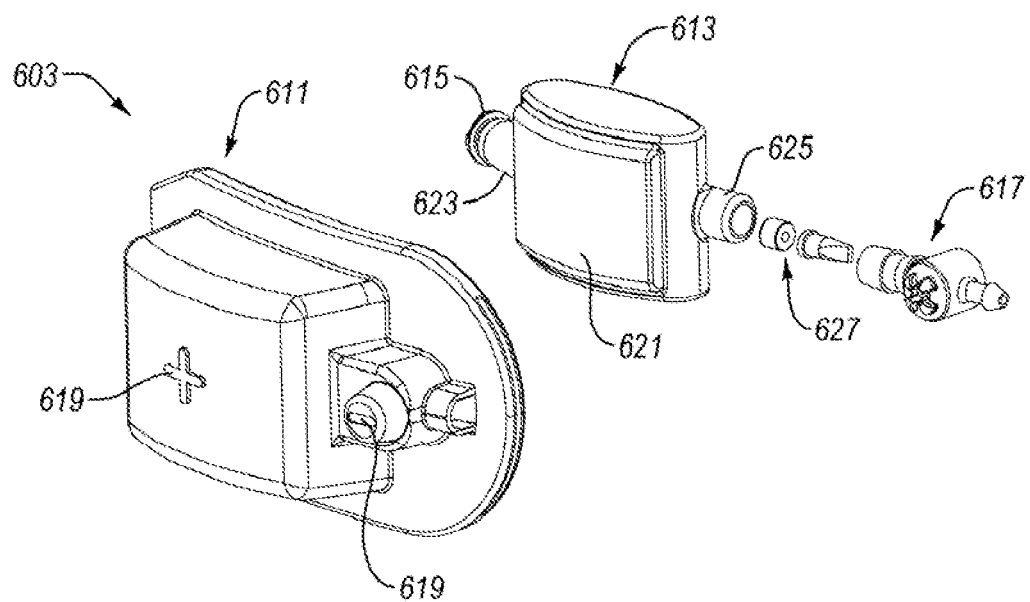
FIG. 18 is an exploded view of a pump assembly according to an embodiment.

As seen in FIG. 18, the pump assembly 603 can include a cover 611, a pump 613, a fill valve 615, and a release valve 617. The cover 611 can be arranged to house the pump 613, the fill valve 615, and the release valve 617. The cover 611 can exhibit any suitable configuration. The cover 611 can be made from any suitable flexible, resilient, or compliant material. The cover 611 can include one or more vent openings to allow air vented from the inflatable bladder 607 to pass through the cover 611 to the atmosphere.

Optionally, the cover 611 can include one or more enhancement features 619, such as raised or recessed portions, which can be configured in any suitable design. For example, the enhancement features 619 may be configured as a cross "+" indicating inflation and an elongated recess "−" indicating deflation. The enhancement features 619 can also help enhance function and/or gripping so that a user can more easily actuate the pump 613 and/or the release valve 617. The enhancement features 619 can also provide visual and/or tactile indicators for the user. The cover 611 can further include one or more features to wrap around the strap 654B for better securement of the pump assembly 603 to the strap 654B. As noted above, the cover 611 can exhibit any suitable configuration.

The pump 613 is housed within the pump cover 611 and can comprise any suitable pump type. For example, the pump 613 can be a diaphragm or positive displacement pump including a diaphragm or body 621, an inlet 623, and an outlet 625. The inlet 623 can be formed in one end of the body 621 and can allow air to flow into the body 621. The inlet 623 can also be selectively closed when the pump 613 is actuated so that air does not flow out of the pump 613 through the inlet 623. Optionally, the inlet 623 can be arranged as a release valve or the pressure relief valve described below. The outlet 625 can be opposed to the inlet 623 on the other side of the body 621. A one-way valve assembly 627 can be provided within the outlet 625 for allowing air to pass from the pump 613 into the inflatable bladder 607, but not from the inflatable bladder 607 to the pump 613.

In operation, when the diaphragm or body 621 of the pump 613 moves up (e.g., volume increases), pressure within the pump 613 decreases, causing air to be drawn into the pump through the inlet 623. When the body 621 of the pump 613 moves down (e.g., volume decreases), the pressure in the pump 613 increases, forcing the air that was previously drawn in out of the pump 613 through the outlet 625. Finally, the body 621 moving up once again draws air into the pump 613.

The pump 613 can have any suitable shape and size. For instance, the pump can include a generally box-like shape with a convex anterior side and/or a convex posterior side. The shape of the pump can be arranged to maximize the useable stroke volume of the pump 613.

The release valve 617 can be arranged to selectively release pressure within the inflatable bladder 607 and/or the inflation system 601. The release valve 617 can be incorporated with the pump 613. The release valve 617 can be incorporated with the pump assembly 603. The one-way outlet valve assembly 627 can communicate with the inflatable bladder 607 via the release valve 617. The release valve 617 can be activated manually by a user. The release valve 617 can be separate from the pump assembly 603. The release valve 617 can be located at any suitable location on the walker 600.

Alternatively, the pump 613 and/or release valve 617 can be electrically powered by a portable power source associated with the walker 600. The pump 613 can be configured to be usable with fluid or liquid. For example, the pump 613 can be usable with liquid to provide hot and/or cold therapy.

Figure 19:
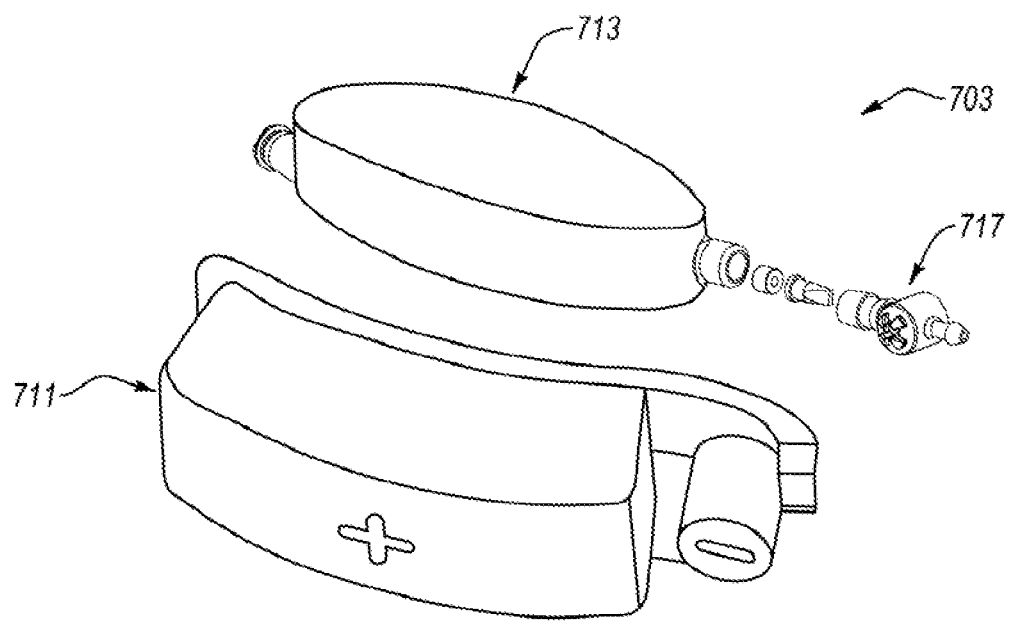
FIG. 19 is an exploded view of a pump assembly according to another embodiment.

FIG. 19 illustrates a pump assembly 703 according to another embodiment. The pump assembly 703 can include a pump 713 having an elongated ovoid-like shape including a maximum dimension between the anterior and posterior sides at a center of the pump 713 that tapers toward each end of the pump 713. A larger, more elongate cover 711 can cover the pump 713 and a release valve 717. The shape of the pump 713 can be arranged to maximize the useable stroke volume of the pump 713.

As seen in FIG. 20, a tube hole 662 can be formed in the proximal wing portion 610 of the base shell 602 for receiving the inflation tube 605 exiting the pump assembly 603. The tube hole 662 can exhibit any suitable configuration. The tube hole 662 can comprise a semi-elliptical relieved portion or cutout on a strap slot 656 in the proximal portion of the wing portion 610. The tube hole 662 can be separate from the strap slot 656. The tube hole 662 can be elongated, circular, or can exhibit any other suitable shape. While one tube hole 662 is shown in the wing portion 610, in other embodiments, two, three, four, or any other number of tube holes 662 are possible.

The inflation tube 605 exiting the pump assembly 603 can be threaded from the interior of the base shell 602 through the tube hole 662. From the tube hole 662, the inflation tube 605 is guided or routed along the exterior of the base shell 602 to the posterior aspect of the base shell 602 where it is connected to the pressure relief valve assembly 609 (shown in FIG. 21), positioned under a cover member 664 attached to the posterior aspect of the base shell 602.

The inflation tube 605 can be flexible so that the inflation tube 605 can generally conform to the contour of the base shell 602. The inflation tube 605 can include one or more segments sized and shaped to generally contour the exterior of the base shell 602. For example, at least one of the segments of the inflation tube 605 can include one or more bends that generally contours the bends or curves in the exterior of the base shell 602. In other embodiments, the inflation tube 605 can be routed in grooves formed on the interior surfaces of the base shell 602.

A fabric sleeve 628 can be located on the upper strap 654B for guiding the inflation tube 605 along the outside of the base shell 602 from the pump assembly 603 to the pressure relief valve assembly 609 within the cover member 664. The fabric sleeve 628 can comprise a unitary sleeve or a plurality of discrete portions of the sleeve 628. The fabric sleeve 628 can comprise an integrated portion of the upper strap 654B. For instance, the fabric sleeve 628 can comprise vertical cutouts in the upper strap 654B into which the inflation tube 605 can be interwoven.

Routing the inflation tube 605 on the outside of the base shell 602 can help reduce or eliminate pressure points on the interior or inside of the walker 600, which can be both uncomfortable as well as a risk for resulting in pressure ulcers. Further, routing the inflation tube 605 on the outside of the base shell 602 protects the inflation tube 605 from being pinched or compressed between the interior of the walker 600 and the leg of the user.

It will be appreciated that the inflation tube 605 can exit the pump assembly 603 in any suitable manner. For example, the inflation tube 605 can be routed in one or more indentations or grooves formed in the exterior or interior surface of the base shell 602. The inflation tube 605 can be routed through guides (e.g., rings or clips) attached to the exterior of the base shell 602, between the upper strap 654B and the exterior of the base shell 602, or in any other suitable arrangement.

Figure 21:
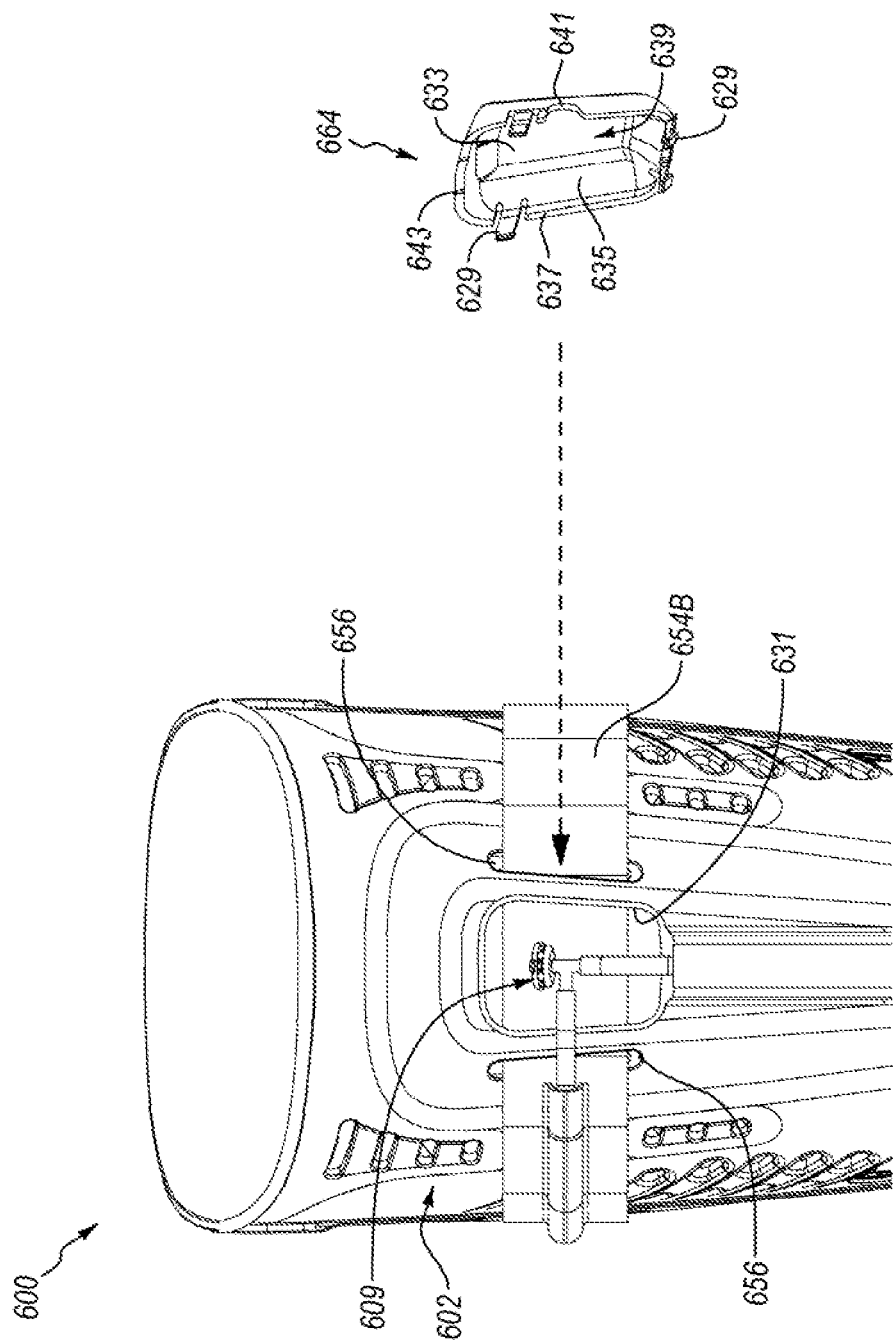
FIG. 21 is a partial exploded back view of the walker shown in FIG. 15.

For simplicity, FIG. 21 is a partial view of the posterior of the base shell 602 with the cover member 664 removed. As shown, the inflation tube 605 connects to the pressure relief valve assembly 609, which is housed within a cavity or cutout 631 formed in the base shell 602. The cutout 631 can have any suitable configuration. The cutout 631 can extend completely between the interior and exterior surface of the base shell 602. The cutout 631 can have a generally rectangular shape, a generally trapezoidal shape, a shape that generally corresponds to the shape of the pressure relief valve assembly, or any other suitable shape.

A pair of strap slots 656 can be formed on opposing sides of the cutout 631. The upper strap 654B can pass from the exterior of the base shell 602 and through a strap slot 656, situating the upper strap 654B behind the pressure relief valve assembly 609. The strap 654B can then extend through the other strap slot 656 back to the exterior of the base shell 602. This allows the strap 654B to form a protective barrier between the pressure relief valve assembly 609 and the user's leg.

The cover member 664 can be attached the base shell 602 over the cutout 631 and the pressure relief valve assembly 609. The cover member 664 can include a base portion 633 and a peripheral sidewall 635 arranged to extend from the base portion 633 toward the base shell 602 of the walker 600.

A recess 639 in the cover member 664 is bounded the sidewall 635 and the base portion 633 so that the bottom of the recess 639 is above (recessed within) the rim 637 of the sidewall 635 to provide a space for the pressure relief valve assembly 648. This can allow the base portion 633 and the sidewall 535 to substantially enclose the pressure relief valve assembly 609 within the recess 639, protecting the pressure relief valve assembly 609 within the cutout 631 and helping to deter tampering.

The sidewall 635 defines a rim 637 extending around the base portion 633. At least a portion of the rim 637 can be contoured to generally correspond to the contour of the posterior of the base shell 602. This can allow the cover member 664 to form a better fit between the cover member 664 and the base shell 602. The rim 637 can also provide a support area for the cover member 664 when the cover member 664 is attached to the base shell 602. Optionally, one or more ribs 643 can be formed on the rim 637 arranged to crush during attachment of the cover member 664 to the base shell 602 to accommodate variations in the geometry of the base shell 602.

One or more side openings 641 can be formed along the rim 637 of the sidewall 635 for accommodating a portion of the inflation tubes 605. One side opening 641 can be arranged to accommodate a portion of the inflation tube 605 extending between the pump assembly 603 and the pressure relief valve assembly 609. Another side opening 641 can be arranged to accommodate a portion of the inflation tube 605 extending between the pressure relief valve assembly 609 and the inflatable bladder 607.

The cover member 664 can be attached to the base shell 602 in any suitable manner. The cover member 664 can be secured to the base shell 602 via a snap-type connection. The cover member 664 can include a plurality of snaps or hook members 629 integrally formed in the sidewall 635 and configured to snap into the cutout 631 formed in the base shell 602, facilitating assembly. The cover member 664 can be attached to the base shell 602 via gluing or plastic welding. Alternatively, the cover member 664 can be removably attached to the base shell 602 via fasteners, hook-and-loop type systems, clips, magnets, or any other suitable attachment system.

By arranging the pressure relief valve assembly 609 within the cutout 631 and cover member 664, the pressure relief valve assembly 609 can be protected from damage due to accidental contact with external objects. Moreover, the cover member 664 can help limit or eliminate pressure points from components of the inflation system 601 (e.g., the pressure relief valve assembly). The cover member 664 can be used with other components of the inflation system 601. The cover member 664 can also be interchangeable based on needs for various indications such as an adjustable relief valve or housing an activity monitor.

The location of the pressure relief valve assembly 609 on the posterior of the base shell 602, helping to deter tampering. In other embodiments, the pressure relief valve assembly 609 can be incorporated in the inflatable bladder 607, on the lateral side of the base shell 602, or in any other suitable position.

Figure 22:
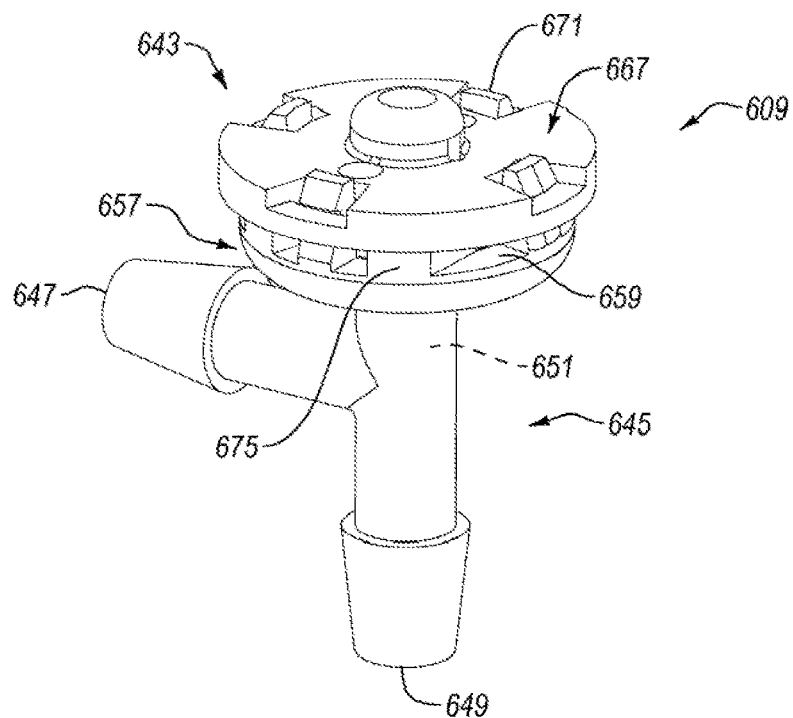
FIG. 22 is a side isometric view of the pressure relief valve assembly shown in FIG. 21.
Figure 23:
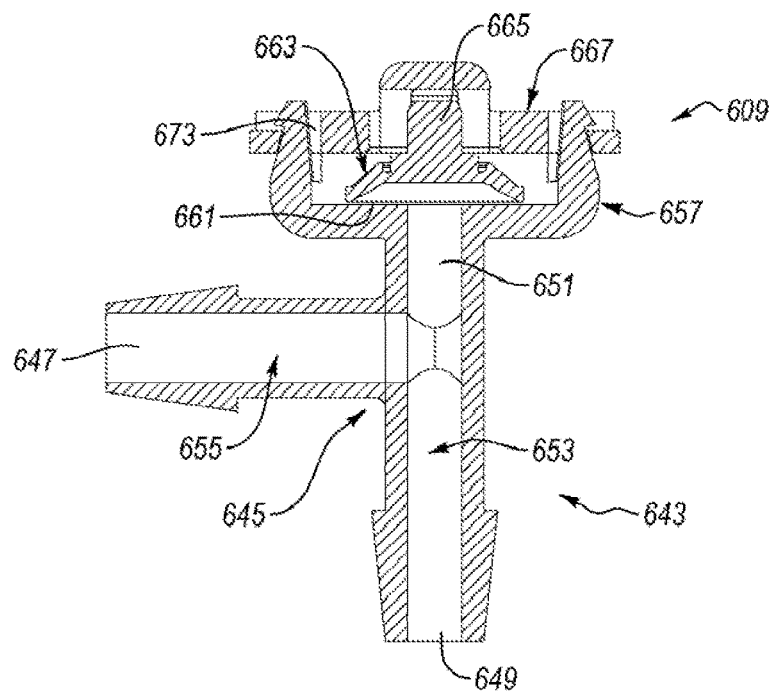
FIG. 23 is a cross sectional view of the pressure relief valve assembly shown in FIG. 22.

The pressure relief valve assembly 609 can exhibit any suitable configuration. Referring now to FIGS. 22 and 23, the pressure relief valve assembly 609 can comprise a pressure relief valve 643 including a valve body 645 having a first port 647, a second port 649, and a third port 651. A first fluid pathway 653 connects the second port 649 and the third port 651. A second fluid pathway 655 connects the first fluid pathway 653 and the first port 647. The first port 647 of the valve body 645 is connected to the inflation tube 605 extending between the pump assembly 603 and the pressure relief valve 643. The second port 649 is connected to the inflation tube 605 extending between the pressure relief valve 643 and the inflatable bladder 607. As seen, the first port 647 can be at about a 90 degree angle relative to the second port 649.

The first port 647 and the second port 649 can be connected to the inflation tubes 605 in any suitable manner. For example, in the illustrated embodiment, the first port 647 and the second port 649 can be connected to the inflation tubes 605 via a barb-type connection. The inflation tubes 605 can be attached to the pressure relief valve 643 via solvent bonding, friction or spin welding, adhesives such as a UV cure adhesive, or any other suitable attachment means.

The valve body 645 further includes an upper portion 657 that can have any suitable configuration. The upper portion 657 comprises a generally cylindrical member including a bottom opening that is in fluid communication with the third port 651 and one or more vent openings 659 in the side thereof for venting air to the atmosphere. The bottom of the upper portion 657 can include a surface surrounding a bottom opening that forms a valve seat 661 for a sealing member 663.

The upper portion 657 is generally hollow, providing a space for the sealing member 663. The sealing member 663 can comprise an elastomeric disk having a diaphragm shape or an umbrella shape positioned within the upper portion 657. The sealing member 663 can comprise a disk having a generally Belleville spring washer shape that includes stem portion 665. An upstream side of the sealing member 663 can be situated within the first fluid pathway 653 and a downstream side can be situated between the sealing member 663 and a retainer member 667. The sealing member 663 can be formed from any suitable material such as silicone and/or other elastomeric materials.

The retainer member 667 is arranged to retain the sealing member 663 within the upper portion 657 of the valve body 645. The retainer member 667 can comprise a generally cylindrical member including a stem having a recessed or hollow portion configured to receive and hold the stem portion 665 of the sealing member 663 in place.

The retainer member 667 may be a separate component from the valve body 645. The upper portion 657 can include a plurality of detents or catches 671 and the retainer member 667 can include a plurality of corresponding locking apertures 673 extending between the top and bottom surface of the retainer member 667. The locking apertures 673 can engage the detents 671 of the upper portion 657 when the retainer member 667 is positioned on the upper portion 657 so that the retainer member 667 snaps over the upper portion 657 of the valve body 645 and is locked thereon.

Raised portions 675 can be situated between the detents 671, providing a support surface for the retainer member 667 when the retainer member 667 is snapped over the upper portion 657. This arrangement can help ensure that the distance from the valve sealing surface to the retainer member 667 is controlled, which acts to control compression of the sealing member 663 and thereby the valve cracking pressure. Alternatively, the retainer member 667 may be integral to the valve body 645. For example, the retainer member 667 could be integrated into the valve body 645 via a hinged snap.

The pressure relief valve 643 is movable between the closed position, wherein the third port 651 is sealed by sealing member 663, and the open position, wherein the third port 651 is unsealed, such that air or other fluids may flow, from the inflatable bladder 607 and/or pump 613 through the first and second fluid pathway 653, 655 to atmosphere.

When the sealing member 663 is mounted in the valve seat 661, the sealing member 663 can have a generally convex shape that flattens out against the valve seat 661 to create a certain sealing force that maintains the pressure relief valve 643 in the closed position. The sealing member 663 can use at least in part its elastic material properties and its preloaded convex shape to create the sealing force against the valve seat 661.

When the internal pressure within the inflation system 601 or head pressure creates enough force to lift or pop the sealing member 663 from the valve seat 661 of the upper portion 657, the third port 651 is unsealed and air can be vented from the inflatable bladder 607 and/or inflation system 601 to atmosphere. The stem 665 of the sealing member 663 positioned within the retainer member 667 can form a hinge about which disc portion of the sealing member 663 pops between its convex shape and a more flattened or concave shape in which the disc portion of the sealing member 663 lifts away from the valve seat 661 of the upper portion 657.

The pressure at which the sealing member 663 lifts off of the valve seat 661 is called the cracking pressure. When the head pressure is less than the cracking pressure, the sealing member 663 can automatically pop back closed. The cracking pressure of the pressure relief valve 643 can be greater than about 40 mmHg, about 50 mmHg, about 55 mmHg, about 60 mmHg, or about 65 mmHg. In other embodiments, the cracking pressure of the pressure relief valve 643 can be between about 40 mmHg and about 70 mmHg, about 45 mmHg and about 65 mmHg, or about 50 mmHg and about 60 mmHg. In other embodiments, the cracking pressure may be greater or lower. The cracking pressure of the pressure relief valve 643 can be set or varied by varying the shape and/or elastomeric properties of the sealing member 663.

The cracking pressure of the pressure relief valve 643 can be selected, set, or adjusted to generally correspond to a selected pressure limit within the inflatable bladder 607. The selected pressure limit can comprise a safe operating pressure, a therapeutic pressure, an activity specific pressure, a treatment pressure, or any other suitable pressure limit.

Alternatively, the retainer member 667 can be threadedly attached to the upper portion 657 of the valve body 645 such that the height of the retainer member 667 relative to the sealing member 663 can be adjusted, which, in turn, can influence the cracking pressure of the sealing member 663 by adjusting the force exerted on the sealing member 663 by the retainer member 667. Thus, the cracking pressure can be adjusted by adjusting the position of the retainer member 667 relative to the sealing member 663. The cracking pressure adjustment can be made by the user based on their activity level. For instance, a higher pressure setting could be used for periods of high activity like walking, while a lower pressure setting could be used for periods of rest.

In use, when the inflatable bladder 607 is inflated to point where the internal pressure within the inflation system 601 or head pressure on the sealing member exceeds the cracking pressure of the pressure relief valve 643, the pressure relief valve 643 can automatically move to the open position, thereby expelling or releasing air from the inflation system 601 and/or inflatable bladder 607 to atmosphere through the third port 651 of the pressure relief valve 643. As air is released from the inflation system 601, the internal pressure within the inflation system 601 can drop below the cracking pressure of the pressure relief valve 643 such that the pressure relief valve 643 automatically returns to the closed position, thereby resealing the inflation system 601.

Because the pressure relief valve 643 automatically limits or regulates the level of pressure within the inflation system 601, the pressure relief valve 643 can reduce the likelihood that a user will over-inflate the inflatable bladder 607. This is advantageous because users of walkers and other orthopedic devices, especially diabetic patients, often experience reduced sensation in their extremities, which can result in them inadvertently over-inflating the inflatable bladder 607. Such over-inflation can cause pressure on the skin, which can reduce both capillary blood flow to the skin and arterial flow to the anatomical member. Thus, by limiting or automatically regulating the level of pressure within the inflatable bladder 607 and/or inflation system 601, the pressure relief valve 643 eliminates or reduces the likelihood of over-inflation that can harm the user.

In addition, the pressure relief valve 643 can automatically release excess pressure within the inflation system 601 resulting from other factors, such as, for example, changes in ambient pressure due to a change in altitude. The pressure relief valve 643 also reduces the need for users themselves to set or monitor safe pressure levels within the inflation system 601. For example, conventional inflation systems often require patients to monitor pressure in the system using a pressure gauge attached to a pump. However, many patients, especially diabetic patients, do not see well enough to read the pressure gauge and pressure gauges are known to malfunction. Consequently, such patients tend to over-inflate the inflatable bladder causing injury to the patient. By including the pressure relief valve 643 in the inflation system 601, the patient/user can inflate the inflatable bladder 607 without the need of reading a pressure gauge or the risk of over-inflation.

The configuration of the pressure relief valve assembly 609 described herein is to be regarded as exemplary only, as any suitable configuration of the pressure relief valve assembly is possible. For example, the pressure relief valve 643 can be a spring-loaded over-pressure relief valve, a check valve, a swing-check valve, a diaphragm valve, a ball valve, luer check valves, miniature check valves, or any other suitable valve. In other embodiments, the pressure relief valve 643 can include, but is not limited to the Series 500 Miniature Check Valves, commercially available from Smart Products, Inc., Morgan Hill, Calif., which are incorporated herein, in their entirety, by this reference. Of course, other pressure relief valves may be employed.

Figure 24:
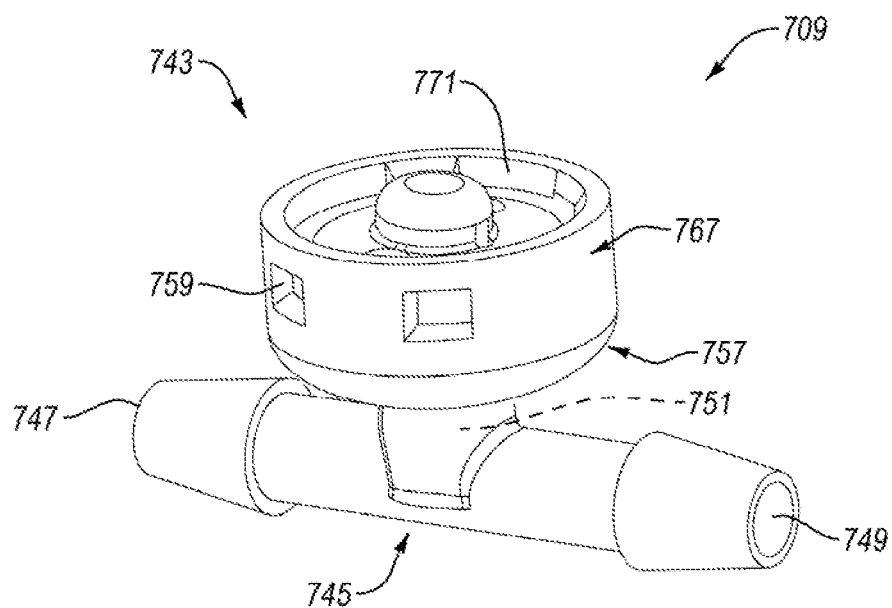
FIG. 24 is a side isometric view of a pressure relief valve assembly according to another embodiment.
Figure 25:
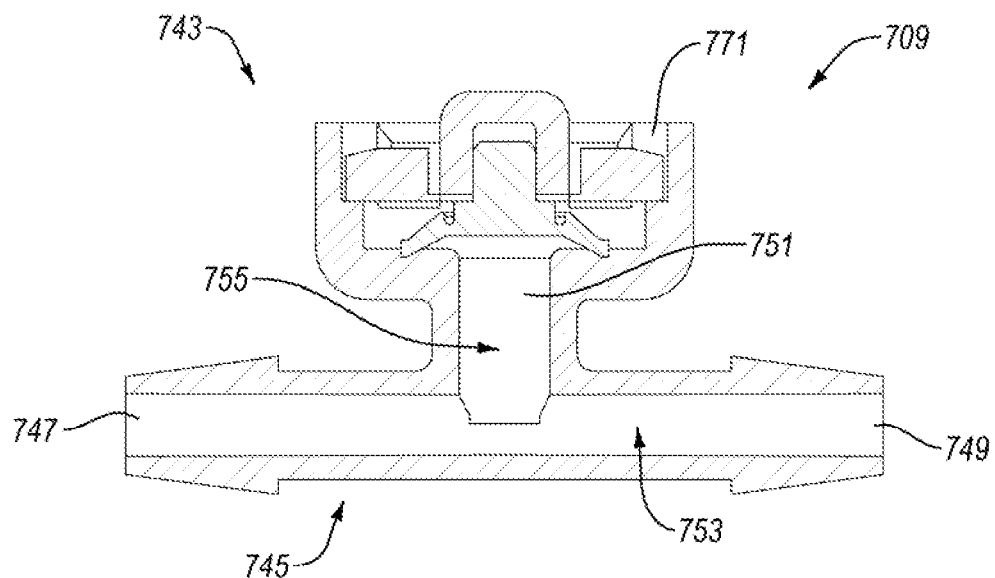
FIG. 25 is a cross sectional view of the pressure relief valve assembly shown in FIG. 24.

Another exemplary embodiment of a pressure relief valve assembly 709 is illustrated in FIGS. 24 and 25. The pressure relief valve assembly 709 can comprise a pressure relief valve 743 similar to the pressure relief valve 643, except that retainer member 767, upper portion 757, and second port 749 exhibit a different configuration. As seen, the upper portion 757 can comprise a hollow substantially cylindrical member having a generally solid sidewall. The upper portion 757 can include vent openings 759 formed in the sidewall for venting air the atmosphere. The inner surface of the upper portion 757 can include a plurality of catches 771 formed thereon, each including a generally planar bottom surface area and an angled upper surface area. The retainer member 767 can comprise a disc-like member sized and configured to snap inside of the upper portion 757. When the retainer member 767 is inserted or snapped into the upper portion 757 of the valve body 745, the planar bottom surface areas of the catches 771 can form a stop by engaging the top surface of the retainer member 767 to lock the retainer member 767 within the upper portion 757.

The valve body 745 includes a first port 747, a second port 749, and a third port 751. A first fluid pathway 753 connects the first port 747 and the second port 749. A second fluid pathway 755 connects the first fluid pathway 753 and the third port 751.

Figure 26:
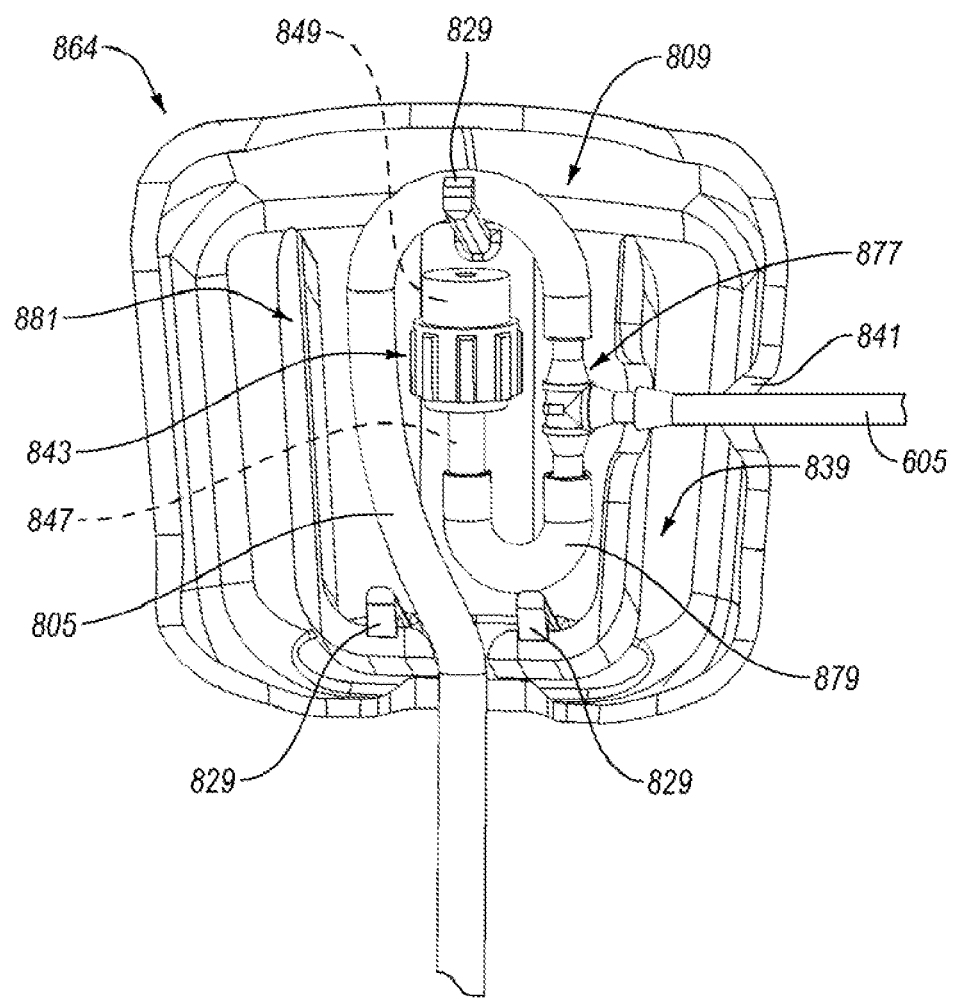
FIG. 26 is an isometric view of a pressure relief valve assembly and cover member according to another embodiment.

Another exemplary embodiment of a pressure relief valve assembly 809 and cover member 864 is illustrated in FIG. 26. The pressure relief valve assembly 809 includes a pressure relief valve 843, a fitting 877, a relief tube 879 connected to the pressure relief valve 843, and the inflation tube 605. The fitting 877 may have any suitable configuration. For example, the fitting 877 may be a tee-type fitting having a first port, a second port, and a third port. The fitting 877 can include a first fluid pathway may extend between the second port and the third port and a second fluid pathway extending between the first port and the first fluid pathway. In an embodiment, the first port of the fitting 877 is connected to the inflation tube 605 extending between to the pump assembly 603 and the fitting 877. The second port of the fitting 877 is connected to the inflation tube 605 extending through a tube hole 662 (shown in FIG. 27) and between the fitting 877 and the inflatable bladder 607. As shown, the inflation tube 605 can be routed such that it at least partially loops around the pressure relief valve assembly 609. The third port can be connected to the relief tube 879 extending between the fitting 877 and the pressure relief valve 843.

The pressure relief valve 843 can exhibit any suitable configuration. For example, the pressure relief valve 843 can include a valve body having a valve seat, a first port 847, a second port 849, and a fluid pathway extending between the first port 847 and the second port 849.

The pressure relief valve 843 can include a sealing member configured to cooperate with the valve seat in order to seal the second port 849. The pressure relief valve 843 is movable between a closed position, wherein the second port 849 is sealed by the sealing member, and an open position, wherein the second port 849 is unsealed, such that air may flow, for example, from the inflatable bladder 607 and/or pump assembly 603 to the atmosphere. The pressure at which the pressure relief valve 843 moves to the open position is the cracking pressure. In an embodiment, the sealing member can be biased against the valve seat to seal the second port 849 with the aid of a resilient retainer member. In other embodiments, the sealing member can be held within the valve body by a retainer member and the sealing member can be configured to seal the second port 849 based on the material properties and/or shape of the sealing member.

The pressure relief valve 843 can include means to adjust the resilient force applied to the sealing member, such as a dial on the posterior of the base shell 602. The dial may be positioned on the base shell 602, integrated with the cover member 664, or in any other suitable location. By adjusting the resilient force, the cracking pressure of the pressure relief valve 843 adjusts. Thus, the dial may have different settings such as high pressure, medium pressure, and low pressure. A user, clinician, or medical professional can select, set, or adjust the cracking pressure to customize the inflation system 601 for different users and/or user needs.

The cover member 864 can be similar to the cover member 664 except that the cover member 864 is larger and includes a u-shaped inner wall 881 formed on the bottom of the recess 839. The u-shaped inner wall 881 can be arranged to provide additional support and/or protection to the pressure relief valve assembly 809. The u-shaped inner wall 881 may include side openings 841 formed along the rim thereof arranged to accommodate and/or receive the inflation tubes 605. The inner wall 881 can also help align the cover member 864 with the base shell 602. For instance, the inner wall 881 can fit into a corresponding groove or recess formed on the base shell 602. This arrangement can eliminate the need of hook members or snaps to withstand transverse loading.

A plurality of hook members 829 can be formed on and extending from the bottom of the recess 839. The hook members 829 can be arranged to selectively snap into the cutout 631. As shown, at least one of the hook members 829 can provide a support or guide for the inflation tube 605 extending between the fitting 877 and the inflatable bladder 607. It will be appreciated that the cover member 864 can exhibit any suitable configuration.

Figure 27:
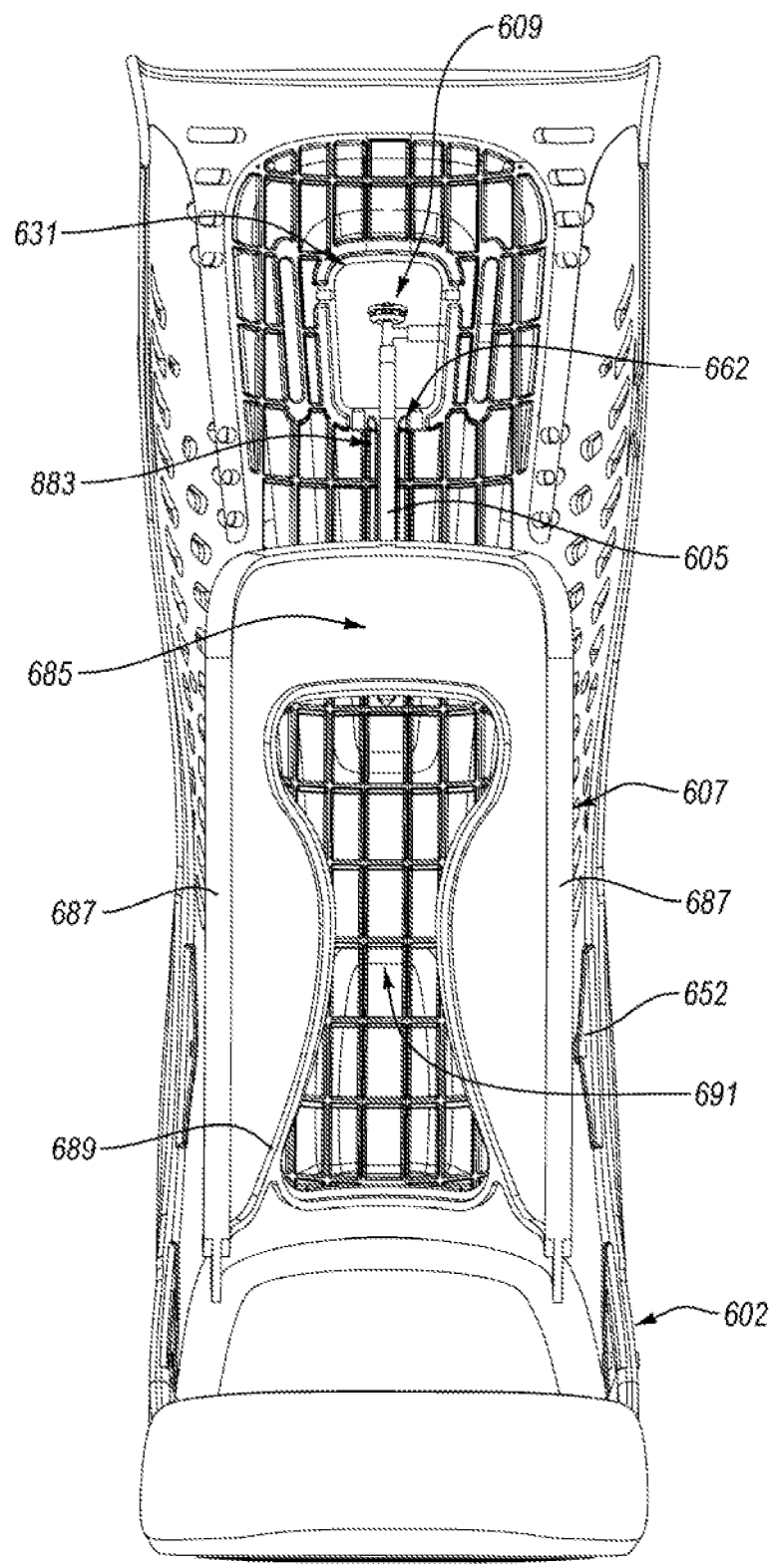
FIG. 27 is a front view of the base shell shown in FIG. 15 with the liner removed, showing the bladder.

FIG. 27 illustrates the base shell 602 with the liner removed for simplicity. As seen, the posterior of the base shell 602 can include another tube hole 662 formed in a bottom wall of the cutout 631 that is in communication with the interior of the walker 600. The tube hole 662 can exhibit any suitable configuration.

The inflation tube 605 connecting the pressure relief valve assembly 609 and the inflatable bladder 607 can be inserted through the tube hole 662 to the interior of the base shell 602 where an indentation or groove 883 can be formed for guiding the inflation tube 605 to the inflatable bladder 607. The groove 883 can have any suitable configuration. For example, the groove 883 can extend from the tube hole 662 to a point below the terminal edge of the inflatable bladder 607.

Routing the inflation tube 605 through the groove 883 on the interior of the base shell 602 can help reduce or eliminate pressure points on the interior of the walker 600, which can be both uncomfortable as well as a risk for resulting in pressure ulcers. Guiding the inflation tube 605 in the groove 883 can also protect the inflation tube 605 from being inadvertently crushed or pinched. In other embodiments, the inflation tube 605 can be covered or secured into the groove 883 using adhesive tape, a separate cover component, or any other suitable means. As seen, the inflatable bladder 607 can be arranged within the posterior of the base shell 602 such that when the inflatable bladder 607 is inflated, the inflatable bladder 607 can support the lower leg, ankle, and/or foot.

The inflatable bladder 607 can be arranged in the ankle receiving portion of the base shell 602 and generally shaped to correspond to the posterior, medial, and lateral side of the base shell 602. As noted above, observation holes 652 can be formed in the wing portions 610 of the base shell 602, allowing for tactile and/or visual confirmation that the inflatable bladder 607 is properly inflating or inflated.

The inflatable bladder 607 can include a posterior portion 685 and wing portions 687. The inflatable bladder 607 can be formed of two sheets of air impervious plastic material that is welded around the edges to create air chambers therebetween. Optionally, perspiration wicking material can be applied to the surfaces of the inflatable bladder 607 that are configured to contact the wearer's anatomy.

The inflatable bladder 607 can be attached to the base shell 602 and/or liner 612 by a hook-and-loop type system, a snap-fit system, combinations thereof, or any other suitable attachment system. For example, a portion of the inflatable bladder 607 can be covered with a loop material (e.g., UBL loop) to make it easily attachable to a corresponding hook material on the base shell 602. In other embodiments, the inflatable bladder 607 can snap into or onto the base shell 602. Welds and/or holes 689 can be arranged in the inflatable bladder 607 to serve a number of functions. For example, the welds 689 in the inflatable bladder 607 can be configured to direct airflow within the inflatable bladder and also to provide heat and perspiration wicking channels along the surfaces of the inflatable bladder 607.

The inflatable bladder 607 can include a central opening 691 having an hour-glass like shape. The central opening 691 can be configured to receive and support the Achilles tendon so that the lower leg fits snugly within the walker 600, and the ankle is securely positioned within the walker 600. In other embodiments, the inflatable bladder 607 may include longitudinally extending openings (not shown) that provide venting for heat and perspiration. Moreover, the posterior of the inflatable bladder 607 can include a bridge portion that includes an inlet for the inflation tube 605 and this is in fluid communication with the lateral and medial sides of the inflatable bladder 607. Such a configuration can help the inflatable bladder 607 inflate more equally, reducing the likelihood that one side inflates faster than the other side.

The shape of the inflatable bladder 607 can further be configured to focus compression where it is needed and uniform compression is provided to areas of the anatomy where the inflatable bladder 607 provides compression. In other embodiments, the shape of the inflatable bladder 607 can be configured to create specific areas of pressure off-loading. The inflatable bladder 607 can be encased within a fabric covering, providing increased comfort to a user.

It will be appreciated that while a single inflatable bladder is described, the walker 600 can include any suitable number of inflatable bladders. For example, in an embodiment, the walker 600 can include separate medial, lateral, and dorsal bladders. Moreover, while the inflatable bladder is described being inflated with air, it will be appreciated that the inflatable bladder can be filled with any suitable material or fluid. For example, the inflatable bladder 607 can be selectively filled with gel, foam, water, silicone, combinations thereof of the like. Moreover, in other embodiments, the inflatable bladder 607 can be included as part of a liner within the walker 600. In other embodiments, the inflatable bladder 607 is separate from a liner within the walker 600. Such a configuration may facilitate removal the liner for washing or replacement.

While the inflation system 601 is shown with the walker 600, it will be appreciated that the exemplary embodiments of the inflation system can be incorporated and/or used with a number of different orthopedic devices. For instance, exemplary embodiments of the inflation system can be used with a short leg walker, an ankle walker, a strut walker, a fracture walker, an Achilles walker, or any other suitable orthopedic device. In other embodiments, the inflation system 601 can be integrated with a system providing Deep Vein Thrombosis ("DVT") therapy.

Figure 28:
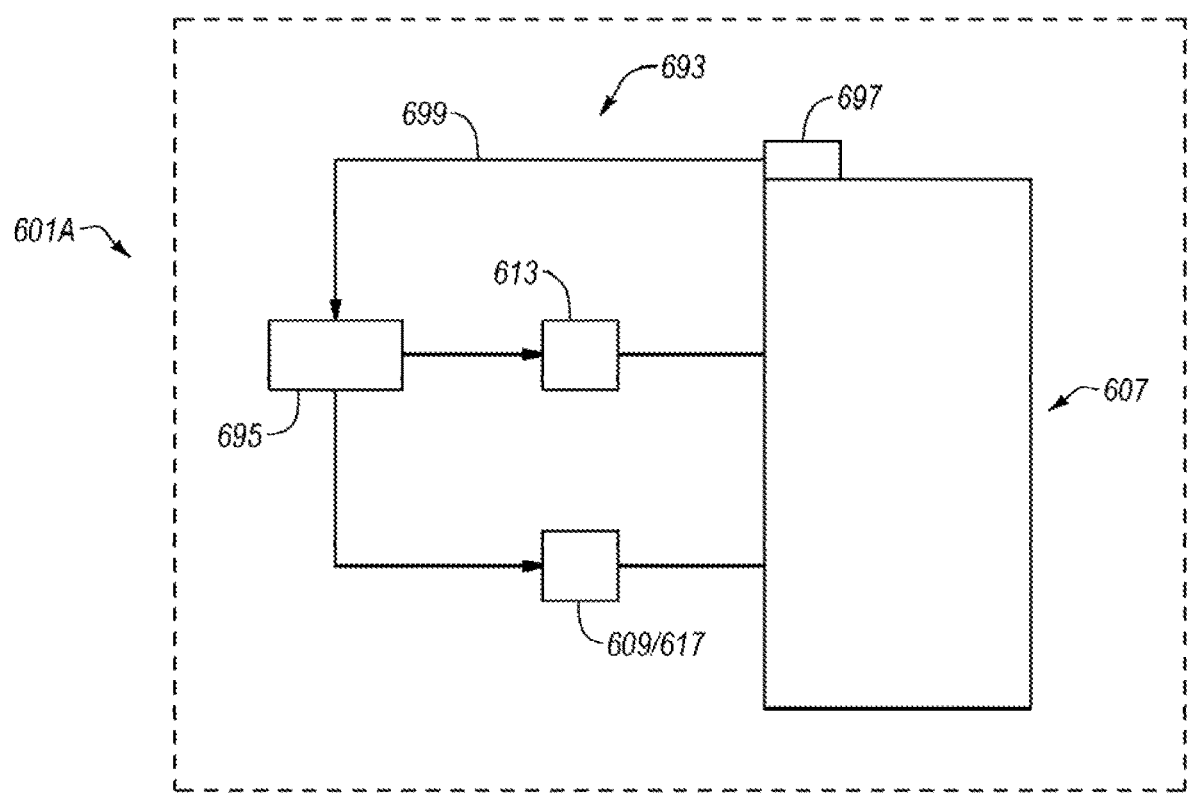
FIG. 28 is a schematic diagram of an inflation system according to another embodiment.

In other embodiments, the inflation system 601 can be arranged to control the amount of pressure within the inflation system 601 based on sensed conditions. As seen in FIG. 28, an inflation system 601A according to another embodiment can include a pressure regulation system 693 having a control unit 695 and one or more sensors 697 arranged to sense pressure within the inflatable bladder 607 and/or inflation system 601 and to send one or more sensing signals 699 to the control unit 695. The sensing signals 699 can include information about pressure levels within the inflatable bladder 607 and/or inflation system 601. The control unit 695 can be operably connected to the pump 613 and the release valve 617 and/or the pressure relief valve assembly 609 such that the control unit 695 can direct the pump the 613 to inflate the inflatable bladder 607 and the release valve 617 and/or the pressure relief valve assembly 609 to deflate the inflatable bladder 607 in response to the pressure information received from the one or more pressure sensors 697.

For instance, the one or more sensors 697 can detect strain (or deflection) due to pressure over an area in the inflatable bladder 607 and/or the inflation system 601. The one or more sensors 697 can convert this pressure energy to the one or more sensing signals 699 in the form of electrical energy. One or more analog-to-digital converters (ADC) convert the electrical energy to digital data that is provided to the control unit 695. The ADC can be a separate component, can be integrated into the control unit 695, or can be integrated into the one or more sensors 697. The control unit 695 can include processing hardware (e.g., processing electrical circuitry) and an operating system configured to run one or more application software programs. The control unit 695 can use one or more processing techniques to analyze the digital data in order to determine pressure levels within the inflatable bladder 607 and/or inflation system 601. Responsive to the one or more sensing signals 699 output by the one or more sensors 697, the control unit 695 (including control electrical circuitry) can direct the pump 613 to inflate the inflatable bladder 607 or the release valve 617 to deflate the inflatable bladder 607, automatically controlling safe pressure levels within the inflation system 601. In other embodiments, the control unit 695 can direct the pressure relief valve assembly 609 to deflate the inflatable bladder 607 responsive to the one or more sensing signals 699.

Figure 30:
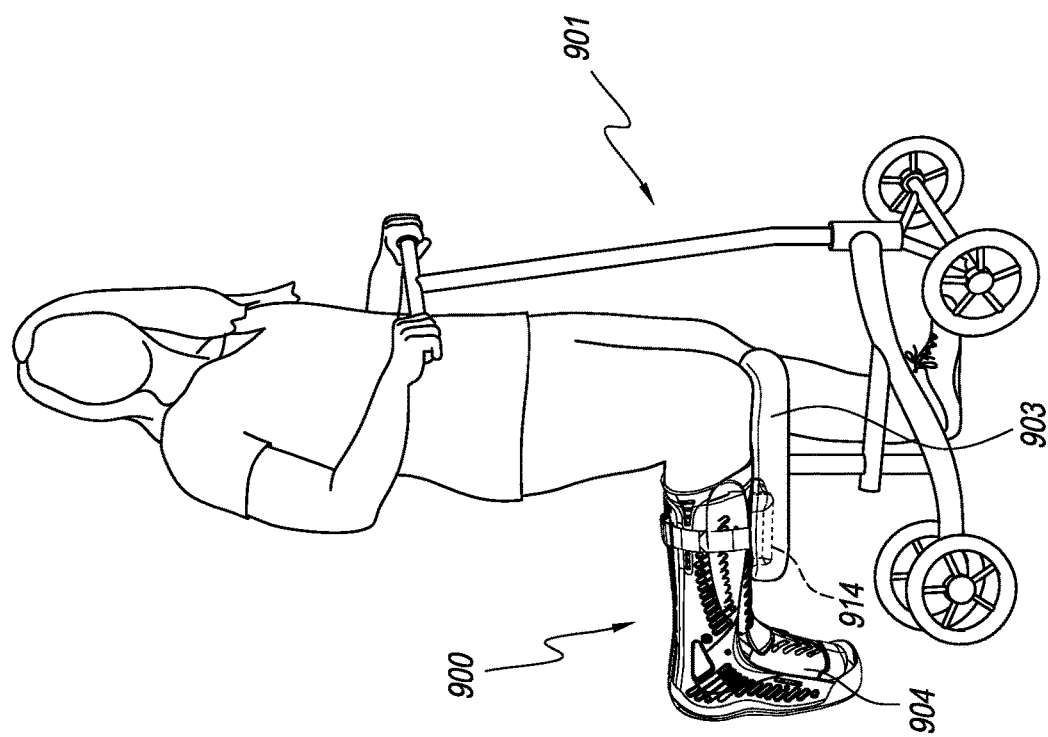
FIG. 30 is a schematic diagram of the orthopedic device in FIG. 29 positioned on a knee scooter.
Figure 29:
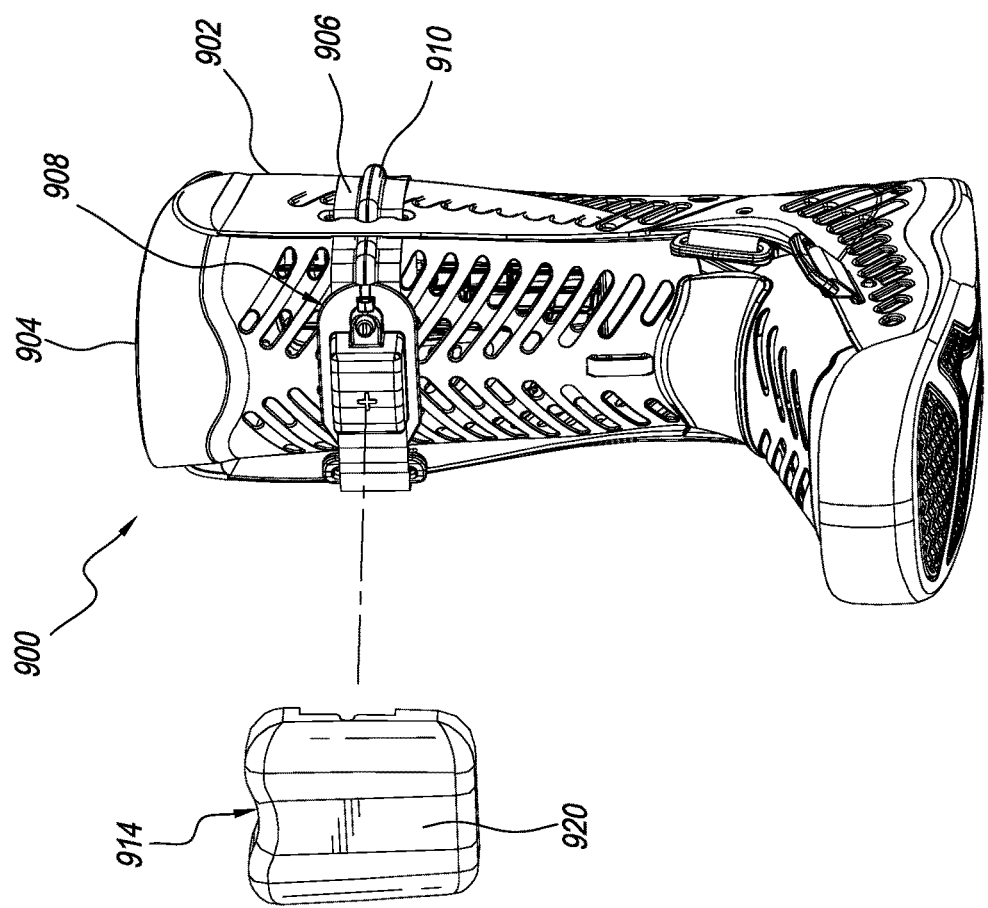
FIG. 29 is a front isometric view of an orthopedic system according to another embodiment.
Figure 31:
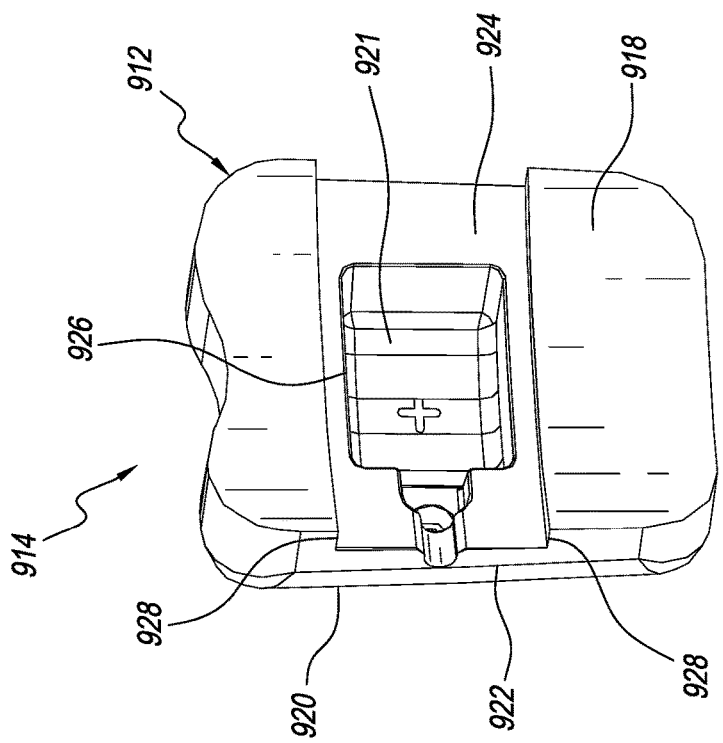
FIG. 31 is a back isometric view of the protective part in FIG. 29 removed from the orthopedic device for ease of reference.

Another exemplary embodiment of an orthopedic device comprising a walker 900 is shown in FIGS. 29-31. Similar to the other embodiments, the walker 900 includes complementary base and dorsal shells 902, 904 and at least one strap 906 arranged to bring the base shell 902 and the dorsal shell 904 closer together. The at least one strap 906 can comprise an upper strap arranged to extend over a patient's lower leg. A pump assembly 908 is attached to and/or carried by the at least one strap 906 along the anterior aspect of the walker 900 and an inflatable bladder can be arranged in an ankle receiving portion of the walker 900 and inflated and/or deflated via one or more inflation tubes 910, which are in fluid communication with the pump assembly 908. The pump assembly 908 can include a pump to increase pressure within the inflatable bladder and a release valve arranged to selectively release pressure within the inflatable bladder.

As can be seen from the figures, this embodiment includes a protective part 914 securable over the pump assembly 908 of the walker 900. The protective part 914 is arranged to protect the pump assembly 908 from damage and/or inadvertent operation due to contact with external objects. For instance, walkers are commonly used in combination with a knee scooter 901 (or knee walker or a platform walker) as shown in FIG. 30. A knee scooter 901 allows a patient to propel oneself with one leg, while the patient's affected leg rests on a support platform 903 of the knee scooter 901.

As seen in FIG. 30, when riding a knee scooter 901, the patient typically positions the anterior aspect of the walker 900 on the support platform 903 to support the weight of the patient on the knee scooter 901. With the pump assembly 908 positioned on the anterior aspect of the walker 900, the weight of the patient on the walker can force or compress the pump assembly 908 against the support platform 903 of the knee scooter, which, in turn, can damage or inadvertently operate the pump assembly. This can be problematic because it can damage the pump assembly and/or over inflate the inflatable bladder inside the walker, which can cause pressure on the skin and reduce both capillary blood flow to the skin and arterial flow to the affected limb. This can also be problematic because it can under inflate the inflatable bladder in the walker, which can result in a poor fit and/or inadequate support for the affected limb. Also problematic is that leaning on the anterior aspect of the walker 900 can deflate the inflatable bladder by depressing the release valve.

The protective part 914 advantageously protects the pump assembly 908 from damage and/or inadvertent operation by providing a physical barrier between the pump assembly 908 and an external object (e.g., the support platform 903). For instance, when the anterior aspect of the walker 900 is positioned on the support platform 903, the rigidity of the protective part 914 distributes the user's weight on the walker 900 away from the pump assembly 908 and directly to the support platform 903, eliminating or substantially reducing any load on the pump assembly 908 from the patient's weight. This advantageously protects the pump assembly 908 from being inadvertently compressed between the walker 900 and the support platform 903, reducing the likelihood of the pump assembly 908 being damaged or undesirably operated, which in turn, increases patient safety, convenience, and freedom to use the walker 900 with a knee scooter.

The protective part 914 protects the pump assembly 908 without substantially affecting the functionality of the walker 900. It also does so without the use of complicated and bulky components. Furthermore, the protective part 914 can be a separate add-on component to the walker and can be adapted to fit a number of different orthopedic devices, providing versatility.

As shown in FIG. 31, the protective part 914 can include a semi-rigid or rigid body 912 defining an inner surface 918 arranged to engage and/or face the dorsal shell 904, an outer surface 920 opposite the inner surface 918, and side surfaces 922 extending between the inner and outer surfaces 918, 920. The body 912 is formed of at least one material having a rigidity or strength selected to resist impact loads and/or sustained loads when it is secured on the walker 900. The body 912 can be formed of plastic, foam, carbon fiber, metal, combinations thereof, or any other material which would provide sufficient strength to resist undesirable deformation during use. In an embodiment, the body 912 can be formed of a high density foam so that it can provide some cushioning and/or shock absorption. For instance, the body 912 can include high density foam having a Shore A hardness between about 30 and about 50. In other embodiments, the body 912 can include a high density foam having a higher or lower Shore A hardness.

The body 912 extends proximally and distally of the pump assembly 908. The body 912 can be secured over the pump assembly 908 in any suitable manner. For instance, the body 912 can be removably secured over the pump assembly 908 via an interference fit between the body 912 and the pump assembly 908. This allows the body 912 to be easily secured over the pump assembly 908 as needed and easily removed. In other embodiments, the body 912 can be secured over the pump assembly 908 via fasteners, hook-and-loop type systems, clips, magnets, adhesives or any other suitable securing system. The body 912 can be attached to the at least one strap 906. The body 912 can be directly attached to the dorsal shell 904.

The outer surface 920 of the body 912 can be continuous or interrupted. The outer surface 920 can provide a support area for the body 912 when it is engaged with a support platform or other external object. It will be appreciated that the body 912 can be oversized relative to the pump assembly 908, helping to distribute forces through the body 912 away from the pump assembly 908.

The inner surface 918 of the body 912 can be contoured to generally correspond to the contour of the anterior of the dorsal shell 904. This can allow the body 912 to form a better fit between the protective part 914 and the dorsal shell 904. The inner surface 918 can also provide a support area for the body 912 against the dorsal shell 904 when the protective part 914 is engaged with the dorsal shell 904.

As seen in FIG. 31, a cutout portion 924 is formed in the inner surface 918 that extends between the side surfaces 922. The cutout portion 924 can have a rectangular shape or any other shape arranged to accommodate a portion of the at least one strap 906, facilitating the securement of the body 912 over the pump assembly 908. The cutout portion 924 can terminate at upper and lower abutments 928. The cutout portion 924 can taper in a direction toward the dorsal shell 904, allowing the upper and lower abutments 928 to engage with the inner surface of the upper and lower edges of the pump assembly 908 to secure to the body 912 over the pump assembly 908.

A receiving space or cavity 926 is defined in the cutout portion 924. The cavity 926 is arranged to accommodate at least part of the pump assembly 908, allowing the control features of the pump assembly 908 to be recessed within the body 912. Optionally, the cavity 926 can include a side opening for accommodating an inflation tube in fluid communication with the pump assembly.

The cutout portion 924 and/or the cavity 926 also facilitates alignment of the body 912 with the pump assembly 908. For instance, the pump assembly 908 and the inflation tube 910 can fit into the cavity 926 to ensure the body 912 is properly positioned. When the body 912 is secured over the pump assembly 908, the pump assembly 908 is positioned within the cavity 926 and the body 912 keeps compressive forces exerted on the body 912 away from the control features of the pump assembly 908.

In use, when a patient positions the anterior aspect of the dorsal shell 904 on the support platform 903 of the knee scooter 901, the rigidity of the body 912 generally resists deformation and distributes the weight of the patient from the dorsal shell 904 through the body 912 away from the pump assembly 908 and to the support platform 903. The body 912 thus beneficially protects the pump assembly 908 from damage and/or inadvertent operation when the walker 900 is used with a knee scooter, making the walker 900 safer and more versatile.

Figure 32:
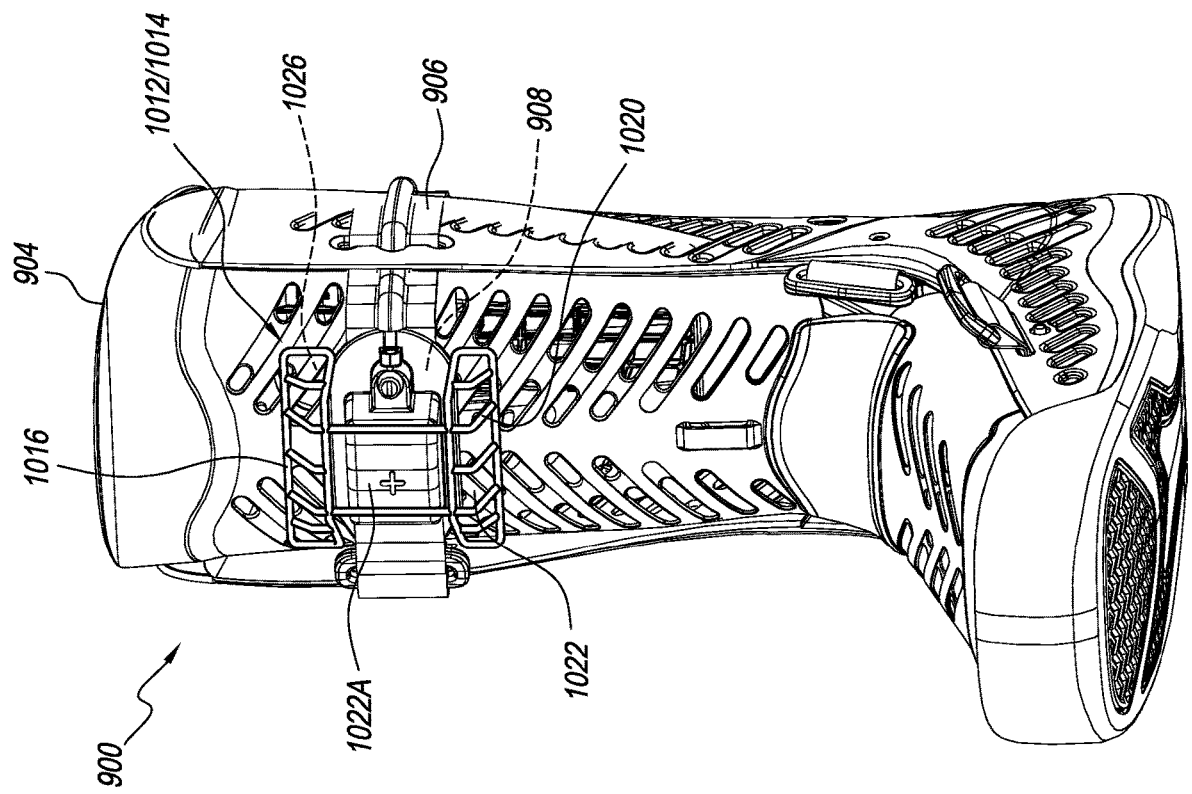
FIG. 32 is a front isometric view of an orthopedic system according to another embodiment.

FIG. 32 shows another embodiment of a protective part 1012 for protecting the pump assembly 908 from damage or inadvertent operation. The protective part 1012 comprises a wire structure 1014 extending over the pump assembly 912. The wire structure 1014 includes a base frame 1016 and a plurality of intersecting wire members 1020 defining openings 1022 and extending over and across the pump assembly 908. The wire members 1020 collectively define a receiving space or cavity 1026 for receiving or accommodating at least part of the pump assembly 908 when the wire structure 1014 is secured on the walker 900. The wire structure 1014 can be made of metal, plastic, rubber, carbon, combinations thereof, or any other suitable materials.

The wire structure 1014 has a rigidity arranged to distribute pressure from the patient or another external object away from the pump assembly 908. The wire structure 1014 extends proximally and distally of the pump assembly 908. The wire structure 1014 can be secured over the pump assembly 908 in any suitable manner but is shown being secured over the pump assembly 908 by feeding or threading the at least one strap 906 and the pump assembly 908 through at least two of the openings 1022 so that the base frame 1016 of the wire structure 1014 is secured between the at least one strap 906 and the dorsal shell 904.

One or more access openings 1022A in the wire structure 1014 can be sized and arranged so that a patient can manipulate the control features of the pump assembly 908 through the wire structure 1014 while it is secured over the pump assembly 908. This allows the wire structure 1014 to both protect the pump assembly 908 from inadvertent operation and provide operational access to the patient and/or clinician. While the protective parts 914, 1012 are shown for use with the walker 900, it will be appreciated that the exemplary embodiments of the protective part can be incorporated and/or used with a number of different orthopedic devices.

Figure 33:
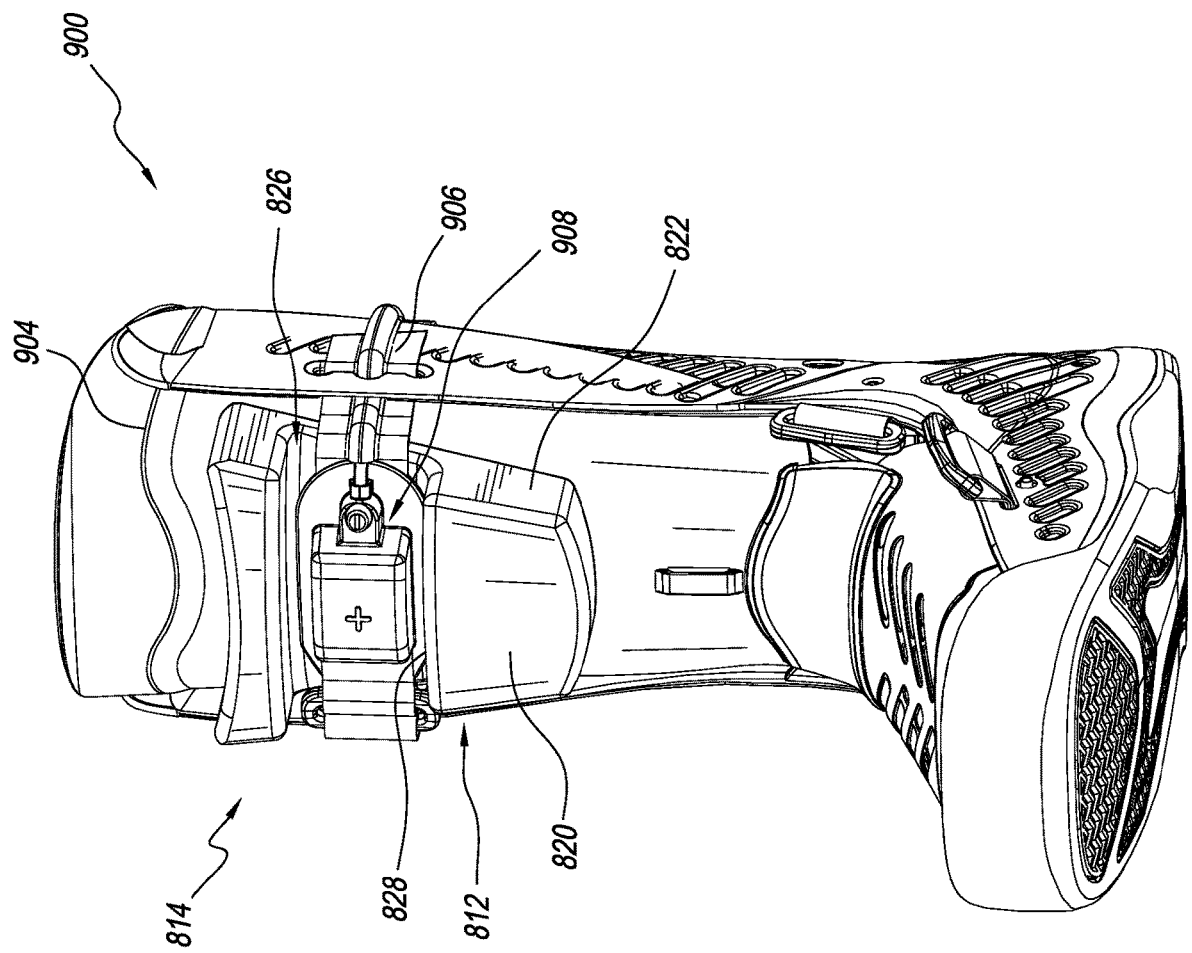
FIG. 33 is a front isometric view of an orthopedic system according to another embodiment.
Figure 37:
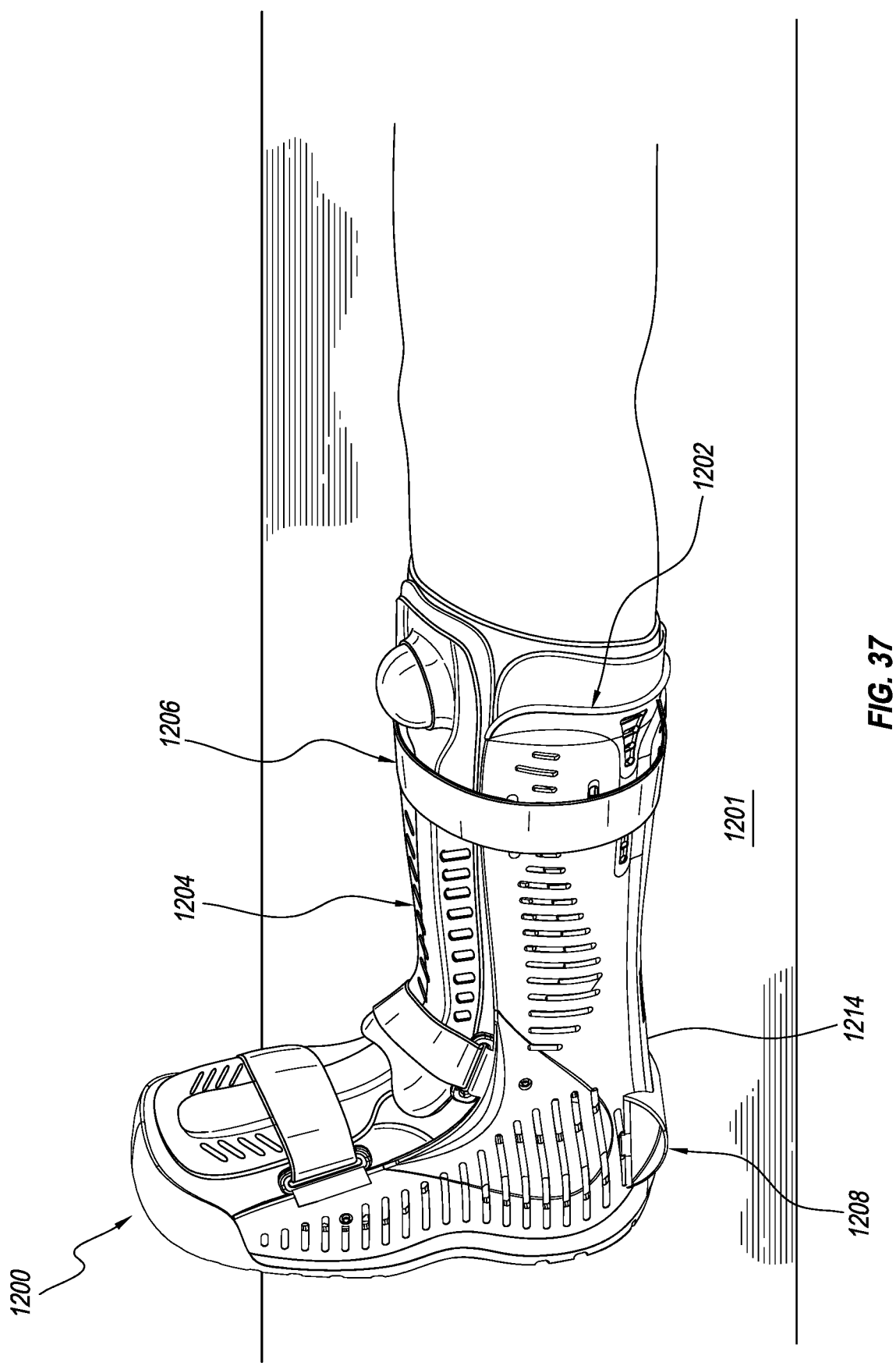
FIG. 37 is a side isometric view of an orthopedic system according to another embodiment.
Figure 38:
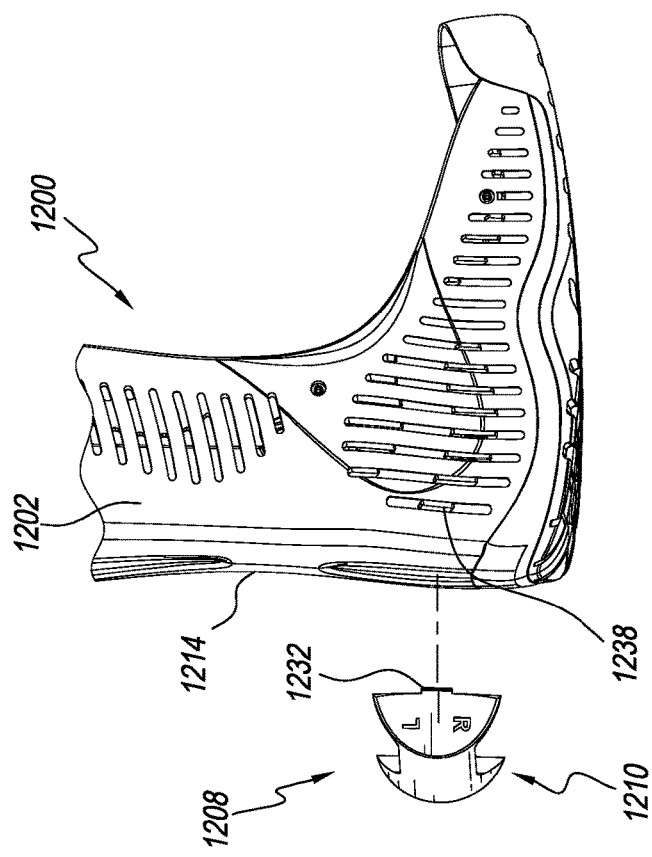
FIG. 38 is a partial exploded view of the orthopedic device and stabilizing part in FIG. 37.

FIG. 33 shows another embodiment of a protective part protective part 814 for protecting the pump assembly 908 from damage or inadvertent operation. The protective part 814 comprises a body 812 defining an inner surface arranged to engage and/or face the dorsal shell 904, an outer surface 820 opposite the inner surface, and side surfaces 822 extending between the inner surface and the outer surface 820. The body 812 can be formed of any of the materials previously described. For instance, the body 812 can be formed of a high density foam. The inner surface of the body 812 can be contoured to generally correspond to the contour of the anterior of the dorsal shell 904. The inner surface of the body 812 can be permanently attached or integral to the anterior of the dorsal shell 904. The inner surface of the body 812 can be removably secured to the anterior of the dorsal shell 904 under the at least one strap 906.

The outer surface 820 of the body 812 can provide a support area for the body 812 when it is engaged with a support platform or other external object. As seen, the body 812 can be oversized relative to the pump assembly 908, helping to distribute forces through the body 812 away from the pump assembly 908. A receiving space or cavity 826 is defined in the outer surface 820 for accommodating at least part of the pump assembly 908. The cavity 826 is sized and configured such that the pump assembly 908 can be generally recessed within the cavity 826 relative to the outer surface 820 of the body 812. As such, the body 812 can both provide protection to the pump assembly 908 and allow a patient or clinician to manipulate the control features of the pump assembly 908 while the protective part 814 is secured under the at least one strap 906.

In an embodiment, the cavity 826 can extend completely through the side surfaces 822 of the body and can terminate at upper and lower abutments 828, helping to facilitate alignment of the protective part 814 and the pump assembly 908. The cavity 826 can have any suitable shape but is shown to have a generally rectangular shape.

FIGS. 34-36 illustrate another embodiment of a protective part 1112 for protecting a pump assembly on a walker 1100 from damage or inadvertent operation. FIGS. 34-36 show a partial dorsal shell 1102 of the walker 1100, which is removed from the base shell for ease of reference. The dorsal shell 1102 can be formed either in a single piece or in multiple shell portions. In the exemplary embodiment, the dorsal shell 1102 includes a proximal shell portion 1104 that is connected to a distal shell portion via a flexible or resilient portion or hinge connection 1108.

The dorsal shell 1102 can include a reinforcing portion 1110 that extends generally longitudinally along the dorsal shell 1102 to selectively strengthen the dorsal shell 1102. The reinforcing portion 1110 can be formed in a single piece and from the same material as the dorsal shell 1102. In addition to adding structural support, the reinforcing portion 1110 can also enhance the low profile form of the walker 1100. The reinforcing portion 1110 can further provide additional support for engaging straps extending across the dorsal shell 1102.

The dorsal shell 1102 also includes a pump receiving opening 1116. The pump receiving opening 1116 is shown formed in the reinforcing portion but can be formed in any portion of the dorsal shell 1102. A pump assembly comprising a flexible bulb type pump and push button release valve can be inserted through the pump receiving opening 1116.

The dorsal shell 1102 can include clearance holes 1114 defined therein. The clearance holes 1114 can be arranged in any suitable pattern. For instance, the clearance holes 1114 may be arranged at an oblique angle relative to the reinforcing portion 1110 and may exhibit different sizes. The clearance holes 1114 can reduce the weight of the walker 1100. Further, the clearance holes 1114 can act as vents to allow heat and perspiration to pass from inside the walker 1100 to the exterior thereof. Additionally, the clearance holes 1114 may also allow the dorsal shell 1102 to have some additional resiliency to accommodate swelling of a limb or users having different sizes of lower legs, ankles, and feet.

The protective part 1112 can be similar to the protective part 914 except that the protective part 1112 is arranged to be selectively secured over a pump assembly extending through the pump receiving opening 1116 on the dorsal shell 1102. The protective part 1112 comprises a semi-rigid or rigid body 1118 defining an inner surface 1120 arranged to face the dorsal shell 1102, an outer surface 1122 opposite the inner surface 1120, and side surfaces 1124 extending between the inner and outer surfaces 1120, 1122. The body 1118 can have an elongate configuration extending in a longitudinal direction along the dorsal shell 1102. The body 1118 can extend proximally and distally of the pump assembly.

The outer surface 1122 can be continuous or interrupted. The inner surface 1120 can be contoured to generally correspond to the anterior of the dorsal shell 1102. This can allow the body 1118 to form a better fit between the body 1118 and the dorsal shell 1102. The inner surface 1120 can also provide a support area for the body 1118 against the dorsal shell 1102 when the body 1118 is secured over a pump assembly extending through the pump receiving opening 1116. The inner surface 1120 of the body 1118 can engage the dorsal shell 1102 on opposing sides of the reinforcing portion 1110 which, in turn, helps the body 1118 to distribute forces away from a pump assembly.

The inner surface 1120 defines a cutout portion 1128 arranged to receive the reinforcing portion 1110 of the dorsal shell 1102. This can help align the body 1118 with the pump assembly. For instance, the reinforcing portion 1110 can fit into the cutout portion 1128 to help ensure the pump assembly is properly positioned in the body 1118. The cutout portion 1128 can also help lower the profile of the body 1118 on the dorsal shell 1102.

A receiving space or cavity 1126 is defined in the cutout portion 1128. The cavity 1126 is arranged to receive or accommodate at least part of the pump assembly, allowing the pump assembly to be generally recessed within the body 1118.

Similar to the other embodiments, the body 1118 is securable over the pump assembly in any suitable manner and has a rigidity arranged to distribute pressure from the patient, walker, or another external object away from the pump assembly. The body 1118 can be removably secured directly to the dorsal shell 1102. For instance, the body 1118 can be removably secured to the dorsal shell 1102 via hook-and-loop type systems, magnets, adhesives, or fasteners. According to a variation, the body 1118 can be secured to the dorsal shell 1102 via a snap-type connection. The body 1118 can include a plurality of snaps or hook members integrally formed on the inner surface 1120 and configured to snap, lock or clip into one or more clearance holes 1114 formed in the dorsal shell 1102, facilitating assembly.

In other embodiments, the protective part can be permanently attached to the dorsal shell. For instance, the protective part can be a structure or body that is permanently and pivotally attached to the dorsal shell. The body can be arranged to pivot away from the dorsal shell to provide access to the pump assembly and to pivot toward the dorsal shell to conceal and protect the pump assembly.

Another exemplary embodiment of an orthopedic device comprising a walker 1200 is shown in FIGS. 37-41. Similar to the other embodiments, the walker 1200 includes complementary base and dorsal shells 1202, 1204 and a plurality of straps 1206 arranged to bring the base shell 1202 and the dorsal shell 1204 closer together. This embodiment includes a stabilizing part 1208 positioned on a posterior aspect of the base shell 1202 that is arranged to support the walker 1200 against rotation (e.g., external and/or internal rotation) when a patient has their foot elevated or is resting the foot with the posterior aspect of the walker 1200 on a resting surface 1201 such as a bed, the ground, an examination table, a couch, or any other applicable surface.

Conventional walkers typically have rounded posterior heel profiles (when viewed from the proximal aspect of the calf) based on the internal features of the walker to accommodate the patient's rounded heel anatomy. This rounded posterior heel profile of the walker causes the walker to be relatively unstable when the patient is elevating their foot and resting the walker on the posterior aspect of the walker. In addition, the walker tends to be fairly heavy as compared to the typical weight of the patient's foot, which, in turn, tends to cause the walker to roll or externally rotate when the walker is elevated. Furthermore, patients tend to rest with their feet externally rotated (e.g., toed-out to the lateral side) further exacerbating the instability of the walker.

The stabilizing part 1208 supports the walker 1200 against rotation when a patient is resting the foot without substantially affecting the functionality of the walker 1200 during gait. It also does so without the use of complicated and bulky components. Furthermore, the stabilizing part 1208 can be a separate add-on component to the walker and can be adapted to fit a number of different orthopedic devices, providing versatility.

The stabilizing part 1208 can be formed in a single piece and of the same material as the base shell 1202. The stabilizing part 1208 can be formed of a semi-rigid or rigid material such as, for example, rigid plastic like polypropylene and/or a softer material such as foam. According to a variation, an elastomer can be overmolded or adhered to the stabilizing part 1208 to provide a softer contact surface in the event the stabilizing part 1208 contacts external objects. The stabilizing part 1208 can be separate from or integral to the posterior heel portion 1214 of the walker.

In an embodiment, the stabilizing part 1208 comprises an elongate body 1210 arranged to be secured across the posterior heel portion 1214 of the base shell 1202. The body 1210 can wrap or extend around a portion of the lateral and/or medial side of the walker 1200.

The body 1210 defines an inner surface 1216, an outer surface 1218 opposite the inner surface 1216, and side surfaces 1220 extending between the outer and inner surfaces 1218, 1216. The inner surface 1216 is arranged to engage the posterior heel portion 1214 and is contoured to generally correspond to the shape or curvature of the posterior heel portion 1214 of the walker 1200. This can allow the stabilizing part 1208 to form a better fit between the body 1210 and the posterior heel portion 1214. The inner surface 1216 can also provide a support area for the body 1210 against the base shell 1202 when a patient is resting the foot with the posterior aspect of the walker 1200 on a resting surface.

As noted above, the stabilizing part 1208 has a low-profile configuration such that it generally does not disrupt a patient's gait while it is secured to the posterior heel portion 1214. The body 1210 can have a width that is between about 0.5 times and about 1 times (e.g., about 0.9 times), about 0.6 times and about 0.9 times, or about 0.7 times and about 0.8 times a maximum width of the walker 1200. In other embodiments, the body 1210 can have a greater or lesser width.

In an embodiment, the outer surface 1218 of the body 1210 can have a width generally corresponding to the width of the posterior aspect of the walker 1200. The outer surface 1218 can have width between about 3 inches and about 7 inches, about 3.5 inches and about 6.5 inches, or about 4 inches and 6 inches. In other embodiments, the outer surface 1218 can have a greater or lesser width.

Figure 40:
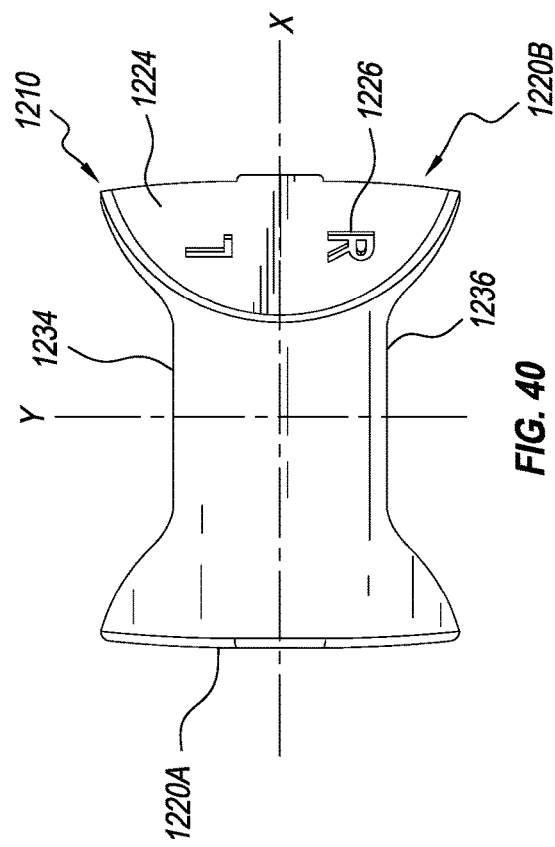
FIG. 40 is back view of the stabilizing part in FIG. 37.
Figure 39:
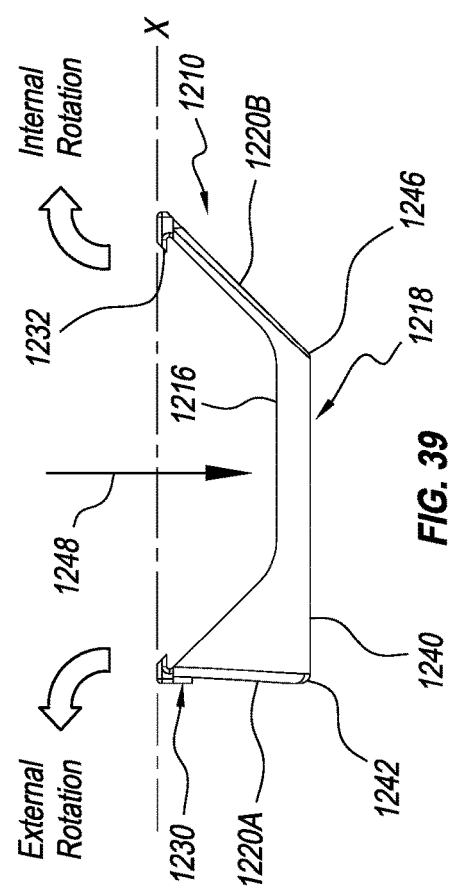
FIG. 39 is a top view of the stabilizing part in FIG. 37.

As seen in FIGS. 39 and 40, the body 1210 extends along an axis X between the side surfaces 1220. An axis Y extends along a height of the body 1210 between the upper and lower edges so that the axis Y intersects the axis X. The body 1210 can define upper and lower cutouts 1234, 1236. The cutouts 1234, 1236 reduce the weight of the stabilizing part 1208 and improve the fit of the stabilizing part 1208 on the posterior heel portion 1214 of the walker 1200.

The stabilizing part 1208 includes at least one counter-rotation feature 1240 arranged to support the walker 1200 against external and/or internal rotation when a patient is resting the posterior aspect of the walker 1200 on the resting surface. In the illustrated embodiment, the at least one counter-rotation feature defines a first point of rotation 1242 about which the walker 1200 will have to overturn to externally rotate and a second point of rotation 1246 about which the walker 1200 will have to overturn to internally rotate. The first and second points of rotation 1242, 1246 are each offset a distance from a center of mass 1248 of the walker 1200 along the axis X. The distances between the first and second rotation points 1242, 1246 and the center of mass 1248 can be the same or different. At least one of the first point of rotation 1242 and the second point of rotation 1246 can be offset a distance from the center of mass 1248 of greater than about 0.3 times, 0.4 times 0.5 times, or about 0.6 times the width of the posterior aspect of the walker 1200.

If the posterior heel portion 1214 of the walker 1200 is resting on a resting surface and leans toward one side or the other, a driving moment is created that tends to rotate the walker 1200 about the first or second points of rotation 1242, 1246. Because the points of rotation are spaced a distance from the center of mass 1248 along the axis X, the weight of the walker 1200 can provide a counterforce that creates a resisting moment in the opposite direction about the first or second points of rotation 1242, 1246. This resisting moment can resist rotation of the walker 1200 about the points of rotation 1242, 1246, stabilizing the walker 1200 on the resting surface.

When the posterior heel portion 1214 of the walker 1200 is resting on a resting surface and the walker 1200 tends to externally rotate about the first point of rotation 1242 of the counter-rotation feature 1240 on the resting surface, the weight of the walker 1200 can provide a counter force that creates a resisting moment in the opposite direction about the first point of rotation 1242, supporting the walker 1200 against such external rotation.

When the posterior heel portion 1214 of the walker 1200 is resting on a resting surface and the walker 1200 tends to internally rotate about the second point of rotation 1246 of the counter-rotation feature 1240 on the resting surface, the weight of the walker 1200 can provide counter force that creates a resisting moment in the opposite direction about the second point of rotation 1246, supporting the walker 1200 against such internal rotation.

The stabilizing part 1208 can thus stabilize the walker 1200 against both internal and external rotation when the patient is resting the foot with the posterior aspect of the walker 1200 on a resting surface. It will be appreciated that when the walker 1200 with the stabilizing part 1208 is placed on a softer resting surface, the stabilizing part 1208 can partially sink or be absorbed into the softer resting surface to allow or accommodate some degree of external rotation of the walker 1200. For instance, the stabilizing part 1208 can sink and partially rotate on the resting surface to accommodate between about 5 and about 7 degrees external rotation of the walker 1200.

As seen FIG. 39, the at least one counter-rotation feature 1240 is a portion of the outer surface 1218 being generally flat or level in a transverse direction along the axis X. The flat or level of the outer portion 1218 can extend between the side surfaces 1220A, 1220B.

It will be appreciated that other counter-rotation features are possible. For instance, the at least one counter-rotation feature can include the outer surface 1218 being concave across the width of the outer surface 1218. In other embodiments, the at least one counter-rotation feature can include posteriorly extending lateral and medial support arms on the outer surface 1218 defining first and second rotation points, each offset a distance from a center of mass 1248 of the walker 1200 along the axis X.

While two points of rotation are described, it will be appreciated three, four, or any other suitable number of points of rotation are possible. For instance, the at least one counter-rotation feature can define a lateral point of rotation spaced from the center of mass 1248 but not a medial point of rotation so that the stabilizing part 1208 only substantially supports the walker 1200 against external rotation.

In other embodiments, one of the points of rotation can be closer to the center of mass than the other so that the stabilizing part 1208 provides more support against rotation along the axis X in one direction than another direction. In addition, while the stabilizing part is described for use on a walker, in other embodiments, the stabilizing part can be arranged for use with a cast, a therapeutic boot, or any other suitable orthopedic device.

According to a variation, the side surface 1220A can define a generally flat surface extending substantially normal to the outer surface 1218. Opposite the side surface 1220A, the side surface 1220B can define an inclined surface 1224 extending between the inner and outer surfaces and arranged to extend along the medial side of the walker 1200. The inclined surface 1224 advantageously lowers the profile of the stabilizing part 1208 along the medial side, helping to reduce the likelihood of the stabilizing part 1208 catching or bumping against the unaffected leg during gait. The inclined surface 1224 also can enhance the flexibility of the body 1210 at or near the side surface 1220B, facilitating attachment of the stabilizing part 1208 to the walker 1200.

The stabilizing part 1208 can also be configured so that it can be used on the left foot or the right foot. For instance, FIG. 40 illustrates the body 1210 being substantially symmetric about the axis X. This advantageously allows the same stabilizing part 1208 to be used on the left or right foot by simply turning the body 1210 over and attaching it to the walker 1200. Such a configuration can allow a patient to position the inclined surface 1224 along the medial side of the walker 1200 on either the right or left foot as needed. Optionally, the stabilizing part 1208 includes visual indicators 1226 to clarify which orientation of the body 1210 is to be used for which foot. The visual indicators 1226 may include an "R" for right and an "L" for left.

The stabilizing part 1208 can be secured to the posterior heel portion 1214 of the walker 1200 in any suitable manner. For instance, the body 1210 can include an attachment system 1230 for securing the stabilizing part 1208 on the posterior heel portion 1214. The attachment system 1230 can include hook members 1232 defined by the body 1210 arranged to selectively clip or lock in one or more attachment holes 1238 (shown in FIG. 38) defined on the base shell 1202. The hook members 1232 can be configured to engage an interior surface of the base shell 1202 when the body 1210 is secured on the posterior heel portion 1214. In other embodiments, the attachment system 1230 can comprise hook-and-loop systems, snaps, fasteners, or any other suitable system.

Figure 41:
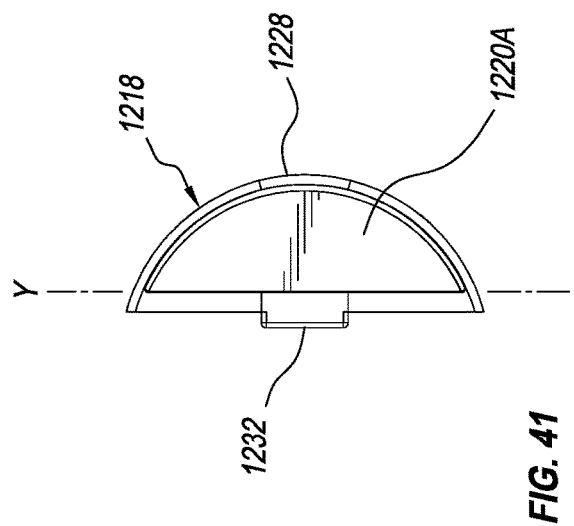
FIG. 41 is a side view of the stabilizing part in FIG. 37.

As seen in FIG. 41, the outer surface 1218 can also be contoured in a vertical direction (e.g., about the axis X or generally between the upper and lower edges). For instance, the outer surface 1218 of the body 1210 can curve in the vertical direction along the axis Y upward (e.g., away from the inner surface) from the lower edge through an apex 1228, and then downward to the upper edge. The radius of the curvature of the outer surface 1218 along the axis Y can be constant or can vary. Thus, the outer surface 1218 along the axis Y can be convexly curved. This advantageously reduces the likelihood of the stabilizing part 1208 from catching during use, or more specifically when descending stairs. This also advantageously allows the walker 1200 to be titled or slightly pivoted with respect to the resting surface, such that the body 1210 still supports the position of the patient's foot even when the posterior of the walker 1200 is not completely parallel to the resting surface. In other embodiments, the outer surface 1218 can be contoured in the vertical direction such that the body 1210 has a faceted, trapezoidal, or other cross-section shape.

Figure 42:
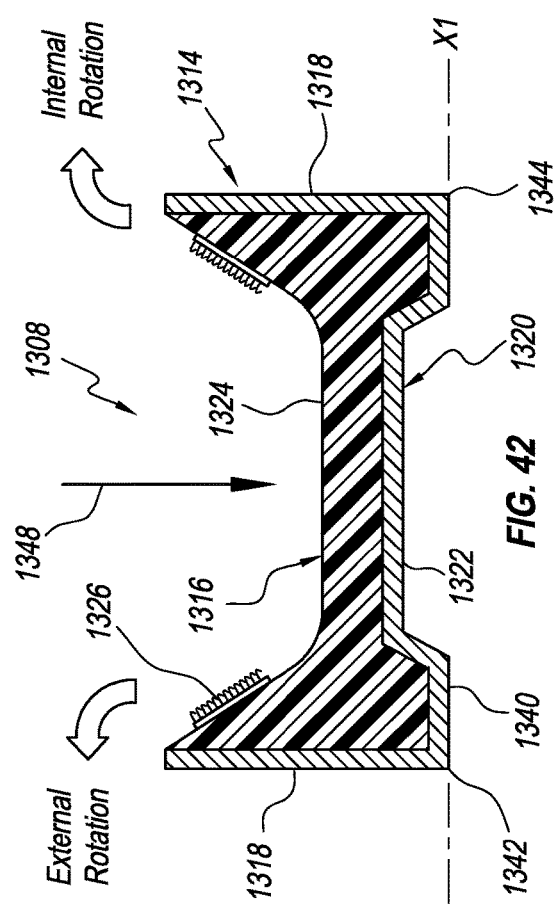
FIG. 42 is a top view of a stabilizing part according to another embodiment.

Another exemplary embodiment of a stabilizing part 1308 is shown in FIG. 42. The stabilizing part 1308 comprises an outer member 1314 having a rigid or semi-rigid configuration and an inner member 1316. The outer member 1314 can include a pair of side members 1318 arranged to extend along a portion of the lateral and medial sides of a walker and a center portion 1320 extending between the side members 1318. The center portion 1320 can include at least one counter-rotation feature comprising a central channel 1322 in the outer surface and supports 1340 on opposite sides of the central channel 1322.

The supports 1340 define a first point of rotation 1342 about which a walker will have to overturn to externally rotate and a second point of rotation 1344 about which the walker will have to overturn to internally rotate. The first and second points of rotation 1342, 1344 are each offset a distance from a center of mass 1348 of a walker along an axis X1. As such, if the posterior aspect of the walker is resting on a resting surface and leans toward one side or the other, a driving moment is created that tends to rotate the walker about the first or second points of rotation 1342, 1344. Because the points of rotation 1342, 1344 are spaced a distance from the center of mass 1348 along the axis X1, the weight of the walker on the stabilizing part 1308 can create a resisting moment in the opposite direction about the first or second points of rotation 1342, 1344 that tends to resist rotation of the walker about the points of rotation 1342, 1344, stabilizing the walker on the resting surface.

The inner member 1316 can be attached to the outer member 1314 and define an inner surface 1324 arranged to engage the posterior heel portion of the walker. The inner surface 1324 extends across the posterior of the walker and along a portion of the lateral and medial sides of the walker. According to a variation, the inner member 1316 can be formed of a softer material arranged to conform to the shape of the walker, allowing the stabilizing part 1308 to fit walkers of different shapes.

The stabilizing part 1308 can be attached to the walker in any suitable manner but is shown being removably attachable to a walker via a hook-and-loop type system 1326. In other embodiments, the stabilizing part 1308 can be attached to the walker via clips, fasteners, magnets, adhesives, or any other suitable attachment system.

Figure 44:
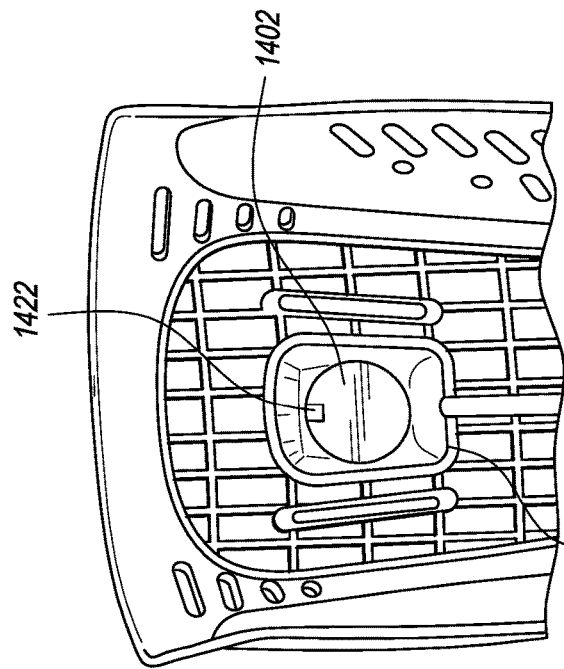
FIG. 44 is a front view of the inside of the orthopedic device in FIG. 43.
Figure 45:
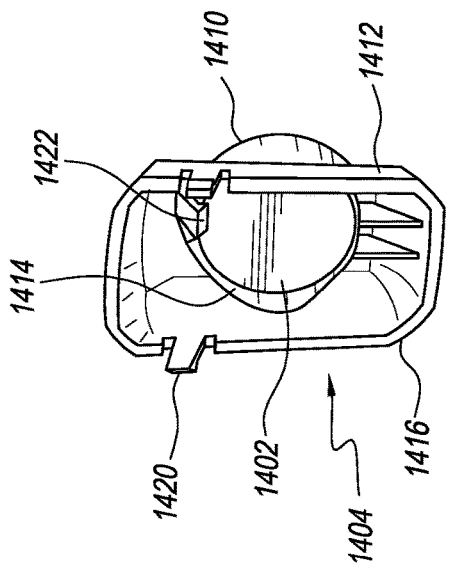
FIG. 45 is a front view of the cover member and activity tracking device in FIG. 43 removed from the orthopedic device for ease of reference.
Figure 43:
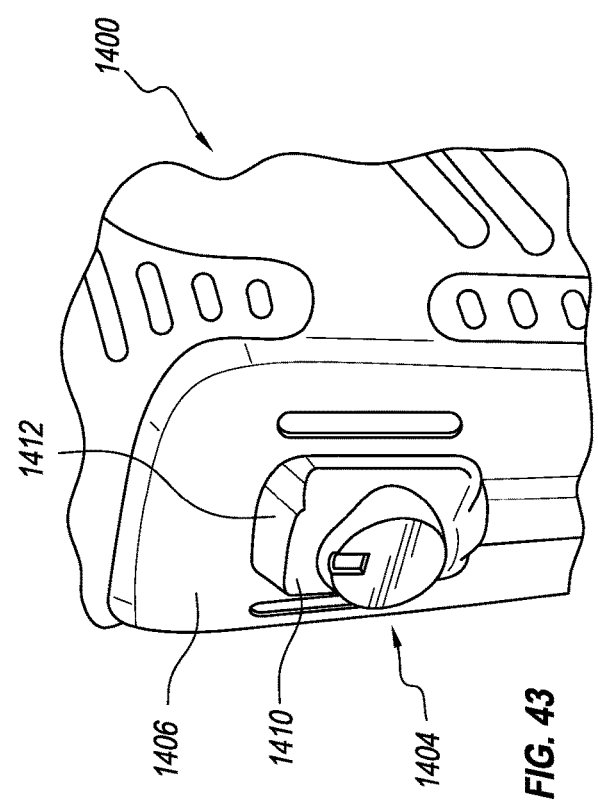
FIG. 43 is a back isometric view of an orthopedic system according to another embodiment.

As noted above, embodiments of the orthopedic system can be adapted for use with other components. FIGS. 43-45 illustrate another embodiment including an activity tracking device integrated into an orthopedic device comprising a walker. This beneficially allows a clinician to monitor a patient's activity levels and/or compliance by identifying both patients who may be too active as well as those who may be inactive (potentially indicating a lack of compliance with clinician instructions).

Conventional walkers do not integrate a means of remotely monitoring patient activity level or compliance with physician instructions. This can lead to negative patient outcomes with unknown or difficult to diagnose causes. For instance, a very active patient may be running or jogging with sprains or factures of the lower leg, increasing stress on an injury and delaying healing. Alternatively, a patient may be removing a walker which is required for a specific treatment, such as in the case of diabetic ulcer healing, where lack of compliance is believed to be a common cause of increased diabetic ulcer healing time.

In the illustrated embodiment, an activity tracking device 1402 is added to or integrated with a walker 1400 and linked or registered within a software application or remote patient monitoring system. The activity tracking device 1402 can generate information associated with the patient's level of activity or compliance during treatment. A clinician can then access and use the data or information collected by the activity tracking device 1402. The clinician can have continuous or intermittent access to the data or information collected by the activity tracking device 1402. For instance, the clinician may only be able to access the data or information from the activity tracking device 1402 during an office visit or during a specific period of time. In other embodiments, the clinician may be able to access the information or data on demand or at any time.

The clinician can use the data or information for determining compliance and/or monitoring the patient's activity level. A clinician can also use such information for troubleshooting potential treatment issues and/or to identify other treatment options for the patient. This advantageously offers an improvement over prior art walkers, which are unable to track and report on a patient's activity during therapy. While the orthopedic device is described as a walker, it will be appreciated that in other embodiments the orthopedic device can be a therapeutic shoe, a total contact cast, or any other suitable orthopedic device.

The activity tracking device 1402 can be any suitable device. The activity tracking device 1402 can include one or more sensors such as a three-dimensional accelerometer to sense patient movement. The activity tracking device 1402 can measure steps taken and combine this data with individual patient characteristics to calculate distance walked, calories burned, floors climbed, activity duration, and/or activity intensity. The activity tracking device 1402 can measure periods of inactivity. In other embodiments, the one or more sensors may include pressure sensors, force sensors, and/or temperature sensors.

The activity tracking device 1402 can include a control system to receive and/or process information from the one or more sensors and/or connect, and transmit information to a computer device or system as described below. The activity tracking device 1402 can be a sealed or waterproof unit and/or have a long battery life (e.g., greater than about 3 months), enhancing the usability of the system, as walkers tend to get wet during use and some patients visit their clinicians infrequently, creating a lengthy time between opportunities for charging.

The activity tracking device 1402 can be integrated in the walker 1400 in a variety of different ways. For example, the activity tracking device 1402 is positioned under a cover member 1404 attached to the posterior aspect of a base shell 1406 of the walker 1400. Placement of the activity tracking device 1402 on the posterior aspect of the walker 1400 reduces the likelihood of patient tampering or interference as the activity tracking device 1402 is out of the patient's sight and is more difficult to access during use.

In an embodiment, the cover member 1404 can be a removable and replaceable component of the walker 1400. For instance, the cover member 1404 can be sized and configured to be interchangeable with embodiments of the air system cover previously described. As such, the cover member 1404 and activity tracking device 1402 can be an add-on module or accessory sold separately from the walker 1400.

As seen in FIGS. 43 and 44, the cover member 1404 can be attached to the base shell 1406 over a cutout 1408 formed in the walker 1400. The cover member 1404 includes a base portion 1410 and a peripheral sidewall 1412 extending from the base portion 1410 toward the base shell 1406 of the walker 1400.

As shown in FIG. 45, a receiving space 1414 in the cover member 1404 is bounded by the sidewall 1412 and the base portion 1410 so that the bottom of the receiving space 1414 is recessed within the sidewall 1412 to provide a space for the activity tracking device 1402. This can allow the base portion 1410 and the sidewall 1412 to substantially enclose the activity tracking device 1402 within the receiving space 1414, protecting the activity tracking device 1402 and helping to deter tampering. The cover member 1404 also helps reduce the likelihood of the activity tracking device 1402 being accidentally dislodged during use. The activity tracking device 1402 can be secured in the receiving space 1414 via a hook member 1422 defined on the inner surface of the cover member 1404. The activity tracking device 1402 can be secured in the receiving space 1414 via an interference fit between the cover member 1404 and the activity tracking device 1402. The activity tracking device 1402 can be secured in the receiving space 1414 via adhesives, a snap fit, or any other suitable manner.

The sidewall 1412 defines a rim 1416 extending around the base portion 1410. At least a portion of the rim 1416 can be contoured to generally correspond to the contour or shape of the posterior of the base shell 1406. This can allow the cover member 1404 to form a better fit between the cover member 1404 and the base shell 1406. The rim 1416 can also provide a support area for the cover member 1404 when the cover member 1404 is attached to the base shell 1406.

The cover member 1404 can be attached to the base shell 1406 in any suitable manner. The cover member 1404 can be secured to the base shell 1406 via a snap-type connection. The cover member 1404 includes a plurality of snaps or hook members 1420 integrally formed on the sidewall 1412 and configured to snap into the cutout 1408 formed in the base shell 1406, facilitating attachment. Alternatively, the cover member 1404 can be removably attached to the base shell 1406 via fasteners, hook-and-loop type systems, clips, magnets, or any other suitable attachment system.

According to another embodiment, the cover member 1404 can be irreversibly attachable to the walker 1400. To protect the activity tracking device 1402 and prevent tampering, the cover member 1404 can be securely attached to the walker 1400 via gluing, plastic welding, or any other suitable manner such that it cannot be removed by the patient without breaking the cover member 1404, which would provide a visible indication of unauthorized tampering with the activity tracking device 1402.

Figure 46:
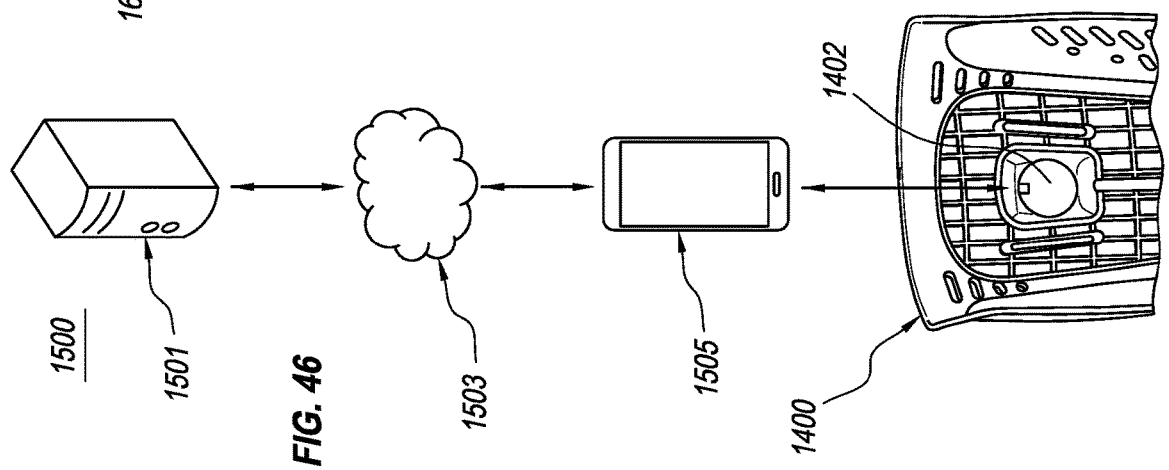
FIG. 46 is an architectural schematic diagram of a monitoring system according to an embodiment.

As noted above, the activity tracking device 1402 can be linked with a software application or patient monitoring system. For instance, the activity tracking device 1402 can be operatively coupled to a monitoring system 1500 including a computer device 1505 as seen in FIG. 46. The computer device 1505 can display information to a patient or clinician and receive input, respectively. For instance, a clinician or patient can input patient characteristics data via the computer device 1505, which, in turn can be processed by the activity tracking device 1402 and/or the computer device 1505 with the step information from the activity tracking device 1402 to calculate activity information such as, but not limited to, distance walked, activity duration, and/or activity intensity. As seen, the computer device 1505 can be a mobile device. A mobile device is a processing device routinely carried by a user. It typically has a display screen with touch input and/or a keyboard, and its own power source. As such, the computer device 1505 can provide a patient or clinician the freedom to use it almost anywhere. The computer device 1505 can be a hand-held device. The computer device 1505 can be a tablet computer, a smartphone, a laptop, a mobile telephone, a PDA, or other appropriate device.

The computer device 1505 can be communicatively coupled to the activity tracking device 1402. The computer device 1505 can be communicatively coupled to the activity tracking device 1402 via a secure or unsecure wireless connection.

The computer device 1505 can be communicatively coupled to a server or computer system 1501 over a network 1503, such as for example, a Local Area Network ("LAN"), a Wide Area Network ("WAN"), or the internet. The computer system 1501 can be used for controlling/monitoring the computer device 1505 and/or the activity tracking device 1402. In an embodiment, the computer system 1501 can provide a patient feedback by directing the activity tracking device 1402 to vibrate a vibrator of the activity tracking device 1402 if step or activity information generated by the activity tracking device 1402 and/or the computer device 1505 exceeds a value limit.

The computer system 1501 can be used for exchanging data/files with the computer device 1505 and/or the activity tracking device 1402. For instance, the activity tracking device 1402 can send one or more files including step information and/or activity information to the computer device 1505 and/or the computer system 1501. It will be appreciated that the computer device 1505 can be separate from or integral to the computer system 1501.

This allows a clinician to ascertain the patient's level of activity or compliance during treatment by accessing the information generated by the activity tracking device 1402 remotely via the computer device 1505 and/or the computer system 1501. For instance, the computer device 1505 can provide a clinician feedback if step or activity information generated by the activity tracking device 1402 exceeds or fails to exceed a value limit stored in the computer device 1505 or computer system 1501. The value limit can be based on patient characteristics, treatment protocols, and/or physician instructions. The value limit can be time dependent. In an embodiment, the computer device 1505 can provide a clinician feedback if step information generated by the activity tracking device 1402 indicates that the patient has not taken a step within a specified time period (e.g., a 24-hour period). The clinician can then use such feedback to make a determination of non-compliance.

According to a variation, the clinician may setup the activity tracking device 1402 within the system 1500 via a registration link or program that limits connection to the activity tracking device 1402 to a single user, reducing the likelihood of unauthorized access to the activity tracking device 1402 and helping to maintain patient confidentiality.

The system 1500 thus gives a clinician freedom to monitor the patient's activity level and/or compliance from almost anywhere and at any time without having to have physical access to the activity tracking device 1402. For instance, the clinician can access the activity tracking device 1402 wirelessly via the computer device 1505 or the computer system 1501 during office visits or routine check-ups. Information generated by the system 1500 can then be used by the clinician for troubleshooting potential treatment issues or to identify other courses of treatment for the patient. According to a variation, the activity tracking device 1402 can be accessed physically by a clinician.

The exact division of labor between the computer system 1501, the activity tracking device 1402, and the computer device 1505 may vary. For instance, the computer device 1505 can receive and store data/files from the activity tracking device 1402, and the activity tracking device 1402 can perform all other operations. In other embodiments, the activity tracking device 1402 can transmit data to the computer device 1505 and/or computer system 1501 and the computer device 1505 and/or computer system 1501 processes, stores, and displays information to the clinician. Any division of labor between the activity tracking device 1402, the computer device 1505, and the computer system 1501 is also within the scope of the present disclosure.

Figure 47:
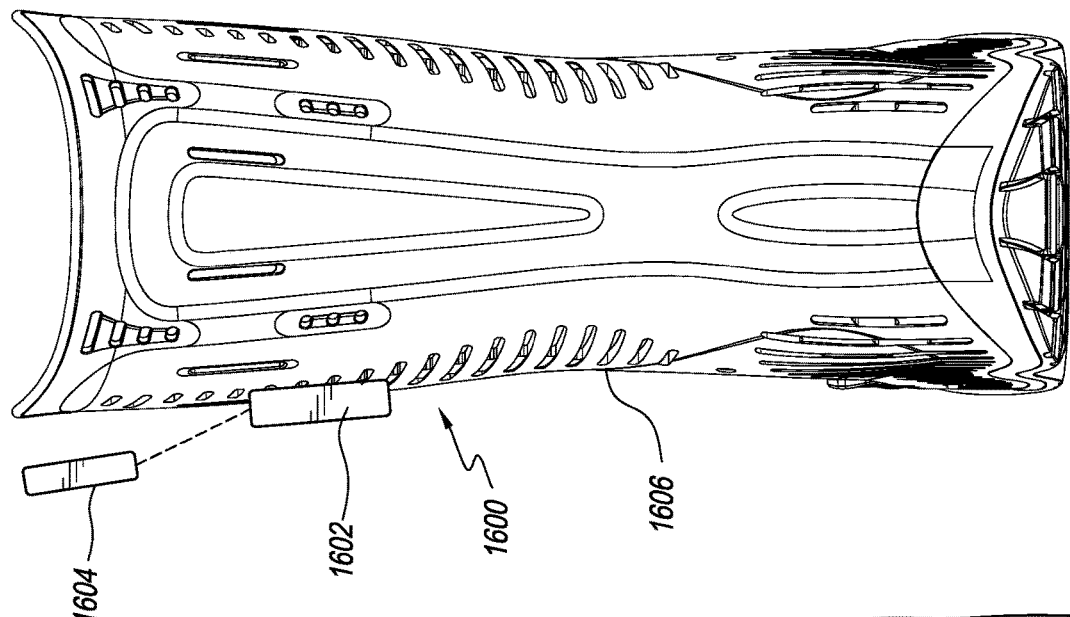
FIG. 47 is a back view of an orthopedic system according to another embodiment.

In other embodiments, the walker can be modified, providing a receptacle to receive and secure embodiments of the activity tracking device. FIG. 47 illustrates another embodiment of a walker 1600 defining a receptacle 1602 having a receiving space arranged to receive and secure an activity tracking device 1604 in the receptacle 1602. This can allow for the activity tracking device 1604 to be sold as a stand-alone accessory or with the walker 1600 as a package. As seen, the receptacle 1602 can be positioned on a side of a base shell 1606 of the walker 1600. This permits the activity tracking device 1604 to be located on the lateral side of the walker 1600, which, in turn, helps prevent the activity tracking device 1604 from interfering with the patient's gait.

Figure 48:
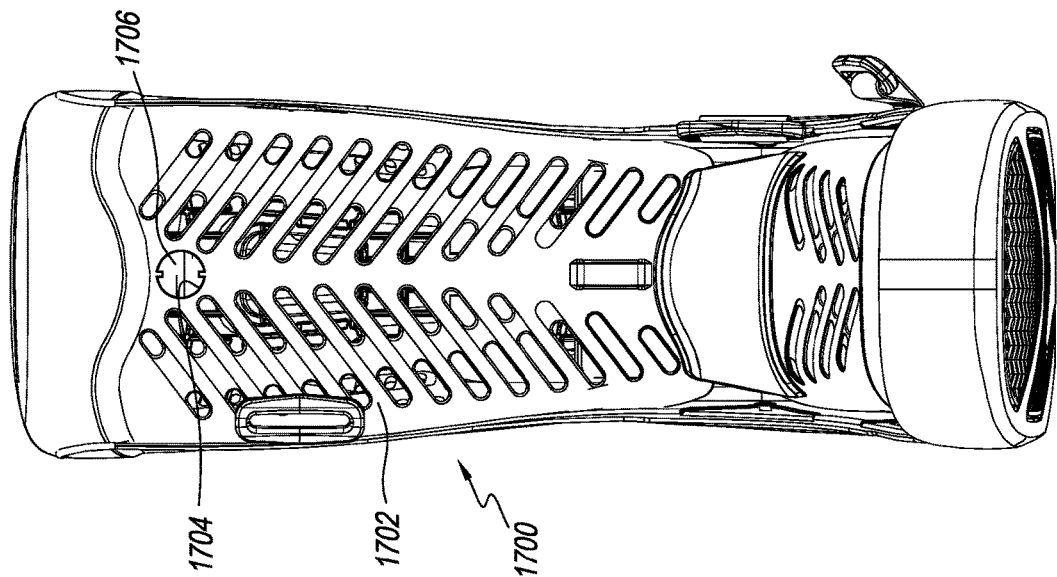
FIG. 48 is a front view of an orthopedic system according to another embodiment.

According to a variation, the activity tracking device can be integrated with the dorsal shell. For instance, FIG. 48 shows another embodiment of a walker 1700 including a dorsal shell 1702 defining a receptacle 1704 having a receiving space arranged to receive an activity tracking device 1706. It will be appreciated that the receptacle 1704 can be formed on the inner or outer surfaces of the dorsal shell 1702 and/or in the proximal shell section or the distal shell section. Integrating the activity tracking device 1706 on the dorsal shell may enhance the accuracy of data generated by the activity tracking device 1706 because the movement of the activity tracking device on the dorsal shell may more closely track the actual movement of the patient's foot and/or lower leg.

In yet other embodiments, the activity tracking device can be secured to a strap member of the walker, making the activity tracking device easy to attach and access for a clinician. In other embodiments, the activity tracking device can be integrated into an insole, outsole, or any other suitable portion of an orthopedic device.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open-ended and have the same meaning as the word "comprising" and variants thereof (e.g., "comprise" and "comprises").

The invention claimed is:

1. An orthopedic system comprising:
   a base shell having ankle and foot receiving portions, the base shell forming an opening over a dorsal aspect thereof;
   a dorsal shell contoured to generally correspond to the opening of the base shell, the dorsal shell having a proximal member and a distal member connected to the proximal member, each of the distal member and the proximal member having a semi-rigid shell configuration to protect and support a lower leg, an ankle, or a foot of a user when received in the orthopedic system; and the dorsal shell further comprising a flexible toe portion defining a proximal sidewall portion overmolded onto a distal terminal end area of the distal member, and a distal sidewall portion extending opposite to the proximal sidewall portion to form a terminal distal end of the dorsal shell, the flexible toe portion formed of a different material than the distal member, the flexible toe portion arranged to terminate above an upper surface of toes of the user and to flex relative to the distal member and the toes so as to reduce the likelihood of pressure points on the toes from the distal member;

wherein the dorsal shell further comprises a flexible shin portion having a distal sidewall portion attached to a proximal terminal end area of the proximal member, and a proximal sidewall portion of the flexible shin portion extending opposite to the distal sidewall portion to form a terminal proximal end of the dorsal shell, the flexible shin portion formed of a different material than the proximal member, the flexible shin portion arranged to flex relative to a front of the lower leg and the proximal member so as to reduce the likelihood of pressure points on the front of the lower leg from the proximal member.

2. The orthopedic system of claim 1, wherein a flexible connecting portion connects the proximal and distal members of the dorsal shell.

3. The orthopedic system of claim 2, wherein the flexible connecting portion is located between a first ridge and a second ridge, the first ridge being located on the distal member at or near a first terminal end of the distal member and the second ridge being located on the proximal member at or near a second terminal end of the proximal member opposite the first terminal end.

4. The orthopedic system of claim 3, wherein the first and second ridges are arranged to limit proximal movement and distal movement of an ankle strap member extending across the flexible connecting portion.

5. The orthopedic system of claim 3, wherein the first and second ridges have different shapes.

6. The orthopedic system of claim 1, wherein the flexible toe portion includes a body portion attached to the distal member and a toe relief portion extending upwardly away from the body portion and forming a space between the flexible toe portion and the toes.

7. The orthopedic system of claim 6, wherein the toe relief portion is arranged to flex away from the toes and back toward an outer surface of the distal member.

8. The orthopedic system of claim 1, wherein the flexible shin portion includes a body portion attached to the proximal member and a tibia relief portion curving outwardly from the body portion and forming a space between the flexible shin portion and the lower leg.

9. The orthopedic system of claim 8, wherein the tibia relief portion is arranged to flex away from the leg and toward an outer surface of the proximal member.

10. The orthopedic system of claim 1, wherein the distal member includes a ridge extending between a lateral side and a medial side of the distal member, the ridge arranged to increase an attachment surface area between the distal member and the flexible toe portion.

11. The orthopedic system of claim 1, wherein the flexible toe portion is formed of an elastomeric material.

12. The orthopedic system of claim 1, wherein the flexible toe portion is removable from the distal member.

13. The orthopedic system of claim 1, wherein the distal sidewall portion of the flexible shin portion is curved to accommodate a tibial crest area of the user.

14. The orthopedic system of claim 1, further comprising at least one observation hole having a triangular periphery formed in the base shell posterior of a malleoli of the user, the at least one observation hole arranged for tactile confirmation of the position of the foot within the base shell.

15. An orthopedic system comprising:
a base shell having ankle and foot receiving portions, the base shell forming an opening over a dorsal aspect thereof;
a dorsal shell contoured to generally correspond to the opening of the base shell, the dorsal shell having a proximal member and a distal member connected to the proximal member, each of the proximal member and the distal member having a semi-rigid shell configuration to protect and support a lower leg, an ankle, or a foot of a user when received in the orthopedic system;
the dorsal shell further comprising a flexible toe portion defining a proximal sidewall portion attached to a distal terminal end area of the distal member, and a distal sidewall portion extending opposite to the proximal sidewall portion to form a terminal distal end of the dorsal shell, the flexible toe portion formed of a different material than the distal member, the flexible toe portion arranged to terminate above an upper surface of toes of the user and to flex relative to the distal member and the toes so as to reduce the likelihood of pressure points on the toes from the distal member; and
the dorsal shell further comprising a flexible shin portion having a distal sidewall portion attached to a proximal terminal end area of the proximal member, and a proximal sidewall portion of the flexible shin portion extending opposite to the distal sidewall portion to form a terminal proximal end of the dorsal shell, the flexible shin portion formed of a different material than the proximal member, the flexible shin portion arranged to flex relative to the proximal member and a front of the lower leg so as to reduce the likelihood of pressure points on the front of the lower leg from the proximal member.

16. The orthopedic system of claim 15, wherein the flexible toe portion includes a body portion attached to the distal member and a toe relief portion angling upwardly away from the body portion and forming a space between the flexible toe portion and the toes.

17. The orthopedic system of claim 15, wherein the flexible shin portion includes a body portion attached to the proximal member and a tibia relief portion angling outwardly from the body portion and forming a space between the flexible shin portion and the lower leg.

18. The orthopedic system of claim 15, wherein a bottom edge of the flexible shin portion is curved to accommodate a tibial crest area of the user.

19. An orthopedic system comprising:
a base shell having ankle and foot receiving portions, the base shell forming an opening over a dorsal aspect thereof and at least one observation hole posterior to a malleoli of a user when received in the base shell, the at least one observation hole arranged for tactile confirmation of the position of a foot of the user within the base shell;
a dorsal shell contoured to generally correspond to the opening of the base shell, the dorsal shell having a proximal member and a distal member connected to the proximal member, each having a semi-rigid shell configuration to protect and support a lower leg, an ankle, or the foot of the user;

the dorsal shell further comprising a flexible toe portion defining a proximal sidewall portion attached to a distal terminal end area of the distal member, and a distal sidewall portion extending opposite to the proximal sidewall portion to form a terminal distal end of the dorsal shell, the flexible toe portion of a different material than the distal member, the flexible toe portion arranged to terminate above an upper surface of toes of the user and to flex relative to the distal member and the toes so as to reduce the likelihood of pressure points on the toes from the distal member; and the dorsal shell further comprising a flexible shin portion having a distal sidewall portion attached to a proximal terminal end area of the proximal member, and a proximal sidewall portion of the flexible shin portion extending opposite to the distal sidewall portion to form a terminal proximal end of the dorsal shell, the flexible shin portion formed of a different material than the proximal member, the flexible shin portion arranged to flex relative to the proximal member and a front of the lower leg so as to reduce the likelihood of pressure points on the lower leg from the proximal member.

* * * * *